(12) United States Patent
Brunkow et al.

(10) Patent No.: US 8,110,357 B2
(45) Date of Patent: Feb. 7, 2012

(54) METHOD FOR DETECTING AN INDIVIDUAL WHO IS AFFLICTED WITH OR A CARRIER FOR VAN BUCHEM'S DISEASE

(75) Inventors: Mary E Brunkow, Seattle, WA (US); Sean Proll, Shoreline, WA (US); Brian W Paeper, Seattle, WA (US); Karen Staehling-Hampton, Bothell, WA (US)

(73) Assignee: Celltech R&D, Inc., Bothell, WA (US)

( * ) Notice: Subject to any disclaimer, the term of this patent is extended or adjusted under 35 U.S.C. 154(b) by 0 days.

(21) Appl. No.: 12/870,568

(22) Filed: Aug. 27, 2010

(65) Prior Publication Data
US 2011/0070588 A1    Mar. 24, 2011

Related U.S. Application Data

(63) Continuation of application No. 11/825,118, filed on Jul. 3, 2007, now abandoned, which is a continuation of application No. 10/353,150, filed on Jan. 27, 2003, now abandoned, which is a continuation of application No. PCT/US01/23968, filed on Jul. 30, 2001.

(60) Provisional application No. 60/303,386, filed on Jul. 6, 2001, provisional application No. 60/221,855, filed on Jul. 28, 2000.

(51) Int. Cl.
*C12Q 1/68* (2006.01)
(52) U.S. Cl. ........................................................ 435/6.1
(58) Field of Classification Search .................... None
See application file for complete search history.

(56) References Cited

U.S. PATENT DOCUMENTS 5,994,529 A    11/1999    Feuerstein et al. .......... 536/24.31
6,475,739 B2 *  11/2002    Brunkow et al. .................. 435/6

FOREIGN PATENT DOCUMENTS

WO    WO 93/18177    9/1993

OTHER PUBLICATIONS

Genbank Database, Accession No. AC004149.1, Feb. 19, 1998.
Genbank Database, Accession No. AC055813.9, Apr. 20, 2000.
Balemans, et al., "Localisation of the Gene for Van Buchem Disease to a Candidate Region of Less than 1 cM on Chromosome 17," American Journal of Medicine 61 (suppl.):A12, 1997.
Balemans, et al., "Localization of the Gene for Sclerosteosis to the Van Buchem Disease-Gene Region on Chromosome 17q12-q21," American Journal of Human Genetics 64: 1661-1669, 1999.
Beighton, et al., "The Syndromic Status of Sclerosteosis and Van Buchem Disease," Clinical Genetetics 25:175-181, 1984.

(Continued)

*Primary Examiner* — Samuel Woolwine
(74) *Attorney, Agent, or Firm* — K&L Gates LLP

(57) ABSTRACT

The genomic locus responsible for Van Buchem's disease is narrowed to an approximately 92 kb region of human chromosome 17 at 17q21. Individuals afflicted with or carriers of Van Buchem's disease exhibit a 52 kb deletion within this 92 kb region. Methods are provided that permit the differentiation between individuals homozygous for and therefore afflicted with Van Buchem's disease, individuals heterozygous for and therefore carriers of Van Buchem's disease, and individuals who are normal with respect to Van Buchem's disease. Also provided are general methodologies for the detection of a wide variety of large genomic deletions.

1 Claim, 3 Drawing Sheets

OTHER PUBLICATIONS

Figure 1:
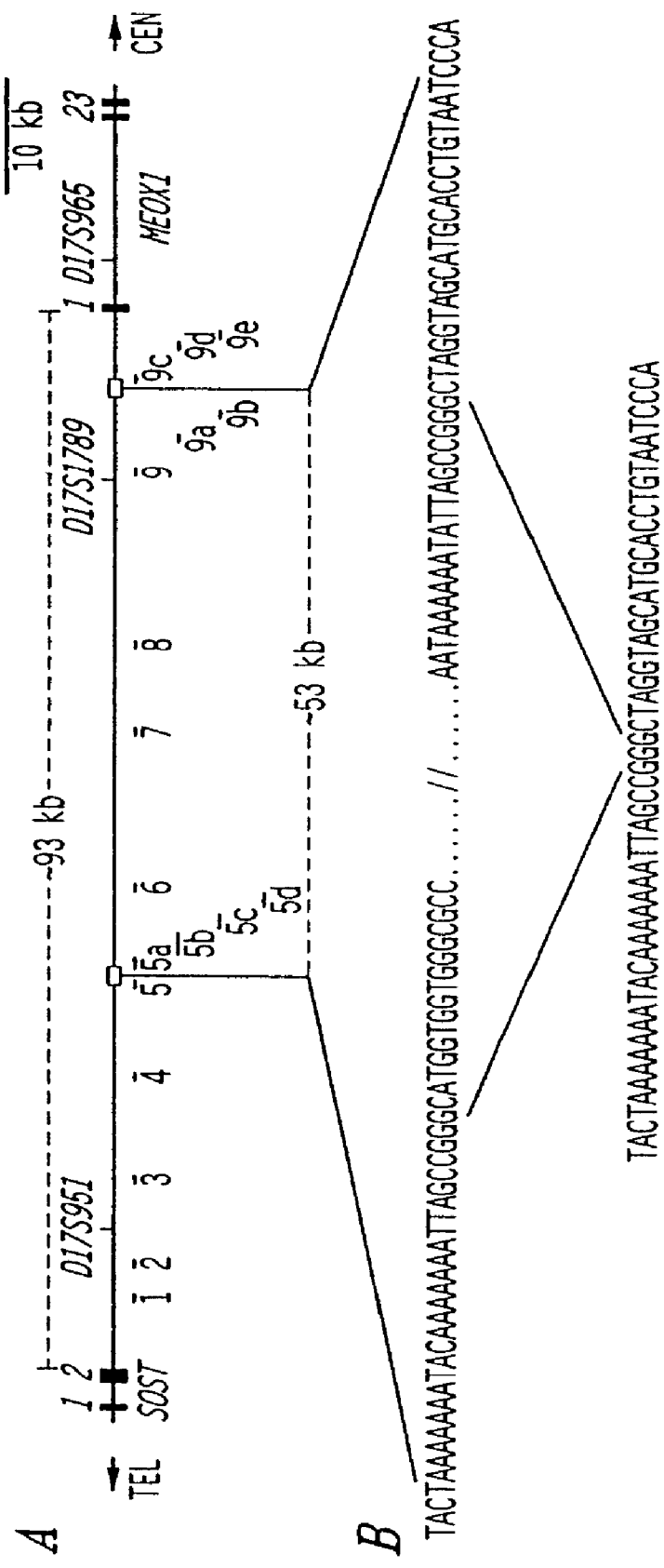

Brunkow, et al., "Bone Dysplasia Sclerosteosis Results from Loss of the *SOST* Gene Product, a Novel Cystine Knot-Containing Protein," Am. J Hum. Genet. 68:577-589, 2001.

Bubert, et al., "Detection and Differentiation of Listeria spp. by a Single Reaction Based on Multiple PCR," App. and Environ. Microbiol. 65(10):4688-4692, Oct. 1999.

Burge, et al., "Prediction of Complete Gene Structures in Human Genomic DNA," J Mol. Biol. 268:78-94, 1997.

Coulter-Mackie, M., et al., "A Protocol for Detection of Mitochondrial DNA Deletions: Characterization of a Novel Deletion," Clin. Biochem. 31(8):627-632, Nov. 1998.

Fryns, et al., "Facial Paralysis at the Age of2 Months as a First Clinical Sign of Van Buchem Disease (Endosteal Hyperostosis)," European Journal of Pediatrics 147:99-100, 1988.

Keinanen, M. et al., "Use of Polymerase Chain Reaction to Detect Heterozygous Familial Hypercholesterolemia," Clin. Chem. 36(6):900-903, 1990.

Kristensen, V. et al., "Single Tube Multiplex Polymerase Chain Reaction Genotype Analysis of GSTM1, GSTT1 and GSTP1: Relation of Genotypes to TP53 Tumor Status and Clinicopathological Variables in Breast Cancer Patients," Pharmacogenetics 8:441-447,1998.

Loots, et al., "Genomic Deletion of a Long-Range Bone Enhancer Misregulates Sclerostin in Van Buchem Disease", Genome Research, vol. 15, pp. 928-935, 2005.

Michalatos-Beloin, S. et al., "Molecular Haplotyping of Genetic Markers 10 kb Apart by Allele-Specific Long-Range PCR," Nuc. Acids Res. 24(23):4841-4843, 1996.

Pittenger, et al., "Multilineage Potential of Adult Human Mesenchymal Stem Cells", Science, vol. 284, pp. 143-147, Apr. 2, 1999.

Rosenberg, C. et al., "Genetic Alterations of Chromosome 17 in Human Breast Carcinoma Studied by Flourescence in Situ Hybridization and Molecular DNA Techniques," Cancer Genet. Cytogenet. 75:1-5, Jan. 1994.

Staehling-Hampton, K. et al., "A 52-kb Deletion in the SOST-MEOXI Intergenic Region onl7q12-q21 is Associated with Van Buchem Disease in the Dutch Population," Am. J Med. Genet. 110:144-152,2002.

Sutherland, et al., "Unique Regulation of *SOST*, the Sclerosteosis Gene, by BMPs and Steroid Hormones in Human Osteoblasts", Bone 35, pp. 448-454, 2004.

Van Buchem, et al., "Hyperostosis Corticalis Generalisata," American Journal ofMedicine33:387-397, 1962.

Van Hul, W. et al., "Van Buchem Disease (Hyperostosis Corticalis Generalisata) Maps to Chromosome 17ql2-q2l," Am. J Hum. Genet. 62:391-399, Feb. 1998.

\* cited by examiner

METHOD FOR DETECTING AN INDIVIDUAL WHO IS AFFLICTED WITH OR A CARRIER FOR VAN BUCHEM'S DISEASE

CROSS-REFERENCES TO RELATED APPLICATIONS

This application is a continuation of U.S. patent application Ser. No. 11/825,118 filed Jul. 3, 2007 now abandoned which was filed as a continuation of U.S. patent application Ser. No. 10/353,150 filed Jan. 27, 2003 now abandoned which was filed as a continuation under 35 U.S.C. §356 of copending International Application PCT/US01/23968, filed July. 30, 2001, which designates the U.S., and which claims priority to U.S. Provisional Patent Application No. 60/303,386, filed Jul. 6, 2001, and U.S. Provisional Patent Application No. 60/221,855, filed Jul. 28, 2000, which are incorporated herein by reference in their entirety.

BACKGROUND OF THE INVENTION

1. Field of the Invention

This invention relates generally to disease diagnosis and to the identification of disease carriers. More specifically, the present invention provides methods for identifying individuals who are afflicted with or carriers of diseases associated with one or more genomic deletion.

2. Description of the Related Art

Van Buchem's disease (VBD) is a rare autosomal recessive disorder that results in a bone dysplasia referred to as craniotubular hyperostosis. VBD was first described in 1962 as including osteosclerosis of the skull, mandible, clavicles, ribs, and diaphysis of the long bones beginning during puberty and, in some cases, leading to optic atrophy and perceptive deafness from nerve pressure. Van Buchem et al., *Am. J. Med.* 33:387-397 (1962).

More recently, additional occurrences of VBD have been reported. In 1988, Fryns et al. described a 7.5-year-old boy with VBD. This patient had presented at 2 months of age with left-side peripheral facial nerve palsy but had, at that time, no radiologically visible signs of sclerosis of the skull. *Europ. J. Pediat.* 147:99-100 (1988).

In 1997, Balemans et al. studied 11 VBD patients from a highly inbred and geophraphically isolated Dutch family. Each of these patients shared a common ancestor from 9 preceding generations. By applying a genome wide search for linkage using more than 300 microsatellite markers having an average spacing of 10 cM, these authors found a maximum lod score of 9.33 at theta=0.01 with marker D17S1299 and narrowed the assignment to a region of less than 1 cM between markers D17S1787 and D17S934. *Am. J. Hum. Genet.* 61(Suppl.):A12 (1997); See, also, Van Hul et al., *Am. J. Hum. Genet.* 62:391-399 (1998).

A related disease sclerosteosis is an autosomal semi-dominant disease that shares some of the clinical symptoms of VBD. The term "sclerosteosis" has been applied to a disorder similar to Van Buchem hyperostosis corticalis generalisata but differing in the radiologic appearance of the bone changes and in the presence of asymmetric cutaneous syndactyl of the index and middle fingers in many cases. In *Handbuch der Kinderheilkunde* 351-355 (Opitz, H. et al., Berlin: Springer (pub.), 1967). More specifically, this disease resembles VBD in that it comprises a progressive sclerosing bone dysplasia characterized by generalized osteosclerosis and hyperostosis of the skeleton, affecting mainly the skull and mandible thereby causing facial paralysis and hearing loss. In contrast to VBD, however, sclerosteosis is further characterized by gigantism and hand abnormalities.

The rare genetic mutation responsible for the sclerosteosis syndrome has been localized to the region of human chromosome 17 that encodes a novel member of the TGF-beta binding-protein family (one representative example of which is designated "hSOST"). In 1999, Balemans et al. assigned the locus for sclerosteosis to 17q12-q21 which is the same general region as the locus for VBD. *Am. J. Hum. Genet.* 64:1661-1669 (1999). Due to the clinical similarities between VBD and sclerosteosis, Beighton et al. suggested that these conditions might be caused by mutations within the same gene. *Clin. Genet.* 25:175-181 (1984). This hypothesis was further supported by the genetic experimentation later performed by Balemans et al. Supra.

Traditional methodologies for identifying genomic deletions such as, for example, restriction fragment length polymorphism (RFLP), fluorescence in situ hybridization (FISH) and Southern blotting permit the identification of individuals who are homozygous for a genomic deletion and, as a consequence, are afflicted with the associated genetic disease. Because these methods are time consuming and/or require high-quality DNA samples or live cells, they are of limited use in the identification of individuals who are heterozygous for and, therefore, carriers of a genetic disease. What is needed in the art are methods that permit the rapid identification of genetic disease carriers, which methods distinguish between individuals who are homozygous for a genomic deletion, individuals who are heterozygous for a genomic deletion and individuals who do not possess a given genomic deletion. As described in detail herein, the present invention fulfills this and other related needs.

BRIEF SUMMARY OF THE INVENTION

The present invention is directed generally to disease diagnosis and to the identification of disease carriers. More specifically, the invention disclosed herein provides methods for identifying chromosomal deletions that are associated with a disease phenotype. Particular methods within the scope of the present invention are directed to the identification of individuals who are afflicted with or carriers for the genomic deletion associated with Van Buchem's disease. By alternate embodiments, the present invention also provides methods having general utility in the detection of a wide variety of diseases characterized by genomic deletions.

The present invention provides, in one embodiment, methods for distinguishing between an individual who is homozygous for a genomic deletion, an individual who is heterozygous for a genomic deletion and an individual who is negative for a genomic deletion.

A first method comprises: (a) obtaining a sample of genomic DNA from an individual; (b) performing a first amplification reaction with a first oligonucleotide primer pair comprising a first oligonucleotide primer and a second oligonucleotide primer wherein the first oligonucleotide primer is complementary to the nucleotide sequence upstream of the genomic deletion and the second oligonucleotide primer is complementary to the nucleotide sequence downstream of said genomic deletion; (c) performing a second amplification reaction with, a second oligonucleotide primer pair comprising a third oligonucleotide primer and a fourth oligonucleotide primer wherein the third oligonucleotide primer is complementary to the nucleotide sequence either upstream or downstream of the genomic deletion and the fourth oligonucleotide primer is complementary to the nucleotide sequence comprising the genomic deletion; and (d) detecting the product of the amplification reactions of (b) and (c).

By this first type method, a positive amplification reaction of (b) and a negative amplification reaction of (c) indicates an individual who is homozygous for the large genomic deletion; a positive amplification reaction of (b) and a positive amplification reaction of (c) indicates an individual who is heterozygous for the large genomic deletion; and a negative amplification reaction of (b) and a positive amplification reaction of (c) indicates an individual who is negative for the large genomic deletion.

A second method comprises: (a) obtaining a sample of genomic DNA from said individual; (b) performing an amplification reaction employing at least two oligonucleotide primer pairs in which an oligonucleotide primer is common to both said primer pairs, wherein a first primer pair has a first oligonucleotide primer complementary to a nucleotide sequence that flanks said genomic deletion upstream of said genomic deletion and a second oligonucleotide primer complementary to a nucleotide sequence that flanks said genomic deletion downstream of said genomic deletion, and a second primer pair has third oligonucleotide primer complementary to a nucleotide sequence within said genomic deletion and either said first or second oligonucleotide primer; and (c) detecting an amplified product of said amplification reaction.

By this second method, a positive amplification reaction of said first primer pair and a negative amplification reaction of said second primer pair indicates an individual that is homozygous for said large genomic deletion; a positive amplification reaction of said first primer and a positive amplification reaction of said second primer pair indicates an individual that is heterozygous for said large genomic deletion; and a negative amplification reaction of said first primer pair and a positive amplification reaction of said second primer pair indicates an individual that is negative for said large genomic deletion.

Both these methodologies will find utility in the detection of large genomic deletions comprising at least 2, 3, 4, 5, 6, 7, 8, 9, 10, 15, 20, 25, 30, 40 or 50 kb. By some embodiments, the presence of the large genomic deletion is indicative of an individual who is either afflicted with or a carrier of a genetic disease. The genetic disease is exemplified herein by Van Buchem's disease, but the methods are suitable for any disease characterized by large genomic deletions.

In further embodiments, the present invention provides a first method for identifying individuals who are afflicted with or carriers of Van Buchem's disease. This first method comprises (a) obtaining a sample of genomic DNA from an individual; (b) performing a first amplification reaction with a first oligonucleotide pair primer having a first oligonucleotide primer and a second oligonucleotide primer wherein the first oligonucleotide primer is complementary to the nucleotide sequence upstream of the 51,719 bp sequence depicted in SEQ ID NO:2 which sequence corresponds to nucleotides 5,798 through 57,516 of the 92,149 bp nucleic acid sequence depicted in SEQ ID NO:1 and the second oligonucleotide primer is complementary to the nucleotide sequence downstream of the 51,719 bp sequence depicted in SEQ ID NO:2; and (c) performing a second amplification reaction with a second oligonucleotide pair primer comprising a third oligonucleotide primer and a fourth oligonucleotide primer wherein the third oligonucleotide primer is complementary to the nucleotide sequence either upstream or downstream of the 51,719 bp sequence depicted in SEQ ID NO:2 and the fourth oligonucleotide is complementary to the nucleotide sequence within the 51,719 bp sequence depicted in SEQ ID NO:2; and (d) detecting the product of the amplification reactions of (b) and (c).

By this first method, a positive amplification reaction of (b) and a negative amplification reaction of (c) indicates an individual afflicted with Van Buchem's disease; a positive amplification reaction of (b) and a positive amplification reaction of (c) indicates an individual who is a carrier of Van Buchem's disease; and a negative amplification reaction of (b) and a positive amplification reaction of (c) indicates an individual that is neither afflicted with nor a carrier of Van Buchem's disease.

Exemplary first oligonucleotide primer pairs may be selected from the group consisting of 12952/VBspan1 (SEQ ID NO:84/SEQ ID NO:85), Span1F/Span1R (SEQ ID NO:86/SEQ ID NO:87), Span2F/Span2R (SEQ ID NO:88/SEQ ID NO:89) and Vbspan2/Vbspan1 (SEQ ID NO:104/SEQ ID NO:85). Exemplary second oligonucleotide pairs may be selected from the group consisting of 12952/Wt1R (SEQ ID NO:84/SEQ ID NO:90), Wt2F/Wt2R (SEQ ID NO:91/SEQ ID NO:92), Wt3F/Wt3R (SEQ ID NO:93/SEQ ID NO:94) and VBspan2/VBint1 (SEQ ID NO:105/SEQ ID NO:102).

A second method comprises: (a) obtaining a sample of genomic DNA from said individual; (b) performing a polymerase chain reaction employing at least two oligonucleotide primer pairs in which an oligonucleotide primer is common to both said primer pairs, wherein a first primer pair has a first oligonucleotide primer, that is complementary to a nucleotide sequence upstream of the 51,719 bp sequence provided in SEQ ID NO:2 and a second oligonucleotide primer that is complementary to a nucleotide sequence downstream of the 51,719 bp sequence provided in SEQ ID NO:2, and a second primer pair has a third oligonucleotide primer that is complementary to a nucleotide sequence within said genomic deletion and either said first or second oligonucleotide primer; and (c) detecting an amplified product of said amplification reaction.

By this second method, a positive polymerase chain reaction of said first primer pair and a negative polymerase chain reaction of said second primer pair indicates an individual afflicted with Van Buchem's disease; a positive polymerase chain reaction of said first primer pair and a positive polymerase chain reaction of said second primer pair indicates an individual that is a carrier of Van Buchem's disease; and a negative polymerase chain reaction of said first primer pair and a positive polymerase chain reaction of said second primer pair indicates an individual that is neither afflicted with nor a carrier of Van Buchem's disease.

Exemplary first oligonucleotide primer pair is selected from the group consisting of 12952/VBspan1 (SEQ ID NO:84/SEQ ID NO:85), Span1F/Span1R (SEQ ID NO:86/SEQ ID NO:87), Span2F/Span2R (SEQ. ID NO:88/SEQ ID NO:89), Wt2F/VBspan1 (SEQ ID NO:91/SEQ ID NO:85) and VBspan2/VBspan1 (SEQ ID NO:104/SEQ ID NO:85).

Still further embodiments of the present invention provide alternative methods for identifying individuals afflicted with Van Buchem's disease. Exemplary methods comprise the steps of performing an amplification reaction with a pair of oligonucleotides selected from the region between nucleotide 1 and nucleotide 51,719 of SEQ ID NO:2 wherein the absence of an amplification product indicates an individual homozygous for Van Buchem's disease. Exemplary oligonucleotide pairs are selected from the group consisting of Del1F/Del1R (SEQ ID NO:95/SEQ ID NO:96), Del2F/Del2R (SEQ ID NO:97/SEQ ID NO:98), and Del3F/Del3R (SEQ ID NO:99/SEQ ID NO:100).

Other embodiments provide methods for identifying an individual who is homozygous for Van Buchem's disease comprising the step of detecting a deletion in human chromosome 17 at 17q21 between nucleotide 5,798 and nucleotide 57,516 as depicted in SEQ ID NO:1.

Figure 2:
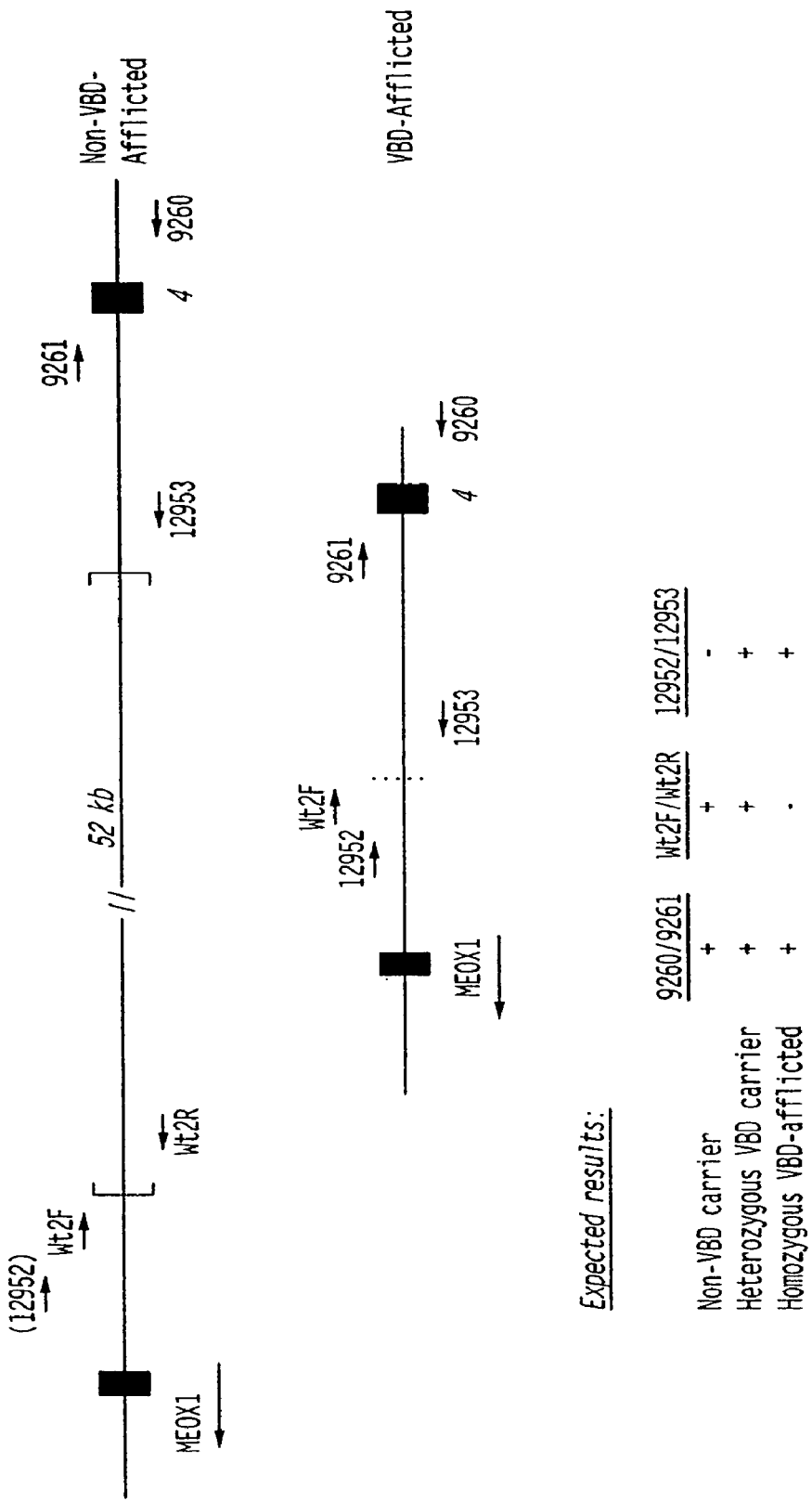

By still other embodiments are provided methods for detecting an individual who is afflicted with or a carrier of Van Buchem's disease which methods comprise detecting the nucleotide sequence spanning the deletion breakpoint as depicted in FIG. 2 and SEQ ID NO:101. By these methods, the presence of a deletion breakpoint indicates an individual who is either, afflicted with or a carrier of Van Buchem's disease. Exemplary nucleotide sequences spanning the deletion breakpoint comprise the nucleotide sequence 5'-ACCATGCCCGGCTAAT-3' (SEQ ID NO:102); the nucleotide sequence 5'-CTACCATGCCCGGCTAATTTT-3' (SEQ ID NO:103); and the nucleotide sequence 5'-TGGGATTACAGGTGCATGCTACCATGCCCGGCTAATTTTTTTGTA TTTTTTTAGTA-3' (SEQ ID NO:101).

In still further embodiments of the present invention are provided isolated polynucleotides. Preferred polynucleotides comprise at least 10, 15, 20, 25, 30, 40, 50, 100, 250 or 500 contiguous nucleotides of the nucleic acid depicted in SEQ ID NO:1. Alternatively, isolated polynucleotides according to the present invention hybridize under moderately stringent conditions to the nucleic acid depicted in SEQ ID NO:1 or the complement thereof. Preferred moderately stringent conditions comprise 2×SSC, 0.1% SDS at 65° C.

Other embodiments provide isolated polynucleotides that comprise at least 10, 15, 20, 25, 30, 40, 50, 100, 250 or 500 nucleotides of one of the amplicons comprising the predicted exons within human chromosome 17 at 17q21 which amplicons are selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

Still further embodiments of the present invention provide diagnostic kits for distinguishing between an individual who is homozygous for a large genomic deletion, an individual who is heterozygous for a large genomic deletion and an individual who is negative for a large genomic deletion.

A first kit comprises: (a) a first oligonucleotide primer pair comprising a first oligonucleotide primer and a second oligonucleotide primer, wherein said first oligonucleotide primer is complimentary to a nucleotide sequence upstream of said genomic deletion and said second oligonucleotide primer is complementary to a nucleotide sequence downstream of said genomic deletion; and (b) a second oligonucleotide primer pair comprising a third oligonucleotide primer and a fourth oligonucleotide primer wherein said third oligonucleotide primer is complementary to a nucleotide sequence either upstream or downstream of said genomic deletion and said fourth oligonucleotide primer is complementary to a nucleotide sequence within said genomic deletion. These types of diagnostic kit can further comprises instructions for distinguishing between an individual who is homozygous for a large genomic deletion, an individual who is heterozygous for a large genomic deletion and an individual who is negative for a large genomic deletion.

A second kit comprises: (a) a first primer pair having a first oligonucleotide primer that is complementary to a nucleotide sequence that flanks said genomic deletion upstream of said genomic deletion and a second oligonucleotide primer that is complementary to a nucleotide sequence that flanks said genomic deletion downstream of said genomic deletion; and (b) a second primer pair having a third oligonucleotide primer that is complementary to a nucleotide sequence within said genomic deletion and either said first or second oligonucleotide primer.

The genomic deletion mentioned can be associated with Van Buchem's disease. In which case one type of diagnostic kit for identifying a carrier of Van Buchem's disease comprises: (a) a first oligonucleotide primer pair comprising a first oligonucleotide and a second oligonucleotide wherein said first oligonucleotide is complementary to a nucleotide sequence upstream of the 51,719 bp sequence depicted in SEQ ID NO:2 and said second oligonucleotide is complementary to a nucleotide sequence downstream of the 51,719 bp sequence depicted in SEQ ID NO:2; and (b) a second oligonucleotide primer pair comprising a third oligonucleotide and a fourth oligonucleotide wherein said third oligonucleotide is complementary to either the nucleotide sequence upstream or downstream of said 51,719 bp sequence depicted in SEQ ID NO:2 and said fourth oligonucleotide is complementary to a nucleotide sequence within said 51,719 bp sequence depicted in SEQ ID NO:2. These diagnostic kits can further comprise instructions for identifying a carrier of Van Buchem's disease.

A second kit comprises: (a) a first oligonucleotide pair having a first oligonucleotide primer that is complementary to a nucleotide sequence upstream of the 51,719 bp sequence provided in SEQ ID NO:2 and a second oligonucleotide primer that is complementary to a nucleotide sequence downstream of the 51,719 bp sequence depicted in SEQ ID NO:2; and (b) a second oligonucleotide pair having a third oligonucleotide primer that is complementary to a nucleotide sequence within said 51,719 bp sequence provided in SEQ ID NO:2 and either said first or second oligonucleotide primer.

BRIEF DESCRIPTION OF THE SEVERAL VIEWS OF DRAWINGS

FIG. 1A illustrates results obtained from microsatellite typing and exon sequencing of the approximately 90 kb region between the MEOX1 and SOST genes within human chromosome region 17q21. FIG. 1B shows the about 53 kb genomic deletion as well as illustrates the nucleotide sequence spanning the deletion breakpoint (SEQ ID NO:101) in nucleic acid sequences obtained from individuals afflicted with Van Buchem's disease. Sequences shown in the figure are: TACTAAAAAATACAAAAAAATTAGC-CGGGCATGGTGGTGGGCGCC (SEQ ID NO: 106); AATAAAAAATATTAGCCGGGCTAGGTAG-CATGCACCTGTAATCCCA (SEQ ID NO:107); and TAC-TAAAAAAATACAAAAAAATTAGC-CGGGCTAGGTAGCACCTGT AATCCCA (SEQ ID NO:108).

FIG. 2 illustrates expected results from the polymerase chain reactions utilizing exemplary oligonucleotide primer pairs in the first-described method, where the nucleic acid sample is obtained from an individual who is (1) a non-carrier for Van Buchem's disease; (2) heterozygous for, and therefore a carrier of, Van Buchem's disease; or (3) homozygous for, and therefore afflicted with, Van Buchem's disease.

Figure 3:
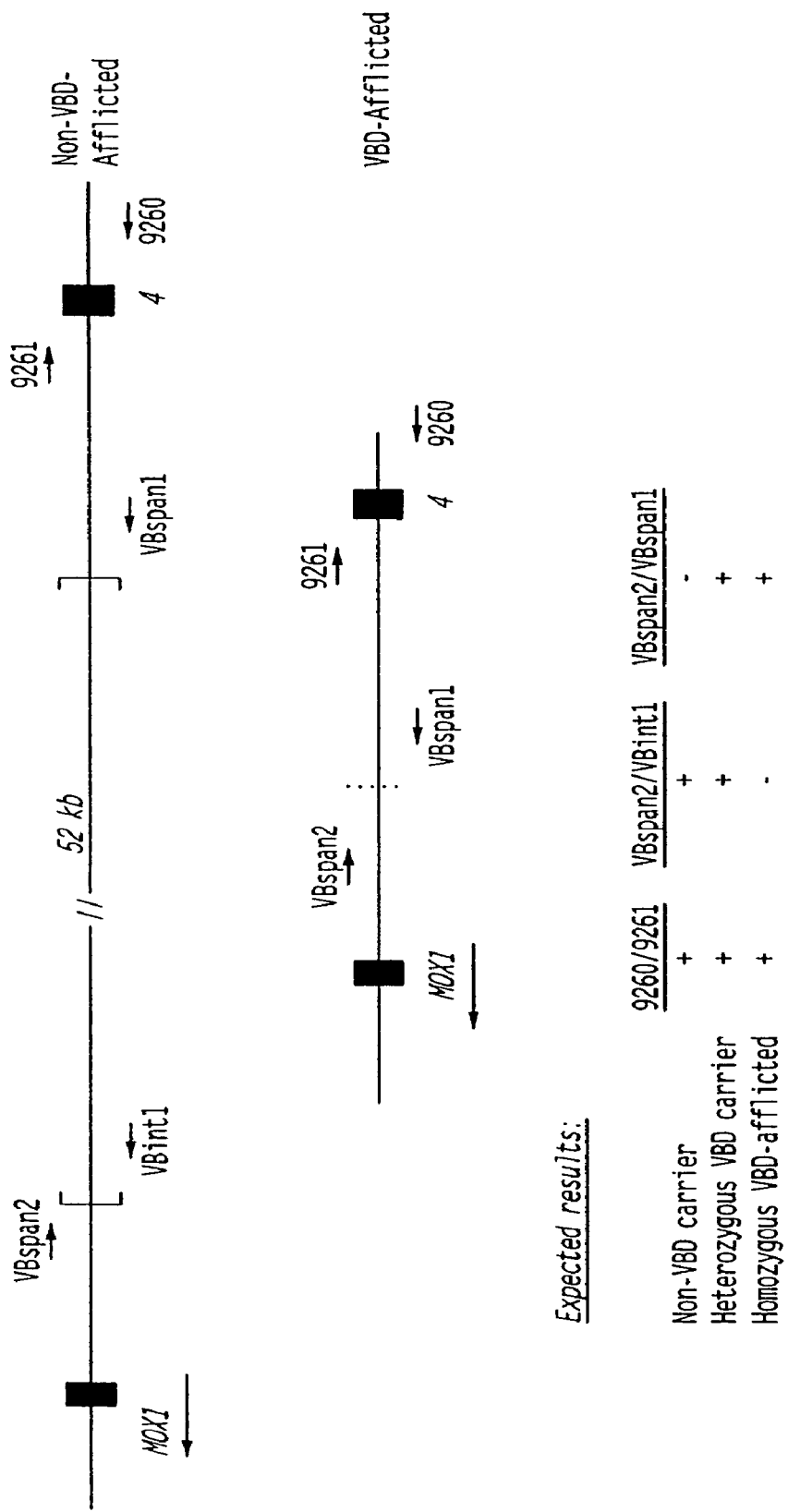

FIG. 3 illustrates expected results from the polymerase chain reaction utilizing exemplary oligonucleotide primer pairs in the second-described method, where the nucleic acid sample is obtained from an individual who is (1) a non-carrier for Van Buchem's disease; (2) heterozygous for, and therefore a carrier of, Van Buchem's disease; or (3) homozygous for, and therefore afflicted with, Van Buchem's disease.

DETAILED DESCRIPTION OF THE INVENTION

As part of the present invention, it was discovered, through haplotype analysis of a number of VBD patients carrying recombinant chromosomes, that the VBD gene localized to a critical region of less than 1 Mb, between the polymorphic markers BP12574 (D17S2250) and JM6307 (D17S2253) (see Example 1). Further microsatellite typing, as well as characterization of the candidate genes within the 1 Mb region through exon sequencing, revealed a specific chromosomal aberration that segregated absolutely with VBD (see Example 3).

As discussed in detail in Example 3, two independent experimental approaches to identifying the VBD candidate region revealed the presence of a chromosomal deletion associated with VBD. First, the oligonucleotide pair D17S1789 (see FIG. 1 and Table 3) did not permit the PCR amplification of a DNA fragment from genomic DNA isolated from VBD patients but did facilitate the amplification of a fragment from normal individuals. Second, nucleotide sequencing and computational analysis, with the GENSCAN exon prediction algorithm of Burge et al., of a 92,149 bp fragment (SEQ ID NO: 1) within the human 17q21 chromosomal locus revealed the presence of 15 putative exon sequences. *J. Mol. Biol.* 268:78-94 (1997). As presented in FIG. 1 and as discussed in detail in Example 3, 12 of these 15 exon fragments did not amplify from genomic DNA isolated from VBD-afflicted individuals.

In total, these results demonstrated for the first time the presence of a genomic deletion within human chromosome 17q21 that segregates absolutely with Van Buchem's disease. Furthermore, nucleotide sequencing of the region spanning the deletion breakpoint (SEQ ID NO:101) revealed that approximately 52 kb of contiguous genomic DNA is invariably deleted from chromosome 17 at position 17q21 in individuals afflicted with VBD. The sequence of the 52 kb region is presented herein as SEQ ID NO:2.

Isolated Polynucleotides

As noted above, the present invention provides isolated polynucleotides comprising at least 10, 15, 20, 25, 30, 40, 50, 100, 250, 500, 600, 700, 800 up to and including the 92,101 base pairs (bp) nucleotide sequence of human chromosome 17 at 17q21 disclosed herein as SEQ ID NO:1. Also provided by the present invention are isolated polynucleotides comprising at least 10, 15, 20, 25, 30, 40, 50, 100, 250, 500 bp up to and including the 52 kb sequence of 17q21 that is deleted in individuals who are either afflicted with or carriers of Van Buchem's disease (i.e. SEQ ID NO:2). As well, the present, invention provides polynucleotides comprising at least 10, 15, 20, 25, 30, 40, 50, 100, 250, 300, 350, 400, 450, 500, 550, 600, 650, 700, 750, 800, 850 or 890 bp of any of the exons depicted in SEQ ID NOs: 3-17. Other embodiments of the present invention provide oligonucleotide probes of at least 10, 15, 20, 25, 30, 40, 50, 100, 250, 500, 600, 750, 1000, 1050, 1100, 1200 or 1300 that hybridize under moderately stringent conditions to the nucleotide sequence of SEQ ID NO:1 or complements thereto. Exemplary oligonucleotide probes according to the present invention include those designated herein by SEQ ID NOs:28-100.

As used herein, the phrase "isolated polynucleotide" refers to a DNA molecule that has been isolated free of total genomic DNA of a particular species. As will be understood by those skilled in the art, the isolated polynucleotides of the present invention can include genomic sequences, extra-genomic and plasmid-encoded sequences and smaller engineered gene segments that express, or may be adapted to express, proteins, polypeptides, peptides and the like. Such segments may be naturally isolated, or synthesized de novo.

Thus, "isolated," as used herein, means that the polynucleotide is substantially separated away from other genomic sequences and that the polynucleotide does not contain large portions of unrelated coding DNA, such as large chromosomal fragments. Of course, this refers to the polynucleotide as originally isolated, and does not exclude genes or coding regions later added to the segment.

As will be recognized by the skilled artisan, isolated polynucleotides may be single-stranded or double-stranded, and may be DNA or RNA molecules. Additional coding or non-coding sequences may, but need not, be present within a polynucleotide of the present invention, and a polynucleotide may, but need not, be linked to other molecules and/or support materials.

It is also contemplated that the present invention encompasses polynucleotides having substantial identity to any of the sequences disclosed herein, for example the present invention encompasses those isolated polynucleotides comprising at least 50% or more sequence identity, preferably at least 55%, 60%, 65%, 70%, 75%, 80%, 85%, 90%, 95%, 96%, 97%, 98%, or 99% or higher, sequence identity compared to a polynucleotide sequence of this invention using the methods described herein, (e.g., BLAST, described in Altschul et al., *J. Mol. Biol.* 215:403-410 (1990)). For the purposes of this invention, a preferred method of calculating percent identity is the Smith-Waterman algorithm, using the following. Global DNA sequence identity must be at least 50% as determined by the Smith-Waterman homology search algorithm as implemented in MPSRCH program (Oxford Molecular) using an affine gap search with the following search parameters: gap open penalty, 12; and gap extension penalty, 1.

In additional embodiments, the present invention provides isolated polynucleotides comprising various lengths of contiguous stretches of sequence identical to or complementary to one or more of the sequences disclosed herein. For example, isolated polynucleotides are provided by this invention that comprise at least about 10, 15, 20, 25, 30, 40, 50, 100, 250, 500, 600, 750, 1000, 1050, 1100, 1200 or 1300 or more contiguous nucleotides of one or more of the sequences disclosed herein.

The polynucleotides of the present invention, or fragments thereof, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with to the total length preferably being limited by the ease of preparation and use in the intended recombinant DNA protocol.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides includes hybridization in a solution of 2×SSC, 0.1% SDS, 1.0 mM EDTA (pH 8.0) at 65° C.

In still other embodiments of the present invention, the polynucleotide sequences provided herein may be employed as primers in the amplification methodology disclosed herein, infra. As such, it is contemplated that polynucleotides comprising at least about 10 nucleotides that have the same sequence as, or that are complementary to, a 10 nucleotide long contiguous sequence disclosed herein will find utility as an amplification primer. Longer contiguous identical or complementary sequences, e.g., those of about 15, 20, 25, 30, 40, 50, 100, 250, 500, 600, 750, 1000, 1050, 1100, 1200 or 1300 or more will also be of use in certain embodiments.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology. See, e.g., Ausubel et al. (eds.), *Short Protocols in Molecular Biology* (3$^{rd}$ Ed., John Wiley & Sons 1995).

Methodologies for Detecting Van Buchem's Disease Carriers

As noted above, the present invention provides methods for detecting carriers of Van Buchem's disease. More specifically, within certain embodiments, these methods permit the differentiation between individuals who are homozygous for, and therefore afflicted with, VBD; individuals who are heterozygous for, and therefore carriers of, VBD; and individuals who are normal with respect to VBD. As described in detail herein, infra, the presently disclosed methodology will find general utility in the detection of a wide variety of diseases associated with genomic deletions of any length.

The methodology according to the present invention relies, in part, on the inability of various DNA polymerases that are typically utilized in amplification reactions to amplify DNA fragments beyond a maximum nucleotide length. As discussed above, the genomic locus associated with Van Buchem's disease is associated with a large chromosomal deletion of approximately 52 kb at 17q21. Consequently, this deletion results in the juxtapositon of nucleotide sequences present in the genomic DNA of non-VBD-afflicted individuals that are normally separated by greater than 52 kb. Because DNA polymerases normally utilized for the amplification of DNA fragments cannot amplify a 52 kb fragment, a pair of oligonucleotide primers that bind to nucleotide sequences upstream or downstream of this 52 kb region will not permit the amplification of DNA from a non-VBD-afflicted individual. In contrast, however, the same pair of oligonucleotide primers will facilitate the amplification of a DNA fragment from genomic DNA isolated from either a VBD-afflicted individual or from a VBD carrier.

The figures illustrate the genomic DNA corresponding to human chromosome 17 at 17q21 between the MEOX1 gene and exon 4. The genomic DNA from non-VBD-afflicted individuals comprises a 52 kb fragment described above while genomic DNA from VBD-afflicted individuals lack this 52 kb region. FIGS. 2 and 3 also illustrate exemplary oligonucleotide primers that hybridize to various regions within the 17q21 locus. Oligonucleotide primers designated VBspan2 and VBspan1/12953, and 12952 and VBspan1/12953 hybridize to nucleotide sequences, on complementary strands, that flank this 52 kb region in normal genomic DNA and, consequently, that flank the deletion breakpoint in genomic DNA from VBD-afflicted individuals. Because of the intervening 52 kb fragment in normal genomic DNA, neither the VBspan2/VBspan1 oligonucleotide primer pair nor the 12952/12953 oligonucleotide primer pair will permit the amplification (e.g., by PCR; see infra) of a DNA fragment from non-VBD-afflicted individuals. In contrast, the VBspan2/VBspan1 oligonucleotide pair primer will facilitate the amplification of a 642 bp fragment, and the 12952/12953 oligonucleotide pair primer will facilitate the amplification of a 798 bp fragment from the DNA of a VBD-afflicted individual.

The methodology according to the present invention additionally permits the differentiation between an individual who is heterozygous for the 52 kb genomic deletion and therefore a carrier of VBD; an individual who is homozygous for the 52 kb genomic deletion and therefore afflicted with VBD; and an individual who is neither a carrier of nor afflicted with VBD. This is achieved by the performance of a second amplification reaction employing a second pair of oligonucleotide primers wherein a third oligonucleotide primer hybridizes to a region of the genomic DNA flanking, either upstream or downstream of, the 52 kb sequence and a fourth oligonucleotide primer hybridizes to a region of the genomic DNA within the 52 kb sequence.

Alternatively, this can be performed using a single multiplex reaction employing a second pair of oligonucleotide primers wherein a third oligonucleotide primer hybridizes to a region of the genomic DNA within the 52 kb sequence and the other oligonucleotide primer is one of the primers from the first oligonucleotide primer pair. Such an oligonucleotide pair is exemplified in FIG. 3 by the VBspan2/VBint1 (SEQ ID NO:104/SEQ ID NO:105) oligonucleotide pair (SEQ ID NO:91/SEQ ID NO:92). As depicted in FIG. 3, a PCR reaction employing this oligonucleotide pair will amplify a 720 bp DNA fragment from the genomic DNA from an individual who is neither afflicted nor a VBD-carrier and from the genomic DNA of a heterozygous VBD-carrier but will not amplify a DNA fragment from the genomic DNA of a homozygous VBD-afflicted individual.

The methodologies according to the present invention permit an alternative approach to differentiating between an individual who is heterozygous for the 52 kb genomic deletion and therefore a carrier of VBD; an individual who is homozygous for the 52 kb genomic deletion and therefore afflicted with VBD; and an individual who is neither a carrier of nor afflicted with VBD, as described in Examples 4 and 5.

In Example 4, this can be achieved using at least two amplification reactions. In Example 5, this can be achieved by the performance of a single multiplex amplification reaction employing at least two oligonucleotide primer pairs, in which one oligonucleotide is common to both pairs. Thus the amplification reaction includes three oligonucleotide primers in total.

Thus, by the present invention provides two methodologies that permit the identification of VBD carriers by allowing the differentiation between an individual who is homozygous for the 52 kb genomic deletion and, therefore, afflicted with VBD; an individual who is heterozygous for the 52 kb genomic deletion and, therefore, a carrier for VBD; and an individual who is normal with respect to the 52 kb deletion and, therefore, neither a carrier of nor afflicted with VBD.

While the present invention discloses the nucleotide sequences of specific exemplary oligonucleotide primers that may be utilized according to the methodologies disclosed herein, it will be apparent to the skilled artisan that alternative oligonucleotide primers may be designed based on the nucleotide sequence depicted in SEQ ID NO:1 which primers are entirely within the scope of the present invention. Thus, for example, suitable oligonucleotide primers according to the present invention include polynucleotides comprising at least 10, 15, 20, 25, 30, 40, 50, 60, 75, 90 or 10.0 contiguous nucleotides of the nucleic acid depicted in SEQ ID NO:1.

It will also be apparent to one skilled in the art that the choice of reaction conditions and DNA polymerases employed for performing the amplification reactions may be varied in accordance with such parameters as the nucleotide sequence of the oligonucleotide primers and the distance between the primer pairs. Exemplary conditions for 25 ul reactions according to the present methodologies include, but are not limited to, the following: 10 ng genomic DNA; 60 mM TrisHCl pH 7.5; 15 mM ammonium sulfate; 2.5 mM magnesium chloride; 0.4 mM dNTP; and 0.2 uM of each oligonucleotide primer. A typical amplification protocol involves an initial denaturation at 94° C. for 3 min.; 40 cycles of 94° C. for 1 min., 68° C. for 1 min. and 72° C. for 1 min.; and a final extension reaction at 72° C. for 5 min. Amplicons may be resolved by electrophoresis on a 1% agarose gel run in 1×TAE buffer and may be detected by staining with ethidium bromide. Further exemplary conditions for 50 µl reactions according to the present methodologies include, but are not limited to, the following: 20 ng genomic DNA, 0.4 µM each of VBspan1 and VBint1, 0.8 µM of VBspan2, 0.2 mM of each dNTP, 120 mM TrisHCl, pH 7.5, 30 mM ammonium sulfate, 5.0 mM magnesium chloride and 2.5 U Taq polymerase (Roche Molecular Biochemicals, Indianapolis, Ind.). A further typical amplification protocol involves an initial denaturation at 94° C. for 3 min, 40 cycles of 94° C. for 30 sec, 63° C. for 30 sec, 72° C. for 2 min and a final extension of 72° C. for 5 min. Amplicons may be resolved by electrophoresis on a 2.5% agarose gel run in 1×TAE buffer and may be detected by staining with ethidium bromide.

Genomic DNA may be isolated by standard procedures that are readily available to those of skill in the art. Representative methodology are provided, for example, in Sambrook et al., *Molecular Cloning: A Laboratory Manual* (Cold Spring Harbor Laboratories, Cold Spring Harbor, N.Y., 1989) and in Ausubel et al. (eds), *Short Protocols in Molecular Biology* (4$^{th}$ Ed., John Wiley & Sons 1999).

General methodology for performing the polymerase chain reaction (PCR™) are described in detail in U.S. Pat. Nos. 4,683,195; 4,683,202 and 4,800,159, each of which is incorporated herein by reference in its entirety. Briefly, in PCR™, two primers are prepared which have sequences that are complementary to regions on opposite complementary strands of the target sequence. An excess of deoxynucleoside triphosphates is added to a reaction mixture along with a DNA polymerase (e.g., Taq polymerase; see, infra, for exemplary alternative polymerases). If the target sequence is present in a sample, the primers will bind to the target and the polymerase will cause the primers to be extended along the target sequence by adding on nucleotides. By raising and lowering the temperature of the reaction mixture, as indicated, indicated, supra, the extended primers will dissociate from the target to form reaction products, excess primers will bind to the target and to the reaction product and the process is repeated.

In addition to the polymerase chain reaction, it is contemplated that alternative amplification procedures that are readily available in the art may be employed in the methodology disclosed herein. For example, another suitable method for amplification is the ligase chain reaction (LCR) and is disclosed in Eur. Pat. Appl. Publ. No. 320,308 (incorporated herein by reference). Briefly, in LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. For a related technique, see also, U.S. Pat. No. 4,883,750, incorporated herein by reference in its entirety.

Alternatively, other methods may be similarly employed in place of the polymerase chain reaction for amplification of nucleic acid sequences include the following: (1) Qbeta Replicase, PCT Intl. Pat. Appl. Publ. No. PCT/US87/00880; (2) the isothermal amplification method of Walker et al.; (3) strand displacement amplification (SDA); (4) repair chain reaction (RCR); (5) cyclic probe reaction (CPR); see, also, Great Britain Pat. Appl. No. 2 202 328, and in PCT Intl. Pat. Appl. Publ. No. PCT/US89/01025; (7) transcription-based amplification systems (TAS) Kwoh et al., 1989; PCT Intl. Pat. Appl. Publ. No. WO 88/10315; (8) Eur. Pat. Appl. Publ. No. 329,822; (9) PCT Intl. Pat. Appl. Publ. No. WO 89/06700; (10) "RACE" (Frohman, 1990); (11) "one-sided PCR" (Ohara, 1989). Each of these methods is incorporated herein by reference.

The choice of DNA polymerase to be employed in the polymerase chain or other amplification reaction can also be determined by the skilled artisan without undue experimentation. As discussed above, the major consideration in selecting an appropriate polymerase is the maximum length of DNA fragment that may be amplified. Such a determination may be achieved initially by reference to the guidelines set forth by the individual manufacturers and ultimately through empirical means by testing stepwise increases in the length of DNA fragment amplified. Additionally or alternatively, the precise reaction condition parameters such as, for example, salt concentration, divalent cation employed and reaction temperature may all be varied in order to adjust, as desired, the length of DNA fragment that may be amplified. The determination of optimal reaction parameters is wholly within the expertise of the skilled artisan.

Exemplary polymerases that may be employed in the present methodology include the various DNA polymerases, and variants thereof, isolated from thermostable bacteria such as the following: Taq, Vent and Deep Vent DNA polymerases (New England BioLabs; Beverly, Mass.); AdvanTaq™, AdvanTaq Plus™, and Advantage$^R$ 2 (Clontech; Palo Alto, Calif.); SuperTaq (Ambion; Austin, Tex.); Tth and Pwo polymerases (Roche Molecular Biochemicals; Indianapolis, Ind.); AmpliTaq (PE Biosystems; Foster City, Calif.); and Taq2000 and Pfu DNA polylmerases (Stratagene; La Jolla, Calif.).

General Methods for Detection of Large Genomic Deletions

The methodology disclosed herein, supra, for the detection of the large genomic deletion associated with Van Buchem's disease and carriers thereof may be applied broadly, and therefore will find general utility, in the detection of a wide variety of diseases associated with large genomic deletions. In short, the present methods take advantage of the inability of commonly available DNA polymerases to amplify nucleic acid fragments above a certain maximum size when employed in a polymerase chain or other amplification reaction.

Thus, as noted above, the present invention provides general methodologies for distinguishing between an individual who is homozygous for a large genomic deletion, an individual who is heterozygous for a large genomic deletion and an individual who is negative for a large genomic deletion. These methods are discussed in detail in Examples 4 and 5.

As used herein, the phrase "large genomic deletion" refers to those deletions that result from the loss of a contiguous stretch of genomic DNA of such a length that it cannot be amplified in an amplification reaction as disclosed herein, supra. One skilled in the art will recognize, therefore, that the phrase "large genomic deletion" will vary depending on the precise reaction conditions and DNA polymerases employed in the amplification reactions. Generally, the phrase "large genomic deletion" may refer to deletions of at least 2 contiguous kilobases (kb) of genomic DNA. Alternatively, a "large genomic deletion" refers to deletions of at least 3, 4, 5, 6, 7, 8, 9, 10 or more contiguous kb of genomic DNA. Also included within the definition of "large genomic deletions" are deletions of at least 15, 20, 25, 30, 40 or 50 contiguous kb of genomic DNA.

The ASCII text file, containing 224,000 bytes, with file name "12870568_CORRECTED_SEQUENCE_LISTING.txt," created Apr. 14, 2011, is incorporated by reference herein in its entirety.

EXAMPLES

The following experimental examples are offered by way of illustration, not limitation.

Example 1

The Van Buchem'S Disease Locus Localizes to a Region of Less than 1 Mb

This example discloses that haplotype analysis of a number of Van Buchem's Disease patients carrying recombinant chromosomes localized the disease to a critical region of less than 1 Mb in a region between the polymorphic markers BP12574 (D17S2250) and JM6307 (D17S2253).

The Van Buchem's Disease region was previously localized to the ~1 cM interval between polymorphic markers D17S1787 and D17S1861 on chromosome 17q12-21. To refine the interval further, genomic DNA samples were obtained from 15 affected individuals, 4 of whom had not been previously analyzed. A number of microsatellite markers from chromosome 17q12-21 were used to analyze the DNA samples. Patient DNA samples were genotyped using PCR amplification of polymorphic microsatellite markers. The microsatellite markers selected (see Table 1) are described in public databases or were developed using the SPUTNIK algorithm on sequence obtained from a BAC contig across the van Buchem disease/sclerosteosis region (Brunkow et al., *Am. J. Hum. Genet.* 68:577-584 (2001)), D17S1787 to D17S1861. PCR products were labeled with infrared IRDyes™ using an M13 tailing approach as described in Oetting et al., *Genomics* 30:450-458 (1995) and were resolved on a LiCor 4000 DNA sequencer. Allele determinations were made using the SAGA genotyping analysis software (University of Washington) or by a trained eye.

Using this large set of novel polymorphic markers derived from a BAC contig across the D17S1787 and D17S1861 interval, a large region of homozygosity across the disease locus was observed. Furthermore, all affected individuals (including 12-15) shared a common disease haplotype (Table 1). Individuals 2, 3, 6-8 and 12-15 were nonrecombinant across the entire D17S1787-D17S1861 interval, while individuals 1, 4, 5 and 9, 10, 11 carried recombinant chromosomes. Accordingly, the disease locus was refined to the <1 Mb region between BP12574 (D17S2250) and JM6307 (D17S2253) (see Table 1).

TABLE 1

Marker genotypes of affected individuals for selected markers at the van Buchem disease locus on chromosome 17q12-q21

| MARKER | DUTCH VAN BUCHEM DISEASE GENOTYPES AFFECTED INDIVIDUAL | | | | | | CONSENSUS VBD HAPLOTYPE | CONSENSUS SCLEROSTEOSIS HAPLOTYPE |
| --- | --- | --- | --- | --- | --- | --- | --- | --- |
| | 1 | 4 | 5 | 9 | 10 | 11 | (DUTCH) | (AFRIKANER) |
| D17S1787 | 4 4 | 4 4 | 4 4 | 4 8 | 4 8 | 4 8 | 4 | 1 |
| D17S2231 | 4 4 | 4 4 | 4 4 | 4 11 | 4 11 | 4 11 | 4 | 6 |
| D17S1793 | 4 4 | 4 4 | 4 4 | 4 7 | 4 7 | 4 7 | 4 | 4 |
| BP7060 | 11 11 | 11 11 | 11 11 | 11 12 | 11 12 | 11 12 | 11 | 11 |
| BP7872 | 2 2 | 2 2 | 2 2 | 2 3 | 2 3 | 2 3 | 2 | 2 |
| D17S855 | 6 6 | 6 6 | 6 6 | 6 8 | 6 8 | 6 8 | 6 | 7 |
| BP12568 | 1 1 | 1 1 | 1 1 | 1 3 | 1 3 | 1 3 | 1 | ND |
| BP12574 (D17S2250) | 3 3 | 3 3 | 3 3 | 1 3 | 1 3 | 1 3 | 3 | ND |
| BP12578 | 2 2 | 2 2 | 2 2 | 2 2 | 2 2 | 2 2 | 2 | ND |
| BP6991 | 3 3 | 3 3 | 3 3 | 3 3 | 3 3 | 3 3 | 3 | 3 |
| D17S1789 | Δ | Δ | Δ | Δ | Δ | Δ | Δ | 8 |
| D17S951 | 1 1 | 1 1 | 1 1 | 1 1 | 1 1 | 1 1 | 1 | 3 |
| SOST | C | C | C | C | C | C | C | T |
| JM6307 (D17S2253) | 1 7 | 1 1 | 1 1 | 1 1 | 1 1 | 1 1 | 1 | 4 |
| D17S2234 | 2 1 | 2 2 | 2 2 | 2 2 | 2 2 | 2 2 | 2 | 2 |
| D17S1860 | 7 11 | 7 7 | 7 7 | 7 7 | 7 7 | 7 7 | 7 | 10 |
| BP7129 | 2 6 | 2 2 | 2 2 | 2 2 | 2 2 | 2 2 | 2 | 4 |
| BP7141 | 10 1 | 10 1 | 10 1 | 10 10 | 10 10 | 10 10 | 10 | 8 |
| D17S2235 | 3 1 | 3 1 | 3 1 | 3 3 | 3 3 | 3 3 | 3 | 3 |
| D17S1861 | 8 13 | 8 2 | 8 2 | 8 8 | 8 8 | 8 8 | 8 | 8 |

Example 2

Sclerosteosis and Van Buchem'S Haplotypes are Distinct

To determine whether the Dutch van Buchem disease haplotype was related directly to the disease haplotype found in Afrikaner individuals affected with sclerosteosis, sclerosteosis DNA samples were typed with the same set of markers described in Example 1. These were then directly compared to the van Buchem disease DNA samples. The analysis showed marked differences between the two disease haplotypes (Table 1). In instances where the two disease chromosomes carried identical alleles at adjacent markers, true identity by descent (IBD) was unlikely, due either to the fact that one or the other shared allele was found at a high frequency (>0.50) in normal unaffected controls (not shown), or to the close spacing (i.e., <50 kb) between the markers. Finally, the van Buchem disease samples were typed for a single nucleotide polymorphism (SNP) specific for the Afrikaner SOST gene mutation. It was found that they all carried the normal "C" allele. These results indicate that van Buchem disease haplotype is distinct from sclerosteosis haplotype.

Example 3

Van Buchem'S Disease is Caused by a Specific Chromosomal Deletion that Represents a Unique Identifier for the Disease Chromosome This example discloses that patients afflicted with VBD have a chromosomal deletion of approximately 52 kb that is correlative of the disease phenotype.

Characterization of all the candidate genes within the 1 Mb region between polymorphic markers BP12574 (D17S2250) and JM6307 (D17S2253) revealed a specific chromosomal aberration that segregated absolutely with Van Buchem's disease. Two independent experimental approaches to identifying the VBD candidate region revealed the presence of a chromosomal deletion associated with VBD.

First, a publicly available oligonucleotide primer pair (i.e. the SSLP designated D17S1789; see FIG. 1A and Table 5) failed to PCR amplify a DNA fragment from genomic DNA obtained from VBD patients while permitting the amplification of a DNA fragment from genomic DNA obtained from normal individuals. As part of the present invention, the nucleotide sequence of a 92,101 bp stretch of genomic DNA from a normal individual, encompassing the D17S1789 amplified fragment, was obtained and is presented herein as SEQ ID NO:1.

Second, the 92 kb stretch of DNA was computationally analyzed, using the GENSCAN exon prediction algorithm, to identify putative exon sequences (Burge et al., *J. Mol. Biol.* 268:78-94 (1997)). PCR primer pairs corresponding to sequences flanking each exon were designed and tested in amplification reactions using as template the genomic DNA obtained from non-VBD-afflicted individuals and individuals afflicted with VBD.

FIG. 1A discloses the normal exon structure across the relevant chromosomal region between the Mox1 and SOST genes, as predicted by the GENSCAN exon prediction algorithm. Exons that amplified from both VBD and normal DNAs are indicated by the filled blocks (i.e. 1-4 and 26-28) while exons that failed to amplify from VBD DNA are indicated by the open blocks (i.e. 9-19). The location of the amplicons that include these exon sequences within the 92 kb nucleic acid of SEQ ID NO:1 and the respective SEQ ID NO assigned to each of the exon sequences as provided by the present invention are indicated in Table 2. The results of these amplification reactions using genomic DNA from VBD afflicted and nonafflicted individuals is summarized in Table 4.

TABLE 2

Amplicons Spanning Potential Exons Predicted by GENSCAN

| Amplicon Name | Amplicon # | Primers (DMO#) | Location in SEQ ID NO: 1 | SEQ ID NO |
|---|---|---|---|---|
| Gscn12.210A.09 | 19 | 12098/12104 | 14021-13436 | SEQ ID NO: 17 |
| Gscn12.210A.8 | 18 | 12097/12103 | 18353-17837 | SEQ ID NO: 16 |
| Gscn12.210A.7 | 17 | 12090/12096 | 18903-18334 | SEQ ID NO: 15 |
| Gscn12.210A.6 | 16 | 12089/12095 | 19556-18884 | SEQ ID NO: 14 |
| Gscn12.210A.5 | 15 | 12088/12094 | 19593-19063 | SEQ ID NO: 13 |
| Gscn12.210A.4 | 14 | 12087/12093 | 29498-28949 | SEQ ID NO: 12 |
| Gscn12.210A.3 | 13 | 12086/12092 | 33353-32666 | SEQ ID NO: 11 |
| Gscn12.210A.2 | 12 | 12085/12091 | 35036-34373 | SEQ ID NO: 10 |
| Gscn12.210A.1 | 11 | 12078/12084 | 36817-36212 | SEQ ID NO: 9 |
| Gscn12.668.08 | 10 | 12110/12116 | 49386-49957 | SEQ ID NO: 8 |
| Gscn12.668.07 | 9 | 12109/12115 | 50550-51151 | SEQ ID NO: 7 |
| Gscn12.668.06 | 4 | 9260/9261 | 58974-58394 | SEQ ID NO: 6 |
| Gscn12.668.05 | 3 | 12709/12710 | 58922-59740 | SEQ ID NO: 5 |
| Gscn12.668.04 | 2 | 12101/12107 | 67161-67717 | SEQ ID NO: 4 |
| Gscn12.668.03 | 1 | 12100/12106 | 75612-76103 | SEQ ID NO: 3 |

In total, 16 fragments, corresponding to the SSLP (D17S1789) and at least 15 potential coding exons, were successfully amplified from genomic DNA obtained from non-VBD-afflicted individuals. In contrast, 12 of these 16 fragments did not amplify from genomic DNA obtained from individuals afflicted with VBD. These results revealed the presence of, and partially localized, a genomic deletion within human chromosome 17q21 in the locus associated with VBD (see FIG. 1A).

To better define the endpoints of this chromosomal deletion, additional PCR amplification reactions were performed with primers designed to amplify within the presumably non-coding regions located between the exons at either end of the VBD-specific deletion. The PCR primer pairs used and results obtained are summarized in Tables 3 and 4.

TABLE 3

Amplicons Corresponding to Non-coding Sequences Located within SEQ ID NO: 1

| Amplicon Name | Amplicon # | Primers (DMO#) | Location in SEQ ID NO: 1 | SEQ ID NO |
|---|---|---|---|---|
| 5'moxA | 25 | 12697/12698 | 1499-1018 | SEQ ID NO: 27 |
| 5'moxB | 24 | 12699/12700 | 2524-2065 | SEQ ID NO: 26 |
| 5'moxC | 23 | 12701/12702 | 5608-4939 | SEQ ID NO: 25 |

TABLE 3-continued

Amplicons Corresponding to Non-coding Sequences Located within SEQ ID NO: 1

| Amplicon Name | Amplicon # | Primers (DMO#) | Location in SEQ ID NO: 1 | SEQ ID NO |
|---|---|---|---|---|
| 5'moxD | 22 | 12703/12704 | 8684-8249 | SEQ ID NO: 24 |
| 5'moxE | 21 | 12705/12706 | 11248-10880 | SEQ ID NO: 23 |
| D17S1789 | 20 | 1789for/rev | 14257-14060 | SEQ ID NO: 22 |
| 668intronD | 8 | 12622/12623 | 51371-52377 | SEQ ID NO: 21 |
| 668intronC | 7 | 12624/12625 | 53062-54232 | SEQ ID NO: 20 |
| 668intronB | 6 | 12626/12627 | 55163-56398 | SEQ ID NO: 19 |
| 668intronA | 5 | 12628/12629 | 57103-58202 | SEQ ID NO: 18 |

The deletion associated with VBD was further characterized by amplifying a fragment from VBD genomic DNA, using the PCR primer pair 9260/12702 (SEQ ID NO:30/SEQ ID NO:77), sub-cloning this fragment and sequencing it to completion. As disclosed in FIG. 2, the 9260/12702 primer pair spans the deletion identified in VBD afflicted individuals. The 2317 bp fragment obtained from PCR amplification comprised a deletion breakpoint flanked on both the 5' and 3' ends with normal genomic DNA sequences. Without being limited to any particular theory of the present invention, it is believed that these results indicate that the VBD aberration is a simple chromosomal deletion, with no other associated rearrangements. The nucleotide sequence spanning the deletion breakpoint is depicted in FIG. 1B and is provided in SEQ ID NO:101.

Comparison of the SEQ ID NO:101 with the 92,149 bp sequence obtained from non-VBD-afflicted individuals revealed that approximately 52 kb of contiguous genomic DNA is invariably deleted from chromosome 17 at position 17q21 in individuals afflicted with Van Buchem's disease. This deletion is not present in individuals who are non-carriers or not afflicted with Van Buchem's disease. The sequence of the 52 kb sequence is provided in SEQ ID NO:2.

TABLE 4

Amplification Results Obtained from VBD Affected and Unaffected Genomic DNA Samples

| Amplicon Name | Amplicon # | Primers (DMO#) | PCR Results VBD Affected | PCR Results Unaffected |
|---|---|---|---|---|
| Mox1.03 | 28 | 12158/12164 | + | + |
| Mox1.02 | 27 | 12157/12163 | + | + |
| Mox1.01 | 26 | 12265/12156 | + | + |
| 5'moxA | 25 | 12697/12698 | + | + |
| 5'moxB | 24 | 12699/12700 | + | + |
| 5'moxC | 23 | 12701/12702 | + | + |
| 5'moxD | 22 | 12703/12704 | − | + |
| 5'moxE | 21 | 12705/12706 | − | + |
| D17S1789 | 20 | 1789for/rev | − | + |
| gscn12.210A.09 | 19 | 12098/12104 | − | + |
| gscn12.210A.8 | 18 | 12097/12103 | − | + |
| gscn12.210A.7 | 17 | 12090/12096 | − | + |
| gscn12.210A.6 | 16 | 12089/12095 | − | + |
| gscn12.210A.5 | 15 | 12088/12094 | − | + |
| gscn12.210A.4 | 14 | 12087/12093 | − | + |
| gscn12.210A.3 | 13 | 12086/12092 | − | + |
| gscn12.210A.2 | 12 | 12085/12091 | − | + |
| gscn12.210A.1 | 11 | 12078/12084 | − | + |
| gscn12.668.08 | 10 | 12110/12116 | − | + |
| gscn12.668.07 | 9 | 12109/12115 | − | + |
| 668intronD | 8 | 12622/12623 | − | + |
| 668intronC | 7 | 12624/12625 | − | + |
| 668intronB | 6 | 12626/12627 | − | + |
| 668intronA | 5 | 12628/12629 | − | + |
| gscn12.668.06 | 4 | 9260/9261 | + | + |
| gscn12.668.05 | 3 | 12709/12710 | + | + |
| gscn12.668.04 | 2 | 12101/12107 | + | + |
| gscn12.668.03 | 1 | 12100/12106 | + | + |

TABLE 5

Polynucleotide Sequences Derived from SEQ ID NO: 1

| Primer Name | Nucleotide Sequence (5'-3') | SEQ ID NO |
|---|---|---|
| 1789for (5522) | ATTGGCCTGGCTTCTG | SEQ ID NO: 28 |
| 1789rev (5524) | GGCTGGAGCAGGGACT | SEQ ID NO: 29 |
| 9260 | TCCTGTGATCGCATTGAGAC | SEQ ID NO: 30 |
| 9261 | CCCTGCCATTCTGGATAGTTT | SEQ ID NO: 31 |
| 12078 | CAGTGGCTTTATTTTCCTAA | SEQ ID NO: 32 |
| 12084 | GAAGCTTCTCCATGTTCTTA | SEQ ID NO: 33 |
| 12085 | GTCTAAAAATGAAGAAGGCA | SEQ ID NO: 34 |
| 12086 | TTAAGTGACTTGTCCGAGAT | SEQ ID NO: 35 |
| 12087 | CAACTCAATCTTTTGGTGTT | SEQ ID NO: 36 |
| 12088 | AAATCAGATTCAAGCAGTGT | SEQ ID NO: 37 |
| 12089 | TCTTAACTGGCTTTTCAGAC | SEQ ID NO: 38 |
| 12090 | ATTGTTTCATTTTACCCTCA | SEQ ID NO: 39 |
| 12091 | GCCATAAAATCAGGATAATG | SEQ ID NO: 40 |
| 12092 | TGCCTAGAACATTCTGGTAT | SEQ ID NO: 41 |
| 12093 | CAAAGTGGCTCTGATTATTT | SEQ ID NO: 42 |
| 12094 | GGATCTCCTACGTACTGCTA | SEQ ID NO: 43 |
| 12095 | TGAGGGTAAAATGAAACAAT | SEQ ID NO: 44 |
| 12096 | AAAGACACTGCAGAGAAAAG | SEQ ID NO: 45 |
| 12097 | CTTTTCTCTGCAGTGTCTTT | SEQ ID NO: 46 |
| 12098 | GAGACCTCTCCTCTTTGAAT | SEQ ID NO: 47 |
| 12100 | GGTTTCAACTAGTTCTGGTG | SEQ ID NO: 48 |
| 12101 | CTAGGGCTTAGAAGTTTCCT | SEQ ID NO: 49 |
| 12103 | ACTCCTAGAACCCTAAAGGA | SEQ ID NO: 50 |
| 12104 | GTATCACCAGTGAAGTTGGT | SEQ ID NO: 51 |
| 12106 | GATAAATGGATATGGCAAAG | SEQ ID NO: 52 |
| 12107 | GGTTTATAATTTGCAACCAG | SEQ ID NO: 53 |
| 12109 | ATTCCCTAAGAGATTTGTCC | SEQ ID NO: 54 |

TABLE 5-continued

Polynucleotide Sequences Derived from SEQ ID NO: 1

| Primer Name | Nucleotide Sequence (5'-3') | SEQ ID NO |
|---|---|---|
| 12110 | GAGAGGACAAACATTCAAAC | SEQ ID NO: 55 |
| 12115 | TTTAGACCTATCACTCCCAA | SEQ ID NO: 56 |
| 12116 | CTACTGGGACAAACCATTAC | SEQ ID NO: 57 |
| 12156 | AGAGAGGGTGAGTAACTTCC | SEQ ID NO: 58 |
| 12157 | AATAAAAGAAAGTTTGGGGT | SEQ ID NO: 59 |
| 12158 | GCAGAGTGCTTTTAGAACAT | SEQ ID NO: 60 |
| 12163 | AGGTGGAGGTTACAGTAAGA | SEQ ID NO: 61 |
| 12164 | AAGCAGTATCTCTGAAGCTG | SEQ ID NO: 62 |
| 12265 | CCTTTTCTTGGTTCAGATAA | SEQ ID NO: 63 |
| 12622 | ACGGTGTACACATTTGGTTAG | SEQ ID NO: 64 |
| 12623 | CGGATATTTGTCTGTGATACG | SEQ ID NO: 65 |
| 12624 | ACCGTGCAGAGGTAGATGGTA | SEQ ID NO: 66 |
| 12625 | CCAGTGGAAGAGACAGGTGA | SEQ ID NO: 67 |
| 12626 | GAGCTGAGATCGCACCACTT | SEQ ID NO: 68 |
| 12627 | CAACACGACATGGAATGGACT | SEQ ID NO: 69 |
| 12628 | CACAGCTGGAGACATGTTACA | SEQ ID NO: 70 |
| 12629 | AGGGTTCACACCATATCAGAA | SEQ ID NO: 71 |
| 12697 | ACGCTGCTGTTAAGGTCCA | SEQ ID NO: 72 |
| 12698 | TGCCAATTAGCCACACTCTTC | SEQ ID NO: 73 |
| 12699 | GTGCAAAGTGCCTTACACAG | SEQ ID NO: 74 |
| 12700 | GAGGTTAGACGGGTCTGAGTT | SEQ ID NO: 75 |
| 12701 | TGGCAGGCAGTAGTAACTCTG | SEQ ID NO: 76 |
| 12702 | CTGGGATTACAGGTGTCTGG | SEQ ID NO: 77 |
| 12703 | TGAGCTGTTCCCACACCACAT | SEQ ID NO: 78 |
| 12704 | TCAGGACGTTGCACTTTGACA | SEQ ID NO: 79 |
| 12705 | GAATGCTGGATGTGGATTGAG | SEQ ID NO: 80 |
| 12706 | GAGCAGAAGGCCTTGACTGA | SEQ ID NO: 81 |
| 12709 | GCCTTCAGTTTGTCCCGTTCT | SEQ ID NO: 82 |
| 12710 | CGCGAGGTCAGGAGTTCGAT | SEQ ID NO: 83 |
| 12952 | CCACTGAACAGGGCACAAGAT | SEQ ID NO: 84 |
| VBspan1/ 12953 | GAATTACTGGCTGAGGCAACC | SEQ ID NO: 85 |
| Span1F | GCCTGCGCTTACATAGT | SEQ ID NO: 86 |
| Span1R | AGGCGGGCGGATCACAAGGTC | SEQ ID NO: 87 |
| Span2F | GGCTCACTGCAACCTCCACCTA | SEQ ID NO: 88 |
| Span2R | AACCAAACAAGCCAGCAATCACTC | SEQ ID NO: 89 |
| Wt1R | TGGGAGGCTGAGGCAAGAGAT | SEQ ID NO: 90 |
| Wt2F | ACTGGGCCTGGGATGTAT | SEQ ID NO: 91 |
| Wt2R | AAAAATTGGCTGGGTGTGG | SEQ ID NO: 92 |
| Wt3F | CAGGCTGGAGTGCAATGGTGTG | SEQ ID NO: 93 |
| Wt3R | TGGGAGGCTGAGGCAAGAGAAT | SEQ ID NO: 94 |
| Del1F | CTCACTGCAGCCTCAACTCG | SEQ ID NO: 95 |
| Del1R | TAGCAGAAGGGGGAAGGGGAACG | SEQ ID NO: 96 |
| Del2F | GACGGTGTACACATTTGGTTAGTT | SEQ ID NO: 97 |
| Del2R | GCACAGTTACATCCGCCTTATCGT | SEQ ID NO: 98 |
| Del3F | TGCAGACACCCAGAGAAGACGACT | SEQ ID NO: 99 |
| Del3R | TGGACCCTGCCCTCACGATGGA | SEQ ID NO: 100 |
| VBspan2 | TACTACTGGGCCTGGGATGTA | SEQ ID NO: 104 |
| VBint1 | TAGAGAAAGACCTCGTTATTGG | SEQ ID NO: 105 |

Example 4

First Methodology for Identification of Van Buchem'S Disease Carriers by Detection of a 52 Kb Genomic Deletion This example discloses a methodology for distinguishing individuals who are afflicted with or carriers of Van Buchem's disease as well as from individuals to who are normal with respect to the 52 kb deletion. The methodology is based on the observation that the large, i.e. 52 kb genomic deletion that correlates absolutely with Van Buchem's disease may be identified by amplification of the region encompassing the deletion breakpoint.

The deletion on the Van Buchem's disease chromosomal locus 17q21 results in the apposition of DNA sequences normally separated by approximately 52 kb. A PCR assay specific for the deleted chromosome was developed. Starting with the sequence of the 2.3 kb VBD-specific fragment that includes the deletion endpoints, primers were designed to span the endpoints and yield a 400-800 bp amplicon from VBD DNA but would not, because of the presence of the 52 kb genomic fragment, permit the amplification of any fragment from normal, non-carrier genomic DNA samples.

As illustrated in FIG. 2, the following oligonucleotide primer pairs were used to amplify chromosomal DNA within the locus 17q21 from individuals who are afflicted with or carriers of VBD: Primer Nos. 12952 and 12953 hybridize within the region upstream and downstream, respectively, of the 52 kb genomic region deleted in VBD-afflicted individuals and amplify a 798 bp fragment when the 52 kb region is deleted; Primer Nos. Wt2F and Wt2R hybridize upstream of and within, respectively, the 52 kb genomic region deleted in VBD-afflicted individuals and amplify a 473 bp fragment in the absence of the deletion; Primer Nos. 9261 and 9260 hybridize within the region downstream of the 52 kb genomic region deleted in VBD-afflicted individuals and amplify a 581 bp fragment in all cases.

The VBD diagnostic was designed such that individuals who are homozygous for the 52 kb deletion and therefore afflicted with VBD may be differentiated from individuals who are heterozygous for the 52 kb deletion and therefore carriers of VBD as well as individuals who are normal with respect to the 52 kb deletion. Two separate PCR reactions were performed on the individual to be tested. In the first, a primer pair spanning upstream and within the VBD deletion (i.e. the Wt2F/Wt2R oligonucleotide primer pair) yielded an amplicon from normal non-carriers and heterozygous carriers. In the second reaction, primers which span the 52 kb deletion (i.e. the 12952/12953 oligonucleotide primer pair) yielded an amplicon from heterozygous VBD carriers and homozygous patients. A primer pair spanning a region unaffected by the 52 kb genomic deletion (i.e. the 9260/9261 oligonucleotide primer pair) was included as a positive control for the PCR reactions.

The following reaction conditions were used for amplification of 400 to 800 bp nucleic acid fragments using as template genomic DNA isolated from patients who are afflicted with or carriers of Van Buchem's disease: 25 ul reactions included 10 ng genomic DNA; 60 mM TrisHCl, pH 7.5; 15 mM Ammonium Sulfate; 2.5 mM Magnesium Chloride; 0.4 mM each of dATP, dCTP, dGTP and dTTP; 0.2 µM each of Primer Nos. Wt2F and Wt2R, or 12952 and 12953, or 9260 and 9261. The fragments (473, 798, and 581 bp, respectively) were amplified by the following protocol: Denaturation at 94° C. for 3; 40 cycles of 94° C. for 1 minute, 68° C. for 1 minute and 72° C. for 1 minute; final extension at 72° C. for 5 minutes. The amplified nucleic acid fragments were resolved on a 1% agarose gel using 1×TAE buffer. DNA bands were visualized with ethidium bromide staining.

The results are summarized in FIG. 2. The summary shows that nucleic acid fragments amplified in all PCR reactions containing the 9260/9261 oligonucleotide primer pair regardless of the source of genomic DNA template. The 12952/001 oligonucleotide primer pair amplified a nucleic acid fragment from non-VBD afflicted individuals and individuals who are heterozygous for and therefore carriers of VBD but did not amplify a nucleic acid fragment from individuals who are homozygous for and therefore afflicted with VBD. The 12952/12953 oligonucleotide primer pair amplified a nucleic acid fragment from individuals who are heterozygous for and therefore carriers of VBD and from individuals who are homozygous for and therefore afflicted with VBD but did not amplify a nucleic acid fragment from non-VBD afflicted individuals.

These results demonstrated that a first methodology presented herein permit the differentiation between an individual who is homozygous for the 52 kb genomic deletion and therefore afflicted with VBD, an individual who is heterozygous for the 52 kb genomic deletion and therefore a carrier of VBD and an individual who does not bear the 52 kb genomic deletion and is therefore normal with respect to VBD.

Example 5

Second Methodology for Identification of Van Buchem'S Disease Carriers by Detection of a 52 Kb Genomic Deletion This example discloses a second methodology for identifying individuals who are afflicted with or carriers of Van Buchem's disease as well as from individuals who are normal with respect to the 52 kb deletion. The methodology is based on the observation that the large, i.e. 52 kb genomic deletion that correlates absolutely with Van Buchem's disease may be identified by amplification of the region encompassing the deletion breakpoint.

As illustrated in FIG. 3, the following oligonucleotide primer pairs were used to amplify chromosomal DNA within the locus 17q21 from individuals who are afflicted with or carriers of VBD: Primers VBspan2 and VBspan1 hybridize upstream and downstream, respectively, to a region that flanks the 52 kb genomic region deleted in VBD-afflicted individuals and amplify a 642 bp fragment when the 52 kb region is deleted. Primer VBint hybridizes within the 52 kb genomic region which is deleted in VBD-afflicted individuals and with primer VBspan2 amplify a 720 bp fragment in the absence of the deletion.

The VBD diagnostic was designed such that individuals who are homozygous for the 52 kb deletion and therefore afflicted with VBD may be differentiated from individuals who are heterozygous for the 52 kb deletion and therefore carriers of VBD as well as individuals who are normal with respect to the 52 kb deletion.

A single multiplexed PCR reaction was performed on the individual to be tested. The pair of oligonucleotide primers span the 52 kb deletion (i.e. the VBspan1/VBspan2 oligonucleotide primer pair) yielded an amplicon from heterozygous VBD carriers and homozygous patients. The second pair of oligonucleotide primers pair spanning upstream and within the VBD deletion (i.e. the VBspan2/VBint1 oligonucleotide primer pair) yielded an amplicon from normal non-carriers and heterozygous carriers. A primer pair spanning a region unaffected by the 52 kb genomic deletion (i.e. the 9260/9261 oligonucleotide primer pair) was included as a positive control for the PCR reactions.

The following reaction conditions were used for amplification of 400 to 800 bp nucleic acid fragments using as template chromosomal DNA isolated from patients who are afflicted with or carriers of Van Buchem's disease: 50 µl reactions include 20 ng genomic DNA, 0.4 µM each of Vbspan1 and Vbint1, 0.8 µM of VBspan2, 0.2 mM of each dNTP, 120 mM TrisHCl, pH 7.5, 30 mM ammonium sulfate, 5.0 mM magnesium chloride and 2.5 U Taq polymerase (Roche Molecular Biochemicals, Indianapolis, Ind.). The fragments (642 and 720 bp) were amplified by the following protocol: Denaturation at 94° C. for 3 min, 40 cycles of 94° C. for 30 sec, 63° C. for 30 sec, 72° C. for 2 min and a final extension of 72° C. for 5 min. The amplified nucleic acid fragments were resolved on a 2.5% agarose gel using 1×TAE buffer. DNA bands were visualized with ethidium bromide staining.

The results are summarized in FIG. 3. The summary shows that nucleic acid fragments amplified in all PCR reactions containing the 9260/9261 oligonucleotide primer pair regardless of the source of genomic DNA template. The VBspan2/VBint1 oligonucleotide primer pair amplified a nucleic acid fragment from non-VBD afflicted individuals and individuals who are heterozygous for and therefore carriers of VBD but did not amplify a nucleic acid fragment from individuals who are homozygous for and therefore afflicted with VBD. The VBspan2/VBspan1 oligonucleotide primer pair amplified a nucleic acid fragment from individuals who are heterozygous for and therefore carriers of VBD and from individuals who are homozygous for and therefore afflicted with VBD but did not amplify a nucleic acid fragment from non-VBD afflicted individuals.

These results demonstrated that a second methodology presented herein permit the differentiation between an individual who is homozygous for the 52 kb genomic deletion and therefore afflicted with VBD, an individual who is heterozygous for the 52 kb genomic deletion and therefore a carrier of VBD and an individual who does not bear the 52 kb genomic deletion and is therefore normal with respect to VBD in a single multiplexed amplification reaction.

In providing the forgoing description of the invention, citation has been made to several references that will aid in the understanding or practice thereof. All such references are incorporated by reference herein.

From the forgoing, it will, be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for detecting an individual who is afflicted with or a carrier for Van Buchem's disease, said method comprising detecting the nucleotide sequence spanning the deletion breakpoint as depicted by FIG. 2, the sequence of which is provided in SEQ ID NO:101, wherein said nucleotide sequence spanning said deletion breakpoint comprises a nucleotide sequence selected from the group consisting of SEQ ID NO:102, SEQ ID NO:103, and SEQ ID NO:101, and wherein the presence of a deletion breakpoint indicates an individual who is either afflicted with or a carrier for Van Buchem's disease.

* * * * *

SEQUENCE LISTING

```
<160> NUMBER OF SEQ ID NOS: 108

<210> SEQ ID NO 1
<211> LENGTH: 92139
<212> TYPE: DNA
<213> ORGANISM: Homo sapiens
<220> FEATURE:
<221> NAME/KEY: misc_feature
<222> LOCATION: 7043, 8369, 8401
<223> OTHER INFORMATION: n = A,T,C or G

<400> SEQUENCE: 1
caaagatttg attctttata cttttatgt tcaaatttt aaaaatgcaa agaaaaaaa        60 actaaatagg agggaaaaat gttcaacaga aaatttaccc caggaaccaa aaaaaaaaaa    120
aaacccaaaa ctaaagtctc tccttaaagt acacacacat gtggccagct actcctatgt   180
gtgtgcacac acctatgtcg ggcttgctcc tgcccctcca atgcaccagc ctacctactg   240
ggatcccctg tatgtgtatt tgtcgccaat gacactaaac attttcactg tcccaaccca   300
gacgcaccag ctgacgagga gttcgtcctg gagcccagag caaatgcctg cagagggctg   360
gaccagggct gctgggacac acttttaaat cctgcggtgg ggagagagtg acaaatttct   420
gaagtgaaat gtgagagagg agagggaggg gttaacccac acacacaaga tcccctccaa   480
ccaaaaccct agcaggcaac tattaatcat cagaaacctt atatgcacat ctaatgggat   540
ttgcagatgg agacttttaa agaaacattg tctgtatttt ttttttaagg aaagagagca   600
gcacacacac acatacacac acaccgtctt taatgtgcct cctgtaacac tatgaagtta   660
tttttattgc actgttaaca aaattcccca agtcttggat ttagaaaaag ccttaagtca   720
gatccagaat ccatcaaatg ccaaattcca gggagtgaag tgaggaataa gagcaagaga   780
caagcttggt gattgcattt gatttaaagg cccttctact gctgcctgcg aaaaaggaag   840
gtggattaaa agaaatcttt tttgcaagtc tcagcggccc actgtggtct gcagtacaaa   900
gaaaggcaca ctctagaaaa aaagaatttc tctctgccca gagtgacatt ctcactttct   960
cagtaactta aaaaaacaat cagattcttc cttccgctct ttaacctcca acatacatgc  1020
caattagcca cactcttctc tagagaggtt tcaagtcatt tttcttcaca gcaatggcaa  1080
ggctcttaaa taaggtcctt gaagtttctt cgggtctcct cccacctgct ccctgccccc  1140
ttcacctcca cccacctgct tccctttctc atcccccaga ggcggaggct tccgaggaat  1200
ttggggtagg gaaataggaa tcaggggctc ctcattcccc aaaggagcct cctttggcaag 1260 caggcacgtg ggtctccggg ctggtgcaca tcacagggca gccagcccaa gtgccatctt  1320
gatgcccaat cagtcttcct catggctgcg ccctgctggt ctctcagagg gttaatgcaa  1380
tttcttggag gacgacattc ctaacaccca ggggccagaa ctccttcccc actggttatt  1440
cccatggccc agagcagcag gatggggggca gaaacaggca tggaccttaa cagcagcgtc  1500
tctgctggct gcttccaaag acggcgaggg ttccctgagg aggggcccct aggtcttagc  1560
tctgcagcct ggaggtgggg ccctgggggg tgggtgcagg agatgctcct aggaggagcc  1620
gaagggcacc cagggatgtg gaatgaagcc acgactggcc tttaatccag aaactccagt  1680
```

| | |
|---|---|
| cagatacaca tcctgggagc aggagcagct gtaaaagatg gggaggggtg tacatatgaa | 1740 |
| aagatgtgcc ctcttctgga acaagcggtc agagtgttgt agaccagtag agtggatggg | 1800 |
| gtcatagctg tcaaccagac tcatcttttct gctttgccca gggcttagct gtggcacaca | 1860 |
| caattctctg agcctcacaa cttttcctagg atgggtaagt aagaattatg tctccattttt | 1920 |
| gcagatgaca aaaccgaggc tcagatggat gactgggctg cccagactca cacagctaag | 1980 |
| aaatggtgga atcagcactt ggcctcaggt gtcctgctgt tcagtttgga gcaggccaga | 2040 |
| tgcagaggag gaggcatggg gtttgaggtt agacgggtct gagttcaagc cccaggtctg | 2100 |
| ccacttcctg gctgtgtgcc ctggaacaag tcaccttatc tctctgaact tcttttttt | 2160 |
| tttttttcttt ttgagatgga gtctcgttct gtcgcccagg ctggagtgca gtggcatgat | 2220 |
| ctcagctcac tgcaagctcc gcctcccggg ctcacgccat tctcttgcct cagcctcccg | 2280 |
| agtagctggg actacaagca cccgccacca cgcccggcta atttttttgta ttttttagta | 2340 |
| gagacggggt ttcaccgtgt tagccaggat ggtctcaatc tcctgacctc gtgatccgcc | 2400 |
| cgcctcggcc tcccaaagtg ctgggattac aggcatgagc caccatgcct ggccatctct | 2460 |
| ctgaacttct gtttcctcat ctgagatgac agtcagagtg ggatctgtgt aaggcactttt | 2520 |
| gcaccttaca cattttttacc cccacggatt cccacaaaag ccttctgagg caacagtcat | 2580 |
| tctcatcagc tccgttttctc tctctctctt ttcttttttat cagctccgtt tttcagcaga | 2640 |
| agactctgat gcacagatag actgtgtaac ctgcacaagg ccacacagca gggaagcagc | 2700 |
| ggacccagga ttcaaaattga ggcagcccag cccacagaca tttgcaaatc ttcaatgaaa | 2760 |
| tcctttatgt aggccaggca cggtggctca gacctataat cccagcactt tggaaggctg | 2820 |
| aggcaggcag atcatttgag gccaggagtt caagaccagc ccggccaaca tggtaaaacc | 2880 |
| ccgtctctaa tagaaataca aaaattaggc cgggcgcggt ggctcatgcc tgtaatccca | 2940 |
| ccactttggg aggccgaggc gggtggatca tgccggtcagg agatcgagac catcctggct | 3000 |
| aacacagtga aaccccgtct ctactagaaa tacaaaaaaa aaaaaaaaaa ggcgggcgtg | 3060 |
| gtggcgggcg cctgtagtcc cagctacttg ggaggctgaa gcaggagaat ggtgtgaacc | 3120 |
| cgggaagcag agcttgcagt gcaccgagat cacgtcactg cactccagcc tgggtgacag | 3180 |
| agcgagactc catctcaaaa aaaaaaaaaa aaagaaatac aaaaattagc tgggtgtggt | 3240 |
| ggcacatgcc tgtaatccca gctactcggg aggctgaggg caggagaatc gcttgagcct | 3300 |
| gggaagcaga gaggttgcgg taagccaaga ttgtacaact gcactccggc ctgggcgaca | 3360 |
| gagtgagaca ctgtctcaaa aaaaaaaaaa aagaaaaaga aaaagaaata agaaagaaa | 3420 |
| tcctttatgc aaaaggcaga gtaagtaatg acaaatgtg gctccctttcc tagcacatct | 3480 |
| atttctggtt aacctcgatg atcccaaagg gtgaacctgg gaatgggggag ttctgaggaa | 3540 |
| attctacaga aacagccttg tgaggtcctt tgtgggggc acgctgtgct gtgggggttc | 3600 |
| tggaaggaat ccgtgggagg ctgggaggaa gatctggctt gtcagcttcc ctaggaaaac | 3660 |
| cttcccctgg gctggccgca ggctgtaacc ggattcctgc tccacctctg catctggccc | 3720 |
| agggacctca tggcagggag gcccagcgcc tggccctttg ccctggacg gggtgggccc | 3780 |
| tgggtcatgg tggggtgggt ggggaggtca ggagggccat ggggaggggg cgcggtgggg | 3840 |
| tgctttgccc tgagaacaca ggcctctggc acccggagc cccggcagc tgctggcgtc | 3900 |
| tgtcagccac cttgcggggc gcggccgggg gcctgctggc ccctacatct tcctgacagg | 3960 |
| cccctcttct gaggccagga aaaacaaca acagttcctc ccctcacggc aacccatttg | 4020 |
| ttagatgaag gccgggcacc agcacccttta acctcctcaa agtcagcgtt tccctgtcaa | 4080 |

```
ggccccacag ggccagagac agagatggat ggaaggagct gtgtgtcgaa aaagccctgt    4140
ggcctcatga ggagagctct gttttcagga agggagggga ccccggtttc tgattgttgg    4200
ggagaataag gggaggaaga ggaaaagtgt gagtcacgag gaggtccccc aggggcgtgg    4260
gggggcccag gaggctttca gcctggccac acctgagcca tcacgtgaa cttgcggaat     4320 gtctcccatt gtgcgtggca ggcaggcgtg tacttggcag acagggctg cttctgtttg     4380 tggccacccc acccccttgt gcttggagag gcagggtgtc agggcaaggc cctgacctg     4440 gaggcagaag acacgggttc aaggtgtgac cttgcctgtt accggctgtg tggtctcagg    4500
caaatcacac ccttctctga gcttcatttt tctcactggc aaaatggagt tgacagttcc    4560
ggcctcacct ggcggttagg aggataaatg aactgcatct gagaacagag ctggctgact    4620
ataaagggtg atgcatgtga ggaatagctt gtccttaact atgctgaacc actgggcagg    4680
acacagcaca atgtaggtga agacggctca tcccagcccc cagataccatt ctatggcaac   4740 ataacacaag gtccaaatc atggccttgg gaattggggg cctgtgggtt caaacctcag     4800
ctctgttttt ttgttttttg ttttgagacg gagtcttagc tctgttgccc aggctggagt    4860
gcagtggtgg gatctcggct caccgcaacc tctgcctccc aggttcaagc gattctcctg    4920
cctcagcctc ccgagtagct gggattacag gtgtctggca ccatacctag ctaattttg     4980 tatttttagt agagatgggg tcttgccatg ttggccagac tggttccaa ctcccccacct    5040 caggtgatct gcccgccctg gcctcccaaa gtgctgggat tacgggcatg agccactgtg    5100
cctgacctca gctctgttat taataagcta aatggctttg agcgacttgc cttatcactt    5160
gagcctcagt ttcctcatct gtaaaatggg gataaacttc ttccgtccgc atgaggatgc    5220
tgagagacgt gagtgaggtg gtctatgaaa gctcttgtca tagcctggca tgcaggggta    5280
acatctggat gatgaagatg atgataccctg agattttttgc cttacagaca actccagaga  5340
gccctgtgaa atatttatat gccactgaac agggcacaag atgaagccat tagcctgcgc    5400
ttacatagta gaatgtgtga atcagatgag atgcttggtc tctagtaaga ccttaaggga    5460
tggacagaag acaggcagat tttggatatg gtatacgtgg ctgtgggcta gcgtgtttac    5520
tactgggcct gggatgtatt tggaatgtac acatgtgtcc tttgcttctc agaacacttt    5580
gaggcagcag agttactact gcctgccagc ctgcctcaca gggttttttg ttttgttttg    5640
ttttcttttt tttgagatgt agtttcactc ttgttgccca ggctggagtg caatggtgtg    5700
atcttggctc actgcaacct ccacctactg ggttcaagcg attctcctgc ctcagccacc    5760
tgagtagctg ggattacagg tgcatgctac catgcccggc taatattttt tatttttatt    5820
tttatttatt tatttatttt tgagatggag tctcgctctg tcaccaggct ggagtgcagt    5880
ggtgcaatct cggctcactg caacctctgc ctcccaagtt taagtgattc tcttgcctca    5940
gcctcccaag tagctgggac tataggcacg cgccaccaca cccagccaat ttttttgtact   6000 tttaatagag acgaggtttc actatattgg ctagggtggt cttgaactcc tgacctcagg    6060
tgatctgccc gcctcagcct ccaaaagtgc tggaattaca ggcatgagcc accgcgcctg    6120
gccctgacag ggctttgtaa tgctcaaata atatgatcca agggtcagag ttgagtaaac    6180
tatagaacat agtccttgca ttccaccccca ggggcccaat aacgaggtct ttctctaaat   6240
ctcagaaaac actaagctaa gggaggtaag ttctgcagat gggttttctc tgtgtgtgtg   6300
tgtgtgtgtg tgtatacata tatatataca cacacacata tatatatata cacacatata   6360
tatacattta aacctttggt gctctacttg tctgctacca aaattgtagg cagatgactg    6420
aaaaatgtaa cacacagaat ggcctgcata gaaacctggc tcttggaagt catatgagtc    6480
```

```
agtttcctca actgtaaagt ggtggctcac tgtacagaca ctcagtaagc acccagcaaa    6540
tgaacacctt ccaggggttc tgtattggag tcagctgtat agaatgaaaa caaatgacaa    6600
aaggggaaac acacagagtt tattattctc ccccataaaa aaggccggag gtgacagtcc    6660
aagctgagat ggcctctccc ccaggcactg tctctctact tgccccccct gcggcacctt    6720
gttcagctgg catgtcagca ttccacacag cacgaaggag gaaggacaaa tggactctcc    6780
ccatctctct gcccactgcc cccctcccca caacccgttt aaaaaataga tatggggggc    6840
cgggtgcggt ggctcgtgcc tgtaacccca gcactttggg aggccgaggc gggtggatca    6900
cgaggtcagg agatcgagac catcctggct aacacggtga aaccccgtct ccactaaaaa    6960
tacaaaaaat tctccaggca tggtggtggc aggcgcctgt agtctcagct actctggagg    7020
ctgaggcagg agaatagcgt ganccgggag gcgtagcttg cagcaaggcg agattgcgcc    7080
actgcactcc aagcctaggc gacagagcga gactccatct caaaaaaaaa aaaaaaaaaa    7140
aaatagacat gggggcctgg cgcggtggct cacgcccgta atcctagcac tttgggagtc    7200
cgaggtgggc ggatcacgag gtcaggggtt cgagaccagc ctggtcagcg tggtgaaaat    7260
ccatctctac taaaaatata aaaatcagct gggcgtggtg gcgcatggct gtagtcccaa    7320
ccactcagga ggctgaggca ggagaatctc ttgaacccgg gaggcggagc ttgcagcgag    7380
ccgagatcgt gccaccacac tccagcctgg gcgacagagg cgagactccg tctcaaaaaa    7440
aaaaaaaaaa tagacatagg gtcttgctat gttgcccagg ctggtcttaa actccttcct    7500
tgagtgattc tcccaccttg gcttcccaaa gtgctgggat tacaggagt gagacacagt    7560 gcccagcctc tctacatttt ttttttttt ttttaagaca gactctcact cagtccctca    7620
ggctggagtg cagtggtgtg atctcagctc actgcaatct ccacctccca ggttcaattg    7680
attctcctgc ctcagcctcc caagtagctg ggactacacg cctggctaat ttttgtattt    7740
ttagtagaga cagggttttg tcatgttggc caggctgatc tcaaactcct gacctcaaat    7800
catccacccg ccttggcctc ccaaagtcct gggattacag gcatgagcca ttgtgcccaa    7860
ccctccctgc cctgttttaa ggagggtcct gttcaacaat tactctacag accaattgcc    7920
cgcaactata tacttggcag tgaggaactg ctggggaggc tgggagattc agcctatagg    7980
caccttggtg gccctaataa ctcttttatc ttcttcttct tccccatcag aacctgttct    8040
caaggaaaag agctaaggta ggctgccaga taaaatgctg aggtaagtct gttccagaaa    8100
atattgggac atagactaaa aaattgttgt ttgtttatct gaaactcaaa tttaactgag    8160
tgtcttcttt tccccctaaa tctggcaatc ctaatccaag gctaaactca ttttcaggac    8220
gcaaaaggct ctggccttac cttttgagtc aggacgttgc actttgacag aaggctctgg    8280
aaggaaactt taagggagc cttcagagg gaaatgcggt gttggggtag gtctgccttt    8340
ggctatgggc tttctggctg ccggagggnc ccagggtccc ccaggaaagc cttctgtgga    8400
nggtcttttg agagagacaa agcagagggg tggaggaagg gcggctcagg tggaaggagt    8460
gaggacaaag gtgagtgccc ctgggcagga agtgctgaaa gagagaagga gggaggccac    8520
caggcctggg cctggagcca gcctgggaga ctcccagccg cccacttctc ggggcctccc    8580
ttttccagcc ccttgctttc gaggcagcag tgccattatt tggggaaacc agctaaccag    8640
ataggacagc aaaccgggga tttatgtggt gtgggaacag ctcaggtttc cctccctgtt    8700
tacccagcag tatttttaa aacagaaatc agcgtgtggg taaccgcagc tgtgagttac    8760
tagctctggc tgtgagggct ggggtggggg gagtctcttc agagccctct gtccactggc    8820
ctgggagcta ctgaaggaat gtgcctctcc ccatcccagg ccaggtggag aaggtggccc    8880
```

```
tgcggaagtt cccagatcac tgcccacctc acccttcccc tcccgacgaa ggccagcaca  8940
cctgggggag gtgtgatgat ggttcaaggt ctaaagcttt agagatcagt cagtttaggg  9000
gtcagaaccc atggagccag gcaagtaaac acaggttccc caagccagct gggagggaga  9060
cacctgggtg cctttgatgg gagaaagagg gggccaacag ctacttggca ctggccaatt  9120
ttcccttgca tgaacatggg cccagtgtaa ccaaccatat cttttccattt gtcaaaaaaa  9180 agccatattt ccagattttt tataggcaac ctgtcaactt ttaaatgttg gcaatgaatt  9240
caaaacactg ccattcaatt aaaagcagcc agaacatgg cacgactggt cttggaata  9300 ccaatctgca atctctgatc ttgtccaact ctctctgctc cccatttac agatcaggaa  9360 gctgaggccc agagaggcct agggacttag ccatggctgc agcagttgtt attgggaatg  9420
ccatgaggcc aggatgcctg ttatgtgttc tttgcccagc ctagcagttt ggctggcttg  9480
gctatgccag aggtctcacc atgcagttct caagtgcttc ctgagcatct ctcatttgca  9540
tagacatgac atttacaaac acatccatca tctacttgat tctggcaatg acaccgaggg  9600
agcagaactg gcattaatcc attttttta atggtgagaa cactgaggtt tggagaggct  9660
ggtgacctgc caaagtcaca gtcctagaaa gggctgcagc cagggcctcc aattacagat  9720
caagggtttt tccacccca aactcagtca tctcgtaaaa acgtcaggct ccttggggaa  9780
tacagcttga gatggataat caactcctcc taaaagggaa ccataaatgg atgagatact  9840
tgggtaaact gaatattctt tgtaacttaa agttaattga aaatccatag gttatcaatt  9900
ttccaagcag gagaataaaa tagaaggtat ttcaaagagc aattatagta ggcatggctt  9960
aatctttctt tgatgattct gaaggcattt caggggaatg taatgcctta gggcatcatt  10020
atgaacacca ataattactg tgtagggctg tgacgcaaat tctcatcaat cccctcctgg  10080
ctgtcgggtt gttttcagag aggatcatgc agggagtgtg aacgtgtgcc tgtctgtttc  10140
ttgctgctct ctccgccttt gtcaatttca gggtgctgtt gtggaaaatg cagtgtccct  10200 ggaagggga ggtcacttaa ccttaatgag cttctgtttc tttattaaaa tggggtaatg  10260
cagactccta tactcactgt caaggttttg tggggctcag atgtcagtgt cagagcagga  10320
agaaacttta gatcatgata tgcaccagct tcattctgcc atgaaaaat ctgaggccca  10380 gagaggttag gagcctcgtc caaggtcacc cagccaggga gagggtgcta aacctgggt  10440 tttctgcttc ctaacctctt tcctgaatat aacactatgg aagaaaaga tctgaggaa  10500 cggaaagatg aacacatgat tacacatgca aacaatactg gggtctctct gatcagagaa  10560
ggtgtgatct tccagcctca ggagagggc catccaagtc ctggaggagg tgaacccctt  10620
agttcagggc tggagtagc ctgggggcag cagagacact gctgtgaggt ttatagtttc  10680
atgactgtca gagctttta aaatgtggta attttaagtg tgcagcctcc cagggtcttt  10740 cttctttaa ttgaagaaat aaaccatctc ccctaaggca tgcttggcga aggagaaagg  10800
caggtgcaag gctcacagag gagagcagca gcctagaagg gctctgtgtc atggggaagt  10860
aaaacatccc agaaacagag agcagaaggc cttgactgag ccccaggaga ggcaggacac  10920 cagggtgca cacccataaa cacacacata cacatgtatg tctcctcct ggagcctgag  10980 agtccctata tacagcaggt gcatgtgggc cacacatcac acaaaattga atacaggcag  11040
gctcagagca ccagcacaca cgtatgtcct tgacacccttt agagatacta ctaagcacgt  11100
gtgtgtacct gctcacccat atggcagagc ccctggatct gggcagaaat gccaaagcag  11160
gggcaggcgc gtgtgcgcgc acacacacac acacacacac acacacacac tagcacagcc  11220
acaaaagctc aatccacatc cagcattcct aacaacacac acacagctag acacgctagg  11280
```

```
agacacatca ggacaatgtt tccactcccg ctgccataca catatgcagg tccacattca    11340
ccagtggggt agggtagagt ctcatcagtc cagactcgca gacagctgga cacagaggtg    11400
atctctgaaa cccaatgtct acacactgtg gtctttgtta cacacacaca cacacacatt    11460
gaaatgatgt cctcagcctt tggttatttt tggtttcttc tgagctggag tttcactctt    11520
gttgcctagg ctagagtgca gtggcgtgat ctcagctcac tgcaacctcc acctcccggg    11580
ttcaagtgat tctcctgcct cagcctccca agtggttggg actacaggcg cccgccacca    11640
caccctacta atttttgtat ttttagtgga aacagggttt caccatgttg gccaggctgg    11700
ccttgaactc ctgacctcag atgatccttc cgccttggcc tcccaaagtg ctgggattac    11760
aagcttgagc caccgcaccc ggccgagcct tcgggtattt tgaaagctga atgtgtggtt    11820 acatttctt ttctttttct tcttttttttt ttgagacgga gtctctctct gtcaccaggc    11880
tggagtgcag tggcgcgatc tcggctcact gcaacctctg actcccggt tcaagtgatt    11940 ctcctgtctc agcctcctga gtagctagga ttacaggcat gcaccaccac gtccagctaa    12000 ttttgtatt tttagtagag ccagggtttc accatgttgg ccaggatggt ctccatctcc    12060
tcaaatcgtc atccgcccgc cttggcctcc cgaagtgctg ggattacagg cgtgagccac    12120
agtgcccggc ctacgttttc aaacagcaat agcattcgcc tcctctgtca gtttaaccc     12180 catcacaact cccactttg gcacctaaac agttaatttc ccagttcatg ggccttcaaa     12240
gtcctgctct agtctctgga ggaactttca cctacagagg aaggtgtaag ggaaactagt    12300
tcatggattt aagtagaaac atttaggtg tagctttcac atacagagga gtgagaaaaa     12360
actgattcat ggatttagat ggaaacattg tagtatgaac ccagcggagg gtctgggagc    12420
gccttctggt ggtgagaatt agaaccgcag cactttctgc aatgtgccca ggccagaaag    12480
ctctaccttc tgataggacc cacttctgac cctagaatgg gggaactgat ggaggtgtca    12540
agccactgtg gtcccacagc tgcatgcagg cacaggggat aggaagagag ctacctacag    12600
gttactaaac cattcccttt taaaacagca ccaggcttat gtctactctg cgcttccatt    12660
ttctaggttt taagtggaag atatgtgaac cccagtggg ctggatggct gtccctgcta     12720
caagtctgtg atgtctccgt ccagtggcag agctggaagg caggtgctgt cggggctgca    12780
tctgccttgt tcaccagcat aggcctaaaa ccatggaggg ggtgctttgg cttagatccc    12840
cacttggcct gtgtgtgtaa gaggctctca ggcaccttaa tgctacatca ccaaccaaac    12900
ctcctgatga ttcttttagg ttctccgttt ccaggcagat tcacttctgt agatttattt    12960
atttattttt gagacagggt ctggctctgt cccgcaggct ggagtacagt gatgcaatct    13020
cggctcactg tagccttgac ctcaacttca agtgatcctc caacctcagc ctcccagtat    13080
gagggaccac agtgtgcac catcacacct ggctaatttt tgtacttttt gtagagacgg     13140
ggtctcacca tgttgcccag ctggtctcaa actcctaggc tcaagcgatc caccaacctt    13200
ggcctctgaa atgctgggat tccaggtgtg aagcaccgcg cccagtccct gacttctgta    13260
gacgtttgta ttgtttacat ctactgtgtg caatgtacga gatgcagtca ggtgtctgga    13320
tggaccaggg gatctggcat cttatagact tgggtttgaa ccccaactga gccatttact    13380
ggctgggtga cttgggtga gttcttaaac ctctctgacc cttaaggtgg taacagtatc    13440
accagtgaag ttggtgcaca cagcagggcc caaactgaca tctcacagca cccagcaggt    13500
cactgtgggc atgataggat gatgggtcac tgtgccagcc ctgaaggagt tcaagtccag    13560
ataggggaag gtggtggacc agacccagac agagattctg agtcgctgct gagactgggt    13620
gagggtagtg ggtacatggg aggacatata gcccggcagc ccagggctgg agtccacact    13680
```

```
caggttgggg cagcctggtc tgcctctcct gcaggagact tttccaggca ggcttgtccc   13740
tccagaatgc acgaatcaaa tcctctcagg atcagtctca ttttcctcgt gctgggggag   13800
caggctactc acagaagatg ttgttgcaaa tgtaagaatc acatgtcgat ccacaaactg   13860
gcattgagca gctacctagg agatcaaaga aactcttact ttgggagctc ctgccagggc   13920
tctttgggag gtctggctag ctctggagga agagaatgaa cttggggagg gcgtggaaca   13980
gatgaggacg caggcactgc cattcaaaga ggagaggtct cccggacagg gctggcctgg   14040
gcaggcccag ggagggtggg gctggagcag ggacttgaaa aagggagagg gctcaggaga   14100
ctcagaggag gaggaaagtg tgtgagcagt aggcagggtg tgtgtgtgtg tgtgtgtgtg   14160
tgtgtgtgtg tgtgcacgcg cgcgcatgca ggcctgtgta gggctgggaa agaacaaagc   14220
aaaagggtgc acaaggcatc cagaagccag ggcaatgcag aacaggaaca aagcagtttg   14280
gctcaagggg aaagttctga tggaaagcaa ggaaagagaa tgttagaagg gctgagagcc   14340
agaatgccca gtatgggta cagagggcaa cagaggggct gatgttggtg gcgaggtggg   14400
gaggagcatt tcacagggaa ctgggcagct ccaaggatgg gctggaggag ggacggtcct   14460 aaaggggtg gtgggagaca ggcagttagt gatgggggga gagaaatgct ctgaggggg   14520 ctgctgtagg cagggagggg caggtagcag gaggcagagg gttgagcctg cagaagcccg   14580
gagcagtctg tagcttttcta atgcttccta gggaattctg ctgctgagta gccatgggtt   14640
caacaggtct ctaggatttg ccttgaatta ctgccctgag gcccctaag tctggggtct   14700 cataaattca gcggggaggg cacacctgtg tctgagtctg agcagccag agcccccagt   14760 gttgtcagtg aacagctcac tgaacttgca gagcaattaa atcccagggc agaagaaga   14820 gcaggagggc agggtggccc ccagctccct cccatcccgg gtttggggag agacacctct   14880
ggcctgagac tcctcgtggc ctctaacaag tcttgctctc tctctctttt tttttttttt   14940
ttaaattatt gtctcccgcc ctccttcctt cttcttggga atcagaaaag aaacctcaat   15000
gcctggcttt gccctccct ggctgtggtc aagccatgtg acatttagac atttcagagc   15060
ctcctgactc ctgaggctgg agacagcatg aagccaaatg gcttggcaa acagaagaga   15120 ggggcagtta acattctctg caatgctctc ttacttcccg tttaaacacc cctcctactc   15180
ggacacagac ccccaaccc tgtgccattg tgctcactcc caccttggag gggtcaggct   15240
gtggtgaaag gtcaaggtga aaagtcatga tgatcctatt gctgccacct ccctgggtg   15300 agcaagattc tgtggtggct ccagctctcc catggcagtc cacacagagg ctgttccagg   15360
ttctggagag gtcacttggt gtgacctggg aatctgcatc ttttctctgc caaagcagag   15420
ggcattgcag caaccacacc tgggtcccag tcctcaacaa agtccctcca gctcccgctg   15480
ctgtctgcaa ggtttggtca tctgtccctg cattggagaa gagtttgcac tgtgaatctt   15540
gcctccacca gggaaggctg gtaaaagtcc ctgccccggg ggccctcatt gctccagggt   15600
gcatctgggg gccagacctg tggaccctca cccttgagcc tcattttgtt cctcttagaa   15660
caaagccatt tctggtaaat aggtttgatg gtttggcag cagggaaggc acagaacctt   15720
tcacgattag caggctcatg acaatttctc tttaggcaag agagaaggtt gaggaggaaa   15780
gactggcagg gcttggagag ctggaaagga agaaaggccc tacaggcctg gggatcccat   15840
ctctgaccac cgaccccagc ccccaactct catagactct gatttgatat tcttatttac   15900
caaagaagct gcatgtattt gcatatcaat tctctttccc atatcgacac gcaggaggc   15960 ttcttcgttt tggatcaacc agagatcacc aatgtctgca gggtgctcag cccctggtac   16020
cttggtcact ctaggcagcc tcctagatgt gcctcttaag ataggttttc tgaaatggga   16080
```

```
gaggaccacg ccccgccccc caccatggac tctggagtct gcggcgcaca aatcctgcga   16140
ttttacagat ggggaaacag aggcacggag aaagtctcag cttttcccacg gcccactggg   16200 accagaaccc aggtcgcagg acggggacag ccacctcctt tttctctcct tgcaaccagc   16260
ctgagctcgc tcagcgggtg ggggctgccg ctatccagag caccctgttt ctggatgcaa   16320
aataaaggcc caggcagtgt ttggccctcc tctgcccaca gactttggct ccagggcagt   16380
ctccgagaga gaagccttgg gtcccactgg tccgagctct gcgtgctgag tctagaggct   16440
gcagtctcta agccgaaact agcccaggcc tcacagccgc cttccgccg gtctcccact   16500 gccttggcgg ggcgctggcg ccctctgctg gccaagtctc gctctgcgcg caaacgcccc   16560
agaaatcagc cggaagttcc ctggggcccc acaggagtga ggacccacct ggattcactt   16620
tgtcattttt ttttagctgc atgaccttaa gaaagctaat gaacctcaga gcactacctg   16680
tgaagtggaa ataatagcgc ctacacttca gggtcggtgt aaggattgca tagaataccg   16740
tatagaaagc acccagcaca ttgtaggtat gtttaatggt agcgattatt aataatgccc   16800
aactcacatg gtgagatgag atctgagaag cctccttata aaggtaaatg ataaccaagt   16860
cttgttgcaa ggcagctggt gtgttactaa tacatcatga ggtggtgggc cctctgggga   16920
ctgtcaggag acagcctctg ttttattagg aaataaaaca gaatctggtc tgctccagtt   16980
ttcttccttt tatttactgc attagaaaac tttcatttta tttattgcct attctggggg   17040
ttgagggtga ggggaaggca tgactccagc caggtaggat acaaaagtat ctcaccccc   17100 aggaggggtt tgaggaccgg ccctccggct tttagagaag ggcagctggc ttctgttgct   17160
aacgatttgg atttggcttt taacagaata tcaaggtgaa agtgaaagga gcttttcact   17220
ccttggagag tcaagagggt gtggggtggg acctccaggg gaatgaagag tgagcgaggg   17280
tgctgggggg atcccagacc taggaatcag atctgggaa ggggtctgca agaccctcc   17340 atgagtcaag aaaagccggt gggtggatgg tgagaaggac cagtgaagac actgtttgct   17400
ggagttgtcc cagccagtgg ctatgactga gactgtccca tggcgtgtgc ccagggtcct   17460
gccattggat gatgggacat tctttttttt ttttttttt ttgagacgga gtctcgctct   17520
gtcatccaga gctggagtgc agtggcgcaa tatcaaagtc gctgcagcct ccacctcccg   17580
ggttcaagca attctcctgc ctcagcctcc caagtagctg ggattacagg cgtgggccac   17640
cacatctggc taattttgt atttttagta gagatggagt ttctactcca tcaggctggt   17700
ctccaacttc tggcctcaag tgatctgctg cctcggcctc ccaaagtgct gggattacag   17760
acgtgagtca ctgtgcctgg cctggatgga acattctgct cttttctcat ctgctgccta   17820
cccatgatgt cttgggactc ctagaaccct aaaggaagcc cctggacacg caggaaggtg   17880
tggagaggag ttctcatact tgcacttggg aggagggctc aggagaaaca gaggctggca   17940
acaccccctc acacactggt cctctggagg gccagtgtct acagacactg tggactgagt   18000
ccacagagag gaaagggtcc tgccttcatc agaactgctc agcaagcagt tccatcccag   18060
ggggtcctgc gaggtaaggg aggggcagct agctaggtga ggggctgaga gagtggggag   18120
gggaaagagg gaagaagaga gtgagaggga gaggagggga ctgagccgat tctcagctcc   18180
ttgaccgttt gctgagctct gtctgagtgg acagatggtc ccaagtcagg ccacaccaga   18240
gtggcctttc tgctccccta cacccctgcat tcctcaacat tgctggcccc ggagagactt   18300
tccttcagag aagcaaatgg ctggggaatg gtgaaagaca ctgcagagaa aagaaagcac   18360
agcctgctgc cctgggaatt aacatgattt aggagacctg caggtcaccc cctcatgact   18420
aaaagccatc ctggaatgaa ggtctgtggc tatttctagg caaaactgtc tgataagata   18480
```

```
aaatagctca actcctgacc attaagtcgt gaaggccatg gccatcgtaa atctcatctt  18540
tccggccctc tggcctgcat gcagtgcagc ccagccagtc ggtggcagcc accttggtag  18600
gaagggccct catcctcctg gctgtgcccc aaggactggg caggcttcgg tgccaagggt  18660
agtgcgagca cttgaaagcc gccctgtatg tttattgttt tccccaggtg atccagaatt  18720
actcccgaac tctaccagct gaaatcctcc tcaactcaca tcagacaaga cggccctgcc  18780
acttacctgt cagatcactt tgggcaggta agctcatttt cctgaatctt tacttccaca  18840
ccttaaaatg tgagcaatac tatctccctg gcaaggttgt tgtgagggt aaaatgaaac   18900
aataatcacg ggtgcatcct ggagctcttt cttacaaggc gtgccccaa atctgtcccc   18960
tctttctgag gatgcccttc ccctattgtc tccctggcca tttcctaccc attctcaagg  19020
gccatgatct cagggagttc tcctgactca cccaggcata ttggatctcc tacgtactgc  19080
tacgactgca cacaggtgca ggaaatggct gtttgctttg cgtttgagga acttggaaag  19140
ggagacgtgg tagggaaagt agtggttagg ggcactttca gactgaagga tgtgggttgg  19200
ggaatacggg attcttggag ttgaggacgc cgcttctctc gtctctagct aatgtgagaa  19260
agacccttct ggacactaag cctgcaattc cactggtggc taccaggtgt ccgtggtgtc  19320
ctggggcggg tgtaatgaga gcgggagcct gtgaaaccaa aagcattgtt tttataaatt  19380
cagcactctt caatccctat taataaggtt agcggtgcag ttcttgcgtc tcctgccctg  19440
cctcaccttg caatcatatt cattggcatt cctttcttcc aagaacccac ctaggaggcc  19500
ttgcaggaga tatctctggt gctggctgtt cctgcagtct gaaaagccag ttaagataca  19560
aatatgtgag aggacactgc ttgaatctga tttcattttt taaaaagttt aattattcac  19620
agactttgct tctttctgac tagtaatgtg acacctgtga ctcagttcaa gatggtgtgt  19680
ggtgaccttg cagttgagaa gcactgagcg ctatagccat gccaagaagg ttgcccctcct 19740
gggaccagca aaaattccat ccagggggcc atctctgtca ggcttgtcct gactatcttt  19800
ttggagaggc ggcagagtgg agtggttaaa agcatgattc tggagcccag ctacctggga  19860
gcaaagctcg tctctaccgc ttaccagctc tgagagctta ggcaagtgac ctattctctc  19920
tgtgcctctg agttttcatc tgtgaaatgg gagtaacaat agtcctgtct cacagggttg  19980
ctgggaggct tgaatgagtt aatgtccatg gggtgctgaa tcagtgcctg catacggtg   20040
aaggccatgt gagcagtaaa tattattatt attagaaagg ttggctgggc gtggtggctc  20100
acacctgtaa tcccagcact ttgggaggct gaggtgggca gattacgagg tcaagagtta  20160
gagaccagcc tggccaacat ggtgaaaccc catctctact aaaaatacaa aagcattag   20220
ccggtatagt ggtgcgtgct tgtagtccca gctactcagg aggctaaggc agaaggatcg  20280
cttgaacccg ggaggcagag gtttcagtga gctgagatca cgccactgca ctccagcctg  20340
ggcaacagag tgagactcca tctcaaaaaa aaaaaaaaa agaaagaaag aaagaaaaaa   20400
agaaaggtc ccaacctact cacttattgt tcacttgcat caaatgctag gttcagtgta   20460
ttgttcttgt aagattagaa atggagagat gggtcagaag gggttggtca aaatagacct  20520
ctcaacccaa gcagacaggg ctggcttcat ggccggcaa ccatgcagga cccagggctc   20580
taagataaga aaggcacgta gtttaatgct ttgctgtccc atcttgatac tgtttttttt  20640
ttctttttttt tttggaaatg gagtttcact attgtcaccc aagataaagt acaatggcgt 20700
gatctcagct cactgcaatc tctgcctcct gggttcaagc aattctcctg cttcagctcc  20760
ttgagtagct gggattacag gcatgtacca ccacactcag ctaattttg tattttagt    20820
agagacgggg tttcaccatg ttggccaggc tggctggtct cgaactcctg atcgcaggtg  20880
```

```
atccacccac ctcggcccca caaagtgctg ggattacagg catgaaccac cgtgcctagc   20940
tgatattctt aatttatgaa ggaagggccc caaattttca ttttgcactg ggcccacaaa   21000
taacgtagca ggtcccacaa acaaattcgt ctagattcag agggccccct gccttcctcc   21060
tctgctcaca ttcgttcctt tctcccatca caggcgggta ccctaccttg ggggatttgc   21120
cccagaataa gccttttttt tcccttctaa cattttaatg aaaaatttca agtgtatagc   21180
aatgttgaaa agattttata gtgagcaccc atacacctgc cacccaaagt ctaccattaa   21240
tgtcttctgg acttactttt gccgtcttat tcatactctg cctggactgt cctcagctac   21300
aggactcaca tctcttgccg acagctctaa ggcttccagt cctgctgtct ggaccaagaa   21360
aggcttcctg ggctctgagt gtcaaatggc ggccttcaag gaagggaat ggtggaaaag    21420
gccgtggggg gttttggaga aattgctagg gaaagactgg caccagagtt ccaccagccc   21480
aggcaatggg gggtacagaa cccataagat gagttctaga aaagcaagga aggtttcgtt   21540
ctggagtttg tggactgagg tttccatttg tgactaggat tctcattggt tccttatgta   21600
gtttcttacg ccctgcatag tcttctaagc atttctcaca gacgtggtct gggggcgaac   21660
accagcagcc ctgagaggtg gctaaagagg agattcttct ctccacttca catcgtagga   21720
aactgagtct cagaggttcc ttccctggcc tgcccacaac cccagggcta aaagaggcag   21780
accaagccca gggccttgaa ccccaacaat gggcctcttt cttttgatcc catgataggg   21840
gtgcaaaagc attgcattcc cctgggtaat ttgaagaaaa acccaaaaa actccaactt    21900
tgtctccagg aaaaagaggg tgtctgggct atgatttacc tctgagggtg tggttgcact   21960
gagcgtgatc acacttcaaa gggttagatc tcatttctct gcctttctag cttgggccca   22020
gggctcagaa atgtgtggac tccctcacag cccctcccag catccctgcc ccctcccaac   22080
tgccttgggc aggtgacacc tgtattattg ctaagggtta aaaagccccc aaatcaataa   22140
aacccattaa tgagtgttgg tacctcgaag gctacagata aatcccttct actcagtgag   22200
ttcaatccca taaaacagct ctccccttc aatcctagca ttcatttgat agaaaatgtg    22260
gagaaatttt aaaaaggtga cttactaatt gcctgtaaaa taaaaggcag atggaagctt   22320
tattacagtt gaaggaagtc gggaatatta aggtaaaatg tcaaataaca attgattttc   22380
cttagacata aaggggcgat ttatggcttc ctagttacta caaacgagaa attatttgaa   22440
gttctgaaaa gtatgaggag aaataaagat taaatagaag atgaaatcat agggatttct   22500
ctgggaggtg acttcagtgc ccctggggac tagaattcat gtggccagtg gcctagccag   22560
ctggggcttg gcagtttcaa gatttagagg caaggtgtct ctgaggagcg gggaagtggc   22620
tgtttgcttt gtgtctgagg aactaggaaa gaaagatgaa gatagggaaa gttgtggtta   22680
gggccaattt cagactgagg gatgtgggat taggggattc ttgtggatgg gcctatagct   22740
ctgcttcctg actagcagat actggggatc tggggaaggg aagggtgagc tgccttcct    22800
gggacttcga tggcatcctt acagtcaggg gacactgtcc ttgctgggtc ccggacatca   22860
gtgtctatgt atccctgcaa gccacagcac tatccaggcc ctctggtggc tttgcttggt   22920
ctgggccaac ctggtctcca cactgacagt caaagacgag gagaggaaaa agaactcacg   22980
gctaggcgtg gtggctcctg cctgtaattc cagcactttg agaggccgag gcgggtggat   23040
cccttgagcc caggagtttg agaccagcct ggcaacatg gcgaaatccc cgtctctaca    23100
aaaaatagag aacaattacc caggaatggt ggtactctgg aggttgaggt gggaagatgg   23160
cttgagctcg ggaggttgag gctacagtga gctgtgattg tgccaccgca ctccagcatg   23220
ggcgacagag caagacactg tctcaaaaaa aaggctcatt tccaggctgc caggcttatg   23280
```

```
ttagcctggg gtcccgcagg agctgacctg agacaagtac ttgagggcaa gttgtttgtt   23340
tgagggatgc tcacaggaag ctccagtagg agggtaggga ggtgacccag ggaaggaagg   23400
cagcttacag gggcgtgttg tcaggaaggg caccccggcg ggtgacggaa gcttaatttt   23460
gctgggaaac tcaggagcca gcatggaacc tgcacctcag agttatccca ctggaaggat   23520
gagggagcgg gtacttatac accaactcca tccccgtcct ttgttaaggc tgctggatgg   23580
agtgggtggg acactcattc ttcagcactc ccaggggccc tcaggctgtc agaagttagg   23640
tccgttgggc tccaggatga ggggaccccc agaagatgcg ggagggcgtc cgcagcatct   23700
gcctctgtgc tttccctgtt tatctgaatc ctcataattc ccgccacatg cagatcagag   23760
cccccagctt tatggaagag aacacaggtt tggagaagat aaagagcatt cccacaacta   23820
ggaggtgggg aaagctagga gttcagccca gagctccctg acttcaaagt ccattctctt   23880
tctacttcct gattttttt tttttttttt tttttgaga cggagtttca ctctgttgtc     23940
taggctgggg tgcagtggca caacttggc tcactgcagt ctctgcctcc tgggttcaag    24000
caattctcct gcctcagcct ctcgagtagc tgggactaca ggcgcccgct accatgcctg   24060
gctaattttt tgtgttttta atagagacag ggtttcaccg tgttggccag gctggtctcg   24120
aactcctgac ctcaggtgat ccgcttgcct tggcctccca aagtgctggg attacaagca   24180
cgagccactg tgctcggcct acttcctgat ttttgtataa gacacatccc agcagcatgg   24240
tagactgaag actcctgggc ccactctcag agattctgct ctggcaagga tgtgtttatt   24300
ggtgagaggg gtgtccagga atacgtgcct ttttttttt ttctagagac agggtctcgt    24360
tgtccaggct ggagtgcagt ggtgcaatca tagcttactg caatctcaaa cttctgggtt   24420
cgagcgatcc tcctatctca gcctcctaag tagctgggac tacaggtgca cgccaccatg   24480
tctggctaat ttttaaattt tttctggagt tggggtcttg tgatgttgcc caggctgatc   24540
tttaacttca ggtctcaaga gatcctccca ccttggcctc ccaaattttt gggattacag   24600
ccatgagcca ctatgcccaa ctagaatatg cactttttt tttttgagac cgagttttgc    24660
tcttgttgcc caggctggag tataatggtg cgatctcggc tcaccgcaac ctccccctcc   24720
caggtccaag cgattcttct gcctcagcct cctgaggagc tgggattaca ggcatgtgcc   24780
accataccag gctaattttg tatttttagt agagatgggg tttcttcgtg ttggtcaggc   24840
tggtcttgaa ctcctgacct caggtgatca gcccgcctg ctttggcctc ccaaagtgct    24900
aggattacag gcatgagcca ccaagcctga ccttttttt tttttttgag acagagtctt    24960
gctttgtcac ccaggctgga gtgcagtggc acgatctcgg ctcactgcaa gctctgcctc   25020
ccaggttcat gccattctcc tgcctcaggc tcccaagtag ctgggactac aggcacttgc   25080
caccacgccc ggctaatttt ttgtattttt agtagagatg gggtttcacc gtgttagcca   25140
ggatggtctt gatttcctga cctcgtgatc cacctgcctt ggcctcccaa agtgctggga   25200
ttataggcgt gagccaccgt gcccggcctt ttttttttt tttttttttt ttgagacagg    25260
atcttgcttg gttgcccagg ctggagtgca gtggcctgat tacagctcac tgcagcctca   25320
atctcctgga ctcaagcaat cctctcacct cagcctcttg agtagctggg accacaggtg   25380
tgtgctacca cacccagata atttttgtgc ttttgtaga acagggttt cgacatgttg     25440 cccaggccgg actaaaattc ctgggctcaa gtgatcctcc tgcctcagct tcccaaagtg   25500
ctgggattac aggtatgtgc catcgtcacc agccagaata tgcattttct ttttttcaga   25560
cggggtctca ctctgttgcc caggctggag tgcagtggtg tgatctcagc tcactgcaac   25620
ctctgccttc tgagttcaag cgattctcct gcctcagcct cccaagcagc taggattaca   25680
```

```
ggtgtctgcc acaacacccg gctaattttt gcattttag taaagatggg gtttcaccat    25740
gttggtcagg ctgatcacaa actcccgact gcaagtgatc cgcttacctc ggcctcccaa    25800
agtgttagga ttacaggcat gagccattgt gcctggccga atatgcactt ttaataagca    25860
tcagccaggc taggcaggcc gggggccaca ctcgagaaca tttgcaccac agccactggc    25920
tacctgcccc ttttttccata aggttccact gccctctctc ccctctatct gggtctgttc    25980
ttcaggttct ccctgggag ctctctgagt gacataactg tccccaagtg ctgggagatg    26040
gagagaggaa tcaccagact ggagcaggcc cccagagcgg agatgggaag gggaggctgg    26100
tgttctgagg ctcccgaggc agtgagaggt gaccggaggc agtgagaggt gaccgaagac    26160
agtggctgag aaccagggag gggctgcggg aaaaagccct gggtgcaagt cgctctttcc    26220
ttagcgtctt tgagaggagg gatggggaaa ggtgaggtac tagggaaaac catctggaag    26280
gaggtcaggc tgcagaaaag ctgcaggagt ctggggact aagaaaacag tgggagaccc    26340
cgctgcagcc cagcacgtga gggtgagaac gtcatgaatg agggaagagc aggcaggggg    26400
tggtggcctt gtggcctctg gagaggagga gccacatgac tctggggtga tctggggtga    26460
ccctcagggt aagggtacct ccctagcact gagtacagag ggaagcctac actgccaggt    26520
gcagtttccc tggcaatgct tctccttcta acactatgtg agtttcctag tgctgctgta    26580
acaaactgcc ataaaccaag tggcttcaga gaacacagac ggactatgac agttgtggag    26640
ggaagaagtt tgaaaagcgg ggtgcccgca ggctgcagtg cttctgcagg ctccagggag    26700
aatctggtcc ttgcctcttc cagcctctag agcctgccgc actccttggc tcatggcccc    26760
gtgtcattgt agcctctgct tctgccatca catctcctcc tctgcctctc ctgcctccct    26820
ctgtccttta taagaacgct tttgagtata ttggacccat ctggatagtc caggataaat    26880
ccctccatcc tcatatcctt aatttaatca cacctggaag gttcccttg ccacataagg    26940
taacatattc acattgggac agttagggga ttgggatgtg acatcttt gaggtgggaa    27000
gaaggagctg gggttctttt taacattttt ttgagacagg gtctctgtca cctaggctgg    27060
agtgcagtgg tgtgattgag actcactgca gcagcctcaa cctcctgggc tcaagtgatc    27120
ctcccacctc agcttcctga gtagctggga ctacaggtgt gcaccaccat gcccagatga    27180
tttttgtatt atttaatat tttgtacaca tggaggtctt ttaatgctgc ccaggctgga    27240
ctcaaactcc tgggctcaag caatcctccc gtcttagcct cccaaagtgc tgggattaca    27300
ggtgtgtgcc accagaccca gcccggacct ggggttcctg tctcatgtca gccttagcaa    27360
tctgggtgac cctgggcaag gccatccccc tctctgggcc tttgttctc cacctgtgca    27420
atgaggctgt tccctctggc tccttcactc tgagttttc agttgggaga atatcttggc    27480
agggagcaga ggtcggcggg ggtggttgtc attccattc agggcctctc agagtcctgc    27540
cgtggtgtgc actgtgtgtg tgtttaattt tctacatttg gatgtgatcc taatccaata    27600
aatgcttagg agacttctat agaatagatt aattttact agaaaaaaat ataattggct    27660
gatgttaagg ctactgccct gacaaatctg ccttggccat atatctgaga aggtaaaaga    27720
cccgctacgc ttgcacataa atatgccatc ttccccacag gccctggaga agcacccgg    27780
ggaggtttcc cttggtgatt tattcttcat taataagctc tatgctatat taggatcaga    27840
tttatgactc tgccttttcta atatttctga catttcatct gaaagaatt acaaatgaaa    27900
tcttgaaact ttgccacttc tccctgctag tgctctggca ctctgtgtcc aagggagat    27960
ggtgggctgg ggagacccca agaagcaggg acagaggcat gtttctcagg gaaaggagcg    28020
atcagcttga cttttgggaga gctttattca gtttgcaagc agcttgggag gtgagcggtt    28080
```

```
caggcgagaa ggctgcagac cagaccacaa gcccagcagc agcagtgatg cctgtaacat    28140
gtatgagatg gtggcaggca cattcattca ttcaacagct atttgttaag cactttactg    28200
tgtgccaaac actgtgctgc ttggtgcttg ggatacagga agaataaaa gtgaagcagt     28260 gatgaagatc ttggccttca tgcatatggt gttctagcag aggtagggga gtgtcaagca    28320
ctgatgaatg aaaatcctga ataggtaaaa tatatcatat gttcacacgt ggtaagggct    28380
atggcaaaac agaaacaaac cctccacaca gggaaaaggg aaccaagagt gccgggtggt    28440
caagttgcaa tgttaattaa gaaagcactt caactcatca actcaaggaa ccgtattatc    28500 cccatttttac agatgaggac ggaggctcag cgtggattag gagctacaca agacacaaa    28560 gggaactttg cacaacttga aagtttgcaa agtgccgtct gagccattag tctcccttct    28620
ccccactgac tgccctacca caatcacatg gggaccataa aaatactgtt gcctgggtcc    28680
cgctcccctg aggctttgat tcaattggtt tggatgcagc ctgggacttg gcatgtgact    28740
cttgtggtgc caggactaag aatcttgtgt gaactcccag cacagcctct caggcctcta    28800
ttttctcacc tgcaagatgt gggtaaaaat attcaccctg tactgcaaga ggatgtcagg    28860
agtgaaggca gaaacacagc accagccctc caggaccccc aaccctccc ccaccccaat     28920 ccttcacccc tgttgtacct tctgacctca aagtggctct gattatttca ctcccacagg    28980
ccactggctc agaggtatag agctcacctg tggcagatgg agatgcggat ctgaggcttc    29040
tgatgctgcc acacccagcg gcgcccccca aattccgggc ccctggatga catctggtct    29100
gttcctgcag catcagagca caatagagcc agccaccagt cccagccctg cctgcatccc    29160
atccattcct gggtgcctaa ccccgaggat cccctggcag tatgatgcgg acctgtcttg    29220
gatcccaggg atatgctggc cacggggagg agccggaaac caacctttgt gtcactgtgt    29280
agtgacaagt gcctttggag gtcacaatag ccagtggtga tttctaccac tgcccccagc    29340
agccaaggtg gcagaggagc cctgtcagtc accccattc tgttcatggt ctcacggtgg     29400
gctccacatg gggggtggca gccctctccc ccacccacc cgaccccttt cgacagatag     29460
ggtaatacaa atacaaataa caccaaaaga ttgagttgct gggcagaaag ggaccaaagg    29520
ccagtgtgtg tgtgaggggt gggggcaggg caggagagga gcagcaaaag gctgtgaccg    29580
cctggctgag cactggatac tcactgaagg gcagggaggc ttcctggaga aggagacctg    29640
gcaggggctg agggagtgat gccaggcatg ggggtttgga gggaccccag gcatggcatg    29700
cctccattcc tccctgtgct atccactcta tataaggggt gctgtgcagg gagacagctt    29760
gcatccaagc agggaggcag ggaggatgag aggcagagag gagcccagct gggttgatgg    29820
aaagtctggg aaatgcagga atccaggag ggggagaatg attccaagct gtggcctgtg     29880
atgggccttg aaaccaggtg taggcacttg gatctgatcg ctggggagcc agagctgctt    29940
cctgagcagc agaagggcag gatgcgaatc agactagggg cagtgggagg aactgagagg    30000
cctcaggtca ccggagaaaa tgcacagggc cggaggcag atgctcct gttttcttgc       30060 tctggggctc aggacagtca gtcaccctga gcttcagact cagctcactc attttgcaga    30120
gatcctgacg gcgatgcttc aggatgatct gggaagagtc aatgaggtaa aatatgtgaa    30180
atatgccttg aaaactacaa accacagcac atgttctgtt tttgcttctg cttgatggac    30240
tcagtgagat ggtggggaca agaattagag aagcccatga ggaggccaag ggcaccaaa    30300 tagacccacc aaggaccagt ggggacttag agaaggatg agtcagagag aaatgacagg     30360
agcagaaggc aggccttgta tggaggatga aggtgaagat catacaccat taaacttgag    30420
aaagaggcgg gaggagctgc catttcttga gtctactgga tgccagcagt agtgctgggc    30480
```

```
aagggcttaa caggtgggga aatcgaggca cagagaggtt aagtagcttg cctaagatca   30540
cccagttagt aagtagcaga gcctggcagc ttaactccaa agtctttgta ctaaagccag   30600
attttccaaa tttgcccaac tgtaagaatc acctgggcct gtaatcctag catttnggga   30660
ggctgaggtg ggtggatcac ctgaggtcag gagtttgaga ccagcctggc caacatggtg   30720
aaaccctgtc tctactaaaa atacaaacaa ttagccgggc gtggtggcag gtgcctgtaa   30780
tcctgtaatc ccagctactt gggaggctga ggcaggagaa ttgcttgaac cccaaaggtg   30840
gaggttgcag tgagctgaga ttgcgccatc gcactccagc ctgggcaaca agagagaaac   30900
gccatctcaa aaaataaaa gcccgggagt ttattacaga tgcatattcc caggcacctc   30960
ctacggaggt tttgagttag tgagtccaag gccttctgcc tcttcccaat gtattcatta   31020
tgcaccatca ttactcttgt tcagatacaa tgtgagtgat agcttgtctc tggcagcaca   31080
gcagccacac ccaaccaatc cagacctcag tcatgagggt gccaatcaca gctaacattt   31140
ttttttttga gacggagtct tgctctgtcg cccaggctgg agtgcagtgg cacgatcttg   31200
gttcactgca gcctctgcct cctgggttca agcgattctc ctgcctcagc ctcctaagta   31260
gctgggatta caggcacctg ccaccatgcc cggctaattg tattttagt agagatgggg   31320
gtttcactat gttggccagg ctggccttga actcctgacc ttgtgagcca cctgcctcag   31380
cttcccaaag tgctgggatt acaggtgtga gccaccgcac ctggcccaca tagctaacat   31440
ttaatcagca catacagggc catgctcatc attttttgcg cacaatgcca tttaaccttc   31500
acaacagcct gtgagaaggt gtgttagcct cattttacag aggaagaaac taaggcccag   31560
agaagttatg caacttgccc aaggacacac agcttgaagg agctgaggtt taacccgttt   31620
ctacggggtc tgaatcctcc ttaccacccc tatctcccct gactcccagg ttgtgtttgg   31680
tgtacttggg tagtgtccag ctgacaaatg agatgtttta gcttcagaca gtctatgcca   31740
tgtagaaatg cacccaggac tgtgcatatt agggaggttt gcaaatgtgt ccacattaga   31800
taattttct caaaatgccc ctcactgaac ttctgtcatg cagtatgtac tgagcacctg   31860
cctcttgcta ggtcccggga gagaggatga agagggcaga gccccaccc tcaggggacc   31920
tgaaaaatgg gagtcctttg tgctcatgga agcagggcct tggggcctca gcactatgga   31980
catttggggc cgggtaattc tttgttgtgg ggggctgtcc tgtagattgc aggatgctcc   32040
gccgcatccc ttgcccctgc cctctagaag ccagtagcac cctccagttg tgaaagccgt   32100
aaaatgtctc cagacattgc tcccagttga gagccacttc attaaagaaa aaaaaataaa   32160
aaagatttct gtatcctcta tacatggact gaatttcact gacatttctc taaataact   32220
gaatctattt ctatactcat tttttttac cagctgccat tttatttatt tttctttct    32280
ttcttttttt aagaaacagg gtctcactct gtcacccagg ctggagtgca gtggcgcaat   32340
tatggctcac tgcagcctcg acctcctggg ctcaagcaat cctcccacct tagcgtcccc   32400
agtagctggg acgccactgt gcccggctat ttatttatt ttattttatt ttttttgtgg   32460
agacagggtc tcccaatgtt gttcaggctg gtctcaaact cctgggttta agcaattctt   32520
ctgccttcat ttcccagagt gttaggattg caggcgtgag ccactgcacc cggccatttt   32580
atttcttaac aaagcacaaa tcaaatgtac aatgcagcta gattttcctt tataaataat   32640
gtctaatgga tttgtttctg tcagctgcct agaacattct ggtatcccag acagaagtgc   32700
aacaccaggt ggaggtgttg cagctgagaa gttctgacca gcataccagc accccttaa    32760
aagctgtcta tacttgcggt tctcagctag gctgccacag aatcgcccaa gtcttaaaaa   32820
aacaggtctc tgtcctactg cttgagatgc tggttctcta ggtctgaggt tctggcacct   32880
```

```
gtgtgttttt aaaactttac aaataattta aaagcgcctt caagtccaca acaacagaat    32940
atttccctcc actcctcatt gtcctggagt tctctaacag tgcagttcta caactggaca    33000
cacgatgtcg cttttcagcc acagttctca ctaagcggcc ccacagggcg gcaggtgcct    33060
tctgcagaga gagagagagg gccttggctg acaggccaag accgggcatc ctggctcctc    33120
ctctgtacag acttttcaca gatgtgaact ctccctactc cctgtcttct gcccccaaat    33180
gaagcctctc agctggcaag agctgagaac taccaagcga gccattgcta atttctattg    33240
tgtttggaac cacaaaaggc agaattatta aggctgtaaa ggacctcaga gcatctggtg    33300
cagtgagttt ccaacttgtg aaaatctgat gtgatctcgg acaagtcact taacccccctg   33360 cctcaatttc ttcatctgta aaataggata ggaatatatc ttgcccgtct gattgttatg    33420
aagacaaaga gaacaaatgc acataaagcc cgtgaccatg tgctttgtga atggaagctt    33480
taatttattc attcatttat tttattattt attttttattt atttatttat ttttgagaca    33540
tagtctcgct ctgttgccca ggctggagtg caatggtgcg acctcggctc actgcaacct    33600
ccatctcccg gattcaaaca attctcctgc ctcagccttc tgagtagctg ggattacagg    33660
tgcctgtcac catggccagc tagttttttgt atttttagta gagactgggt ttcaccatgt    33720
tggccagggt ggtctcaaac tcctgacctc gtgatctgcc cgctttggcc tcccaaagga    33780
agcttttatt tttattatag ttttacataa ggataaattc agccttagtg aagggaagtg    33840
acttgcccaa gatcatacag tgagactgct ggatctgggg ctctacttca gaatttttttt   33900 ttgagatgga gtttcactct gttgcccagg ctggagtgca gtggcacaat ctcggctcac    33960
tgcaacctcc acctcccggg ttcaagcgat tctcctgcct cagcatccct gatagctggg    34020
actacaggct cccaccacca cgcccagcta atttttatat tttgagtaga cagggttt    34080 caccatgttg gccaggctgg tctcaacctg cctggcctcc cagagtgctg agattacagg    34140
tgtgagccac cacgccagtc tactgccatt gtccatgatt tttcctacag ggaaaatcac    34200
aatcccagaa gataagacaa agaacagtaa aaggtggctt tgaggcagt gagttctacc     34260 tgaaggtggg aacagcccag agtgtctggg gacagagtgg taaattctaa tcaagccttc    34320
ccatggcttt gtggatgagg atgagtttct accctgaagc tcggcctgtt cagccataaa    34380
atcaggataa tggtggctgt gcctccttag agtagaatga gaatcagagc agaacaaggg    34440
aaagctgcag tgacttgtca ggtgtcaacc ttcagcatga tgggagagcc atgggaccct    34500 tccccttttcc ctaagagagc cagccctcac agcaggcctg ggatccaatg cccagcaccc    34560
agctgggagc ccagggacct tggccaaaat ctggttctgc ttcaacttgg tgcccggcct    34620
ttgtcaagtc acttcctcat ttgcaaactg ggagagtttg gatgaaacta ttgaatgaaa    34680 ttatttttggg ggtttctttc tggctctcac agtcctcgca tgctcaccat gttcccttca    34740
atttcattag cacagcccaa caaagggtta agcagtggca gttcctctcg ttctttggtt    34800
aggacaggaa ggtcagggt gaggccaata caagaggtag ccgccacagc tgatgctgga    34860
aatgacaata gttctttcct agactcatat ttgtcccctc tccctgaagc tttgcctgca    34920
gtgcccttgt aaagaagttg gcaagaagca ggagtgaggc tcagcccctc tctgaaatgg    34980
atacgccggt tgctcccccct catggctggt ctcatttgcc ttcttcattt ttagacacat   35040
tccaaacttt tcagcaaatt atagtgtttg ccaactggcc gtctgggcc caggagagat    35100 gctatttata gcgatgctgg gatgctgcca tcccagcagca gcctggtaag aaacggagcc    35160
agagtgcctg ggagtggcgt cctgcaccct ggggagaggc cagggccctg gagcagggtg    35220
gcaaagctgg tggcccgtgg caaggaccac tggcacatcc cctgcctgcc tgggccctgg    35280
```

```
ggtctgtgcc catacccac acgggggct gcttccgtgc tccttggaga gacgatggtg    35340
ctgtggggcc actgagcaca gtaaaggcta agacccacca taggtcagcc cttgctcatg    35400
ctgactgttg ccccatttcc cttcattctc tcactcgttc attcctcaga atctgcatcc    35460
tggttttgtc actacctgga gttgtaaaga taccaccaag ctcaccttgt ggtgtgagcc    35520
ttgattttcc ccatctgtgt aaagggtgga tctgagctcc aaagttcctt ctagtcatat    35580
gcagagtgca taataaatgt gttttgtattc ccactgtgct cagtgggcac tggggcatgc    35640
agaagagaaa ttggaataaa tgtgacccct gtcctccaga ggctcagtac cagactggaa    35700
ccaggaccca gatgagggc ctacccagag agggcagcgt gctctcctat ttgtgttagg    35760
cgttaccatt tacaaagggc tttacggctt tgaaggtccc cacaacgccc tgaggaggtg    35820
aagtgtggca atgcccgttc acttgggaaa atactgcatc tcagagagac caagggactc    35880
gcttaaggtc acacagatac agtaagtaag tagggaaaga gctgggcct ctgggctcct    35940 tttccggggc tctggcctcg gttttaaccc gttctcctag acctctcagt tctgggcct    36000 cccctctgtg ttccccaccc ccactttcca tcaagagctc agttctctta agttctatat    36060
tctctcttcc ccacccctag aaatctctgc ccgcttccag aaaaggcttt gattccgtca    36120
tttttggcat ttcccaccca ggaatcaagg ctgcctcctc tgtgaggaag gcgtgtggaa    36180
ggcgagcagc tgaggacacc tcttttaag agaagcttct ccatgttctt agccaggtta    36240
tataacttct tttgcttctt tcttttccac attctacata ttttttcacaa tgaggatgtg    36300 tcacttctat agttaaaaat ggaaatcttc atttaaaaga acaatcagac acaaggcaag    36360
gtatgcttac cttcccaatg accaaggagc agggagacat tggtcgtgga ggccataggt    36420
gaccagcctt gagggaaggg aaggaagggg aggtgcaggg aggcgcagca gaggcacccg    36480
agtgtgctct acgaatgtaa gtctgccagc tgctcctctg tgcctagcac cctggaaagc    36540
gcccgcacac agtgggccct cagcaaactc ccactgagca aagggccctg tgagtaagga    36600
cctagaagca gggtgtgctt gaggcatggg gtgggagggc atccagcttg gctggcggtg    36660
ggagccgatg caaaggtgag ctgagaccag acggtagaag accttcagtg ctgggccgag    36720
gagggttcct tcatcccata gagaagagct gccatccaag acagaaggct ggggagtgac    36780
atgttgaaat cagtatctta ggaaaataaa gccactggct gggccactgg ctcccctttg    36840
tagaggggtc tacgaagctc ccgaggtttc agatagtccc tgagagccct tccctcgcg    36900 atgggctccg tttgaggcat gtccagtgtg aaaggaccac aggccacctg agggacagga    36960
ccaagcagag agctagtgac agaatgccca gggctccaag acagggctgg agaggtggga    37020
gtggtcccca ccttgagagc caaaggggct gagggctgag ggttgaaggc cgagagccag    37080
gaaggtccag gggagcaaaa gggggagcag aggggagct ggaggtgttg gggtggtggg    37140
tagagagcca agatagggag gggacaagag aggggagaat ctcaaggaaa agcaggagca    37200
tgagactgag agaaggcccc tggaacactg gcttgaatgt ggctgacatt ggcactgcca    37260
gtactcatcc caaaccaggg agctcagcca gcgcccttc tgcatgtccg ctctttcatc    37320
agacagctag gaacaagtta tacgagatga tgtccaagtc caataaatgt ctaagtcctt    37380
tccactggat ctggccccag cctcctctct gaaccatctc ctatcactcc accctatccc    37440
tgctggctcc ttctgctcca gccatacagg cttgctcctg ggctcagctt gtgcctgcct    37500
ggggagcctc gcgcttgctg tttcctcctt gagaaattcc tgccctggat aactccttcc    37560
cccacttcct tcagatctct gctccctat caggggcctt ccctggctg ccctatctat    37620 aacagccctg accactcttt tcctcttctc ctgctttctt tgtcttcctg ttcttatcac    37680
```

```
taagacatca cacatgtctt agttggcttg tttatattct gtctccaccc atcttagtca   37740
gctactgctg aaatgatgct gtgtaacaaa ccaccccgat actcagaggc tccaaacaag   37800
tgctgatctt tctcatttgt gagtctgtgt gtcagcccga gcagggcagc tccaggctat   37860
ggcttgggtt tgggtggact ccatgtctct ctccattctc cttggaccag cagctccctg   37920
gggcacatgc ttgtcttgga gaatggcagg aacttaaaag ccaagccaaa cctcacagca   37980
cggttaaggg tgatcatgac acaccgctaa cattctagtg gccaaagaag tctcatggcc   38040
aagtgtaata gcagtggatt gggcaagttt actctcttac acctgttgtg aaggggagtg   38100
ggaggggatg ggggggtgac cgttttcaca acaacagtgc aaactatccc atctcccaat   38160
agaacataaa caccttaagg ttggaactgg gtctgtatcc ccagcactta aaatagtttt   38220
tggcatacag taagggtgca atagacattt gttaaataaa tatacagact aaccaattag   38280
cataatacag atgacaaagg tgtctctctt ctgccagctt ctgtgcctga aatgttgatg   38340
atctcctccc tatcttccta acatctctcc tgtccccacc tgtccatgcc cagggtttgg   38400
ctgctgtgac agaagtgtga gagcctcctg tctcccttgg gatcccagta agagcttcca   38460
tgcctctctc cctgctcacc tgggctccca tccctgggga ccttctggaa acagcttcca   38520
gggctcccag agcttactta gccagattct acatctggct ccagctgtta tcctaagctt   38580
ggccttgttt tctgatctga ccacagcttc atcactccta cctgactgtg ggattctagc   38640
ccccagtggg gtgggggacc aagggtgaca attacctggg accttgacta ttgaaaggct   38700
aatcaggttt gattgggaaa aaagagttgc taaaaaggat tgtattggat aattggtgag   38760
atttgaacat ggattttata ttagtattgt gttattacat tttctgatat tagtcattct   38820
tttttttttt ttttttgac ggagtttgct ctgtcaccag gctggagtgc aatagtgtga   38880
tctcggctca ctgcaacctc tgccacccgg gttcaagcga ttcccctgct tcggcctcct   38940
gagtagctgg gactacaggc gggtgccacc acacccagct tgtttttgta cttttagtag   39000
agacagggtt tcaacatgtt ggccaggatg gtctcgatct cttgacctcg tgatctgccc   39060
gcctcagcct cccaaagtgc tgggattaca ggcatgagtc accgctcccg gccgttagtc   39120
attcttatag gtatgtaaga aaatgtcctt gaggtattta gcagggaagt tcatgatctc   39180
tgcagcttac tcacaaatgg ttaaacagaa tgagactaag aacagactag taagaaaaga   39240
ctgaagaata taattattag gccaggtgca gtgactcaca cctgtaaatc ccaacatttt   39300
gggaagctga gataggagga tcacttgagg ccaggagttt gagaccagcc tgggcaacat   39360
agtgagaccc catctctaca aaaaaaaaaa aaagtaaaaa ttacgtgggc acggtggtat   39420
acgcctgtac ttccagcttc tgggaggct gaagtgggat gatcagagga cctcaggagt   39480
ttgaggctgc agtgagctat gattgcagca ctgcactcca gccagggaga cagactgagg   39540
cccggtctct aaaaaaaaag gaatctatgt gagtctatat attcgtgcaa cttttctata   39600
ggattgaaac tctttaaaat aagcttaata ataaaaacaa aagctggtgg gtgagacctt   39660
tcatgtactc tccaggagag ttaagccccc caacattcct gtccccttgt ttactctcaa   39720
gcacccctc ccccacccaa ggaccaggtc tttgtttact gagcatctca gcgatgagct   39780
ctcaccccct gatttcatca attataaatg tgctcgctac tcaccacacg gcaatttgtg   39840
acggactgtg gttgtggtg agagtagcac catccaagtt caccgcagcc gcgagtagag   39900
atgagggttg gggccagaca cagggctgtg ggggcggcaa gggcacgcag gcagccctgc   39960
caccttcctg tttgtcagcc aagtgaggct tccgagggca gcgggcgagc gggtcactac   40020
tcagggccag ctactgcggc caggccaggc tagtcaggtc tgtgcagcca gaactagagg   40080
```

```
ctccgccagg atgtgaggtc tcccagctcc tgggaactga agcaaacact ctgactaccc   40140
cttcttgaag tgccttacgg tgtatacatt tgtttaatct gcacaacaaa cctaggagca   40200
gttattgtta ctgtcctcat tttgcagatg aggaaactga ggcaaagaga aattaagtaa   40260
ctccttcaaa gtctggtaag tgacagaacc agattttacc ctcttactca ttgtccatat   40320
tgccgagtaa cttacattaa tagatactat gcatgtttat tttatttttt atttttttt    40380 agagatgggg tctcattctt ttttttttt tttttgaga cggagtctcg ctctgtcgcc     40440
caggctggag tccagtgggg cgtgatcttg gctcactgca agctccgcct ccctggttca   40500
ctccattctc ctgcctcagc ctcccgagta gctgggacta caggcacctg ccaccacgcc   40560
cggctaattt tttgtatatt tagtagagtc ggggtttcac cgcgttacca gtatggtctc   40620
gatctcccga actcgtgatc cgcccacctc ggcctcccaa agtgctggga ttacaggcgt   40680
gagccaccgc gcccggtcct cattctttca ctcagactgg agtgccgtcg tgcaatctca   40740
gctcactgca gcctcaactc ggggctcaag caatcctgcc acctcagcct cccgagtagc   40800
tgggaccaca ggcagtgcca ccacacccaa ctaattttg cattttttgt agagaccggc     40860
ttttgccatg ttgcccaggc tggtctcgaa ctcctgagct cagacaatcc acttgcctcg   40920
gcctccaaaa gtgctgggat tatagcacca cgcccagccg atactatgca tgtttaactg   40980
acacctaatg attaggtagc aacaatttct tggctgcctt attcaccttc atgcccca     41040 acattgaaaa tgtcttttcc catgtgaaag catttgtggg ctcctactgc caatctataa   41100
agtagaaatc cttctgtggt acaaagccct ctttcttatc taatttccca tttcccgttc   41160
ccccttcccc cttctgctaa gagctcttcc ctacccacat tgtaagtagg gccggggagc   41220
taactccacc ttgcgtactc caaatcaacc acatgaccca ggcctgacca atcagggctc   41280
caaatcctct agctatagtg attggtttag ggagggacat gtgacccgcc tgagccaatg   41340
aggatctgtt ctgggactcc tgtttgaact cttgggaaaa taaactcctt atgttgggtg   41400
gctgagggga tgaatgtgag ctgggagctg caagcaggca tcatgctatt cccttcagct   41460
ttcaagtagt gttttcactg ctgttaacaa ttccaaatct taagtgttcc ttgcatcttc   41520
ctctcgccaa aaatattaca gtactggagg gcttacatgg tgtctcaaat gtctggagtt   41580
taaatctgcc ttgcagcttc catggccaca gtgagtgtct gagtcctggc cgctttctgc   41640
tgatcccggg gagagtttag cctgcctgcc cttcctccct ggttcgttct catgtactca   41700
gatccctgcc tcactcttct ctcacacaga caacaaaaga gagtcagatt gtggtcttaa   41760
gtgcacagga ctctgaagtt aggaccgaaa gaccttggtt agagtctaaa ccttgtcagt   41820
taccaaatat cattaggcac attagttaat ctctctgagg cttatttccc catcagtaaa   41880
gtgggtactg ctgaagatgt agtctttaga agtgttctct agattgtaag ccccgtgctt   41940
cctggttatt gactaaacag ggataaaaat gagtttctcc tcacctgggt gtcattgagt   42000
ttctggtcat tgtgagatgg gtgatgaagc caagggcatc aaacatccca acgaggctgt   42060
tttctgcatc tccagggcta tcccagcgtt aatcacatat ggacctttaa tcagagtttg   42120
cagaataagt gagaattgtg ttagagtatg aatgtagata ttatcttgtt ttagtcattg   42180
ttactctagg ggaccattct tactacagga atattgcaca aaacccagaa atttattgac   42240
tttctcctaa ccaaggccta aagagctggt gttagacata ggccaaggcc agccagaggc   42300
ccaaagcctg tttcccaggg taggactgcc ctggcctccc cctctttctc cccaggctcc   42360
accccagaga gctgaagacc aggctgggta cggcactgct gagaaactga ggaaaaggcc   42420
actggcctcc tctctcactg caggctgccc acccgggagg gggaaagctt gtcactaaat   42480
```

```
caggttcagt tttggtcact gtcttggact ggatattcta gcatcagaac tgagatgttt    42540
cttgtgactt aaagtaactt caggactcta ttctacctag gattgggcag aaaagttatg    42600
ggcctgcggg agttccaatt cagaaacagg ggagattact tgcactaaag aaagtctaaa    42660
ggaaggtagg agacaaaaat aaagttgtgt attgatgatc ctaggagtta tgcttgtttg    42720
acataccagt tatacctgct gtcacggtag ttatgcatta ggggacccag gtgtctgaag    42780
ttatatccag aagacttctg agggtgcacc ggggggtccc ttggctaaaa gtgtgattta    42840
aaccctaaga gcctgcccag actatcagtc ccagtttcta cgtccactgt ccctgaatct    42900
cgctgcttct tccttaggct gctgggagtc tgaaccctcc ccgccaaca cccctccccc     42960 atgcctcagt cgtgggaagg gggggccctt gagcagtagg gccaagccct gttcagcctg    43020
ggaccaagtt cccatcaaca aggtggtctg ggcagtggcc agccagaaag cagtaattac    43080
tgtcgaggtg cagggacccc aggtagggcc cccacctccc acctctgtgt gggcagtgaa    43140
tgggcctgcc cctgggtaag gctgtgtcag caggcgcctg cccacccctt gctgggttcc    43200 caggcccta gagccctctc gtaataggag ccatttgcgc tgtaaccagt gggtgaccag     43260
atttttaatc ttggagaccc cttggatccc aggcgggaag tgggatttgt caaatgggga    43320 gaggcgggc tgtctgggaa tgccagacgg ggttgtgctg gggaaatatg tctcctttcc     43380
atacagcccc cttcccatac ctccagcctc cctctacccc gcaagtcagc tctgtagctc    43440
ctaggaggta tctccaacat gcttagctgt tgaaagtaaa tgaatgccgg aagttgaaat    43500
ctgaatggct tgttttgcac taactcaggt gcatgccaaa tagggtgtc tctttgcttg     43560 atcctaatcc ttcctcctct gaaatccttt ctgacctgct gcctatcagc aattgccctg    43620
caaagaccct ctagctggcc gcgggagaag ctgtgttctt ggctatcagg agtgagaaca    43680
ctggacccaa gcttgcctat tctctgccac aactcactgt gtgatcttgg acaagtcact    43740
tcctttcttt cagcctcagt ttcaggagac ttggcacttg ctgagtgcca atgtgtgcca    43800
tgttcttgac aagtatggtc ccacacaacc ttgccaatga ccctgtgacc tgtgtcttct    43860
tgttcccagt ttacaggaga aagatgcag cctgggagag atgcagcagg tgtctgaggc     43920
cacacagcaa gtcacccagg gccaggatct gaagctgggc tctccagct ccactgcctg     43980 ggcactttct cctccacagc gaccttcagg tcatcatgag gagcctttcg gactaaagct    44040
agagagctgg gattccaaca gttcagcaac ccatgacttc tccatggcag ctgctgcctg    44100
accacctagt gcctttccac taagattgtt ccttccctct cctgaagatt atcctcctgc    44160
ccctctctcc caaacatctg cggtgtgcac ctgctgccca agttgaact tttttttgtt     44220 agagacaggg cctcactgtg tcatccaggc tggagtgcag tggcgtgatc atagctcact    44280
gcagcctcca actcctgggc tcaagtgacc ctctcacctc agcttcctga gtagctggga    44340
ctacaggcat gcaccaccac gcctggctaa ttttttaaatt ttttgcagag acagggtcta    44400
gctatgttgc ccaccctggt cttgaactcc tgggctcaag caatctgtct gccttggtct    44460
cccagctcgc tgggattaca ggcatgaatc accatgcccg gtcctccaaa gttgaacttt    44520
tgagactcag tttccttctt ggtaaattca ggctcctagg tgctacctcc tcagagacat    44580
cctccttgac cacatcacat gacctctcgc agaggccaga ttctttaatg tattcatttg    44640
tctattatca tgtttcccca gtagaagttg cacaaacggc aggggcttca tctgttttgt    44700
ttgccgttat gtccttagca cctaaaattg tgcctggcac atatagtact cagtatgtat    44760
ttgctgggtc aatgagtgag tgaatttata ctaataacag cagctaccat ttctagagtg    44820
tttaccatat attgggcact gtgtcagtct tcccaacaac ccacagacga agatcaatta    44880
```

```
ttacacccat tgtacagatc aggaaactga gtcaggttaa gaaacttgcc ctaaatccta    44940
cagtctcact tagaacttct gactgcagtg ctcatcagaa tgcattgtca acccaaaggt    45000
catttccagc tcaggtggct tctatcaaaa gagctcatcc tggccttttcc aagagccaga   45060 cctccgacat cggtggagcc ctgtgcatag ctggcctctc ctgggcgtct tgtcccaagt    45120
acagagacct ggatccttttc ccactcatgt gcaacagccc aaaattaaaa acaaaagcca   45180
tattaaaaaa caaaaccaac tttctgcctt aaaatattgt gagccagggg caattagca    45240 attatgctgt attttattat gagaagatag aattctaatt ggactgattt gaattccaca    45300
cacctccaca gattgttttg ggaattaagg tatcagttgt atcggtaatt atggtttacc    45360
attcaattac cccccacag aaaactgtta aattgtctgt gacggggctt aaatttagct    45420
cagacctatg tcctatgaag actgcgcgag tcaatacaag ccatccggaa accaccgggt    45480
gccctgtgcc aggcggtaat taggggttga ggtttccaaa gttttacctg agacagcagg    45540
gacaagtgcc tgggctgggc gtgctcacgt ggggggggctt ggatgctccc ccagcacagt   45600
gctcttggct cctgccctgc gttgctggtg caatagctga tcatctggaa gacaatgtgg    45660
tttcagccgc aagtgacatt ttggcgaggt gcaccagcat agaagccctg agacagcgag    45720
ggaccatgta aaactcacgg acattgtaat tggacacatc tgggattgaa ttcccactct    45780
tccacttagg gagtgaactt gagagggcca cttaatatct ttgagcctct gtttccccac    45840
ctgtcaaatg ggtacaccct ctgcctcaca cacgggttat tgtgaagatg gatggagaat    45900
aataatggtg cctggcccaa attgcatttt tttctctttt tttagtactc actacatgcc    45960
agatacttta caaacatctc taaacctcct aagcccctata gggcaggcac tgtggttatt    46020
ctctgtttta tggatgggaa aactgagtcc cagagaggtt aaataacatg ccgaaagtcc    46080
catgactatg aaatggggca gctgggatcc aaacccaggt gacctagggc caaaccctaa    46140
gcatgaagct gccctgctgg gtgccttctg tacctgtccc tctaagtgga agtgcctaga    46200
aatgacccag ccaaaagcag cagactgtat tttatcattt caacaattct ctctgtccat    46260
aaaaagttct atgcagcttg gccagttcct ttttcctgaa tacaaaactg agaatggtaa    46320
cagggaactg actttttaat gtcatggtgc aaaggagcta gctctgccat gacctccttg    46380
aagtgacctg gtagagtgag ggtaagacaa gccacactcc ctaggctatg gaggccactc    46440
tccatggaga taggggaata gggaatcctg caaaatacag tctctgggga tgggaaggat    46500
cagggaaggg gccaggtgca gtagctcatg cctgtaatct cagcatttcg ggaggctgag    46560
gtgggaggat cgcttgagcc caggagtttg agaccagca tttgagacca gcctgagcaa     46620
catatcaaga ccctgtcttt acaaaaaatt aacaaaaagg ccaggcgtga tggctcacac    46680
ctgtaacccc agtactttga gaggccgagg tgggcggatc acctgaggtc gggagtttga    46740
gaccagcctg gccaacgtgg tgaaactccg tctctactaa aaatacaaaa attagccagg   46800
tgtggtggct gtaataccag ctactcggga ggctgaggca ggagaatcac ttgaatccag    46860
gaggcagagg ttgcagtgag cccagatcat gccactgcac tccagcctgg gagacagagt    46920
gagactccgt ctcaaaaaaa aaaaaaaaca attaacaaat tagatgggtg tggtggtgca    46980
cagctgtagt cccagctact caggaggctg aggtgaaggg atcacttgat ccaggtgttc    47040
gaggctatag taagctgtga tcaccccact gcactccagc ctgggtgaca gagtgagatc    47100
ttgtctcaaa aaaaaaaaat tttttttttt aaaggatcag ggtaggtaca tggactcctc    47160
ctattccttc tggcaccatc agtggttgaa cacacaaact ttggttcaaa tcctgcctct    47220
tccaatttgc tagctgtgtg accttgaaaa agttacttaa cccctcttat ccttagtttc    47280
```

```
ctcatcttca gaataaaaat agtgcttgcc tgatggggga gatgatggat gtaaagggcc   47340
tcatagaggg cttggcattt accaagtgtt tgagaaatat tggctgtttt tattcaaggc   47400
ctgctcattg ctagcatgag ctacctgcaa cagccacctc taggcctctt ttgctcccta   47460
tagtccagcc acaccaagaa accatgatgg cctgaatcct ctctgacttt gtcaggcctc   47520
cgtgccttta tacatgctgt tccttctgcc tagaaggcct ttctcttttt tcaacctcct   47580
tgagtccatt ttagtccctg ccagatggtc acttctctgt gatgctgccc taactccttg   47640
gcagccatgc tgctcccttg accattcact agccccttta attcagcccc agccacagtg   47700
aggattaaat gggatgatgt ctgagaaagc ccatgggcaa gaacctggca tggagtggtg   47760
ccccataaat gatgaatgga gctggggttg ctttctcagc cagctgcctg cagggggcct   47820
ggcttcctca tcttcacacg tcagtgccta gagtaacacc tggcacacag tgaacacaat   47880
ctcagtaact gttagacatt tgtctttggg ggagctgctc agcctcccac attgggtgt    47940
gggttttttg ttttgttttg ttttgttttt tgagacggag tttcattctt gttgcccagg   48000
ctggagtgca atggtgcgat cttggctcac tgcagcctcc gctgcctggg ttcaagtgat   48060
tctcctacct cagcctcccg agtagtagct gggattacag gcacgtgcca ccatgcctgg   48120
ctaatgtttt gtattttag tagagacagg atttcaccat gttggtcagg ctggtcttga    48180
actcctgacc tcaggtgatc cacccgcctt ggcctcccaa agtgctgaga ttataggcgt   48240
gagccaccac gcccggccta ggggtgtggg gtcttttacc gactaggcct ggtgggggaa   48300
gtcagggacc ccaccacaaa agttggagag gccacatcct cccacctcca tctgggtta    48360
gacatgtgac ccaggcttgg ccaatcggat gttcctccat cttgcccaga attcacactc   48420
agcagtggtc ttcacgaggg gtggtagtgg tggccagtag gagcagggct gggcagcctc   48480
cctaacccac gttcatgaga cttgaagctg gctggtttcc tgtcccctgg cctcccttgc   48540
ccattcccat cctggtgctc cctccctatg gactcctttt gctcataaat atccctccaa   48600
ttaattgctt tgctgcttct tagctagtgt tgtttctgtc acttgcaacc aagagcctat   48660
tcaggtgcag gaagggttga atgaacaatg gaaatggatc aacacatgtt tctgagcatg   48720
tgctgacagg caggccctgg gcggagtacc acggtgttca aatgatgtgt aagatgtggg   48780
cagtgccccg gggggtctat ggggagacag accatgcatg acatcataaa caagaccaca   48840
gggtttagtt ggaccttgca gacacccaga gaagacgact ttgagccctc attggatggt   48900
gccatcgcaa agtacaaaac gaattgggtt gtaggaactg gaggcactgg gacaatattc   48960
cagattaggg attgagctga aggggttgga aatggctgag tagggtggtg gaaagggatg   49020
cctgctagta ggcaattgtc ttagtctgtt ttgtgctgct gtaatggatt accacagact   49080
gggtaattta taacaaacag aaatttattt ggctcatggt tctgaaggat gggaaatcca   49140
aaatcaagga gccggcatct ggtgagggcc ttcttgttgc atcataacat gccagagggt   49200
gtcacatggt ggaagggcaa agagagggag aaagggaaag agagggagca ggaaagggca   49260
aacccactcc catgataata agctcactca tatcatgagt cattcatcca tcgtgagggc   49320
agggtccacc tcccaatacc atcacaatgg caactaaacc tcaacatgat ttttggagag   49380
gacaaacatt caaaccatgg cagcagcgtt tgtgggaaac acgcgccaaa gcaagaaaag   49440
accaacctaa gagtgagtga cttggctcct cattctacat tcattttcat ccaatggggc   49500
ccaagggcat gtacccatta cccatctggg cagttccctt gaatgtgggc ttctgtttgc   49560
ccgtggaggt gaggaacttc aaggaagaaa ccatgaaaga cctcttgagg ctgagggctg   49620
gcaccagcac caagatctcc aggcagctgg aacagtgatg gctcctccgt cctcgcaggc   49680
```

```
ggggcaccca acagggtgtg accgtcacct gaggggagac agccagaggc acaggcctga    49740
tcctgggact gaggttggcg gtttgggtgg agaggtgatt ctgagtgtga caccctccag    49800
tgataaagtg gggggcttcc cagcagcccc tggggaaaca ggctgcatct ctggagacag    49860
gagatatgtg gaggcctgag gggcagtgga aagccctgtg tgtctgggtc aggtctctcc    49920
ttggcaggta atggtttgtc ccagtagttt tcagactccc catcctgccc tgtccttctc    49980
ctgtctgatg ctcagacctg tcactcccag ctcagccccc accttactgt ctaccccctca   50040 gagtccctcc caccaagggc accttctgtc ccacatctcc atggtgcagt catgggagga    50100
gaacttggga gcataagaaa ctccaccaag ttggggccag gcatggtggc tcacgcctgt    50160
aatcccagca ctttgggagg ccgaggctgg tgaatcacaa ggtcaggagt ttgagaccag    50220
cctgaccaac ataatgaaat cccgtctcta ttaaaaatgc aaaaaattag ccgggcatgg    50280
tggcaggtgc ctgtaatccc agctactcac gaggctgagg caggagaatc acttgaaccg    50340
ggaggcagag gatgcagtga gccaagatcg cgccattgca ctccagcctg ggtggcagtg    50400
aaagacttgg tctcaaaaaa aaaaaaaag aaagaaagaa aaaaaagaa actccaccaa      50460 gggcttttgg gtcctaggga cagcaatgat gtggctggtc cagccagaac ctcattttgt    50520
cagtaaagtt gggacccata ttccctaaga gatttgtccc aagaacacat gggttgctac    50580
agcggaggag aaatcaagtc tgttttccct ctggtgaatt gtcccctgaa cgtgctttct    50640
tcctacagtg ttgccaggaa agtaaaaaaa aaaaaaaaa aaaaaaaaa gtccacgatg       50700 tcagctgggg tgataccaaa acaattgtgg gaggaacaac atccgcaaat tgaatagtgt    50760
gaggagtgtg gacagaagat gttttgtctt tggcctcatc tcccagactt gatctttgta    50820
aatacagaag tttccaccag agccgaacct ggcaatgact tgaggagcag ctgcaaggaa    50880
gacagcctct cccagggtat cacctggggg cacaccccag cttcccctcc tgagcctcat    50940 cgagggggtta gtgctacctc tcgggaaaac ataaagatga caagaagcca aaggtgccaa   51000
tagttcccat ttagtataaa agctggctca gcaaatcatg ctatttcagg gcctagggtg    51060
ggccagttcc caggcagccc tggcaggaag gactctgaga ggcggacagt aaggtagggg    51120
cttgggagtg ataggtctaa acatctgatg gaagcaaaag ggaggacaag ggaggagtc     51180 aaaaaatccg ggaagcctgt ccttccagaa agtaccgaca ccagggtgag gtggatccca    51240
gcacccgcac ctctgaatgg cctttcccct gcaccctat cccgccccca ctcggagcta     51300
ccccaagcac ctgttcctct gggcccaag gtgacgccct tgtgtgtgt ataggaaagg      51360 acggtgtaca catttggtta gttccttctt ttacaccata aattatcaga gacaacccctt   51420 ttggaaagca atttggcaat aatatcaagt gacataaaga tgttcatagc ctttggccca    51480
ataatcttcc tcctgggaat taatcctaag aaaataattc acaaggaaga agaaccatt     51540 ttgtatctac aaagacattt attggggtgt tatttatgat agggaaaaac tggagacacc    51600
ctccccagcc aacatagagg gatggtccta taaattatga tacatccatc caatgaaatg    51660
ttaccctgcc agtaaaaatg gtaaattgaa aattgtgtag caacaagaaa gagtgttcag    51720
aaaataaaag caagtgaaaa aaggagcaca ggattgtcta tatgctgtga tcaatggcaa    51780
tgctgacaaa tccatgtatg tgtagatagt tgtagtgtta cctgtaaggc acgataaggc    51840
ggatgtaact gtgcttcaaa tgttcttttc catagctgtg gagtccttct agtatgaaat    51900 cattttgta aaatcgcaat ttgtcaccag gggttttgac tttccttatt gcctcgtggg     51960
aggtggcaga ggcagcacat ctcagaccga gcctcggttc ctccccctac ctcccaccgc    52020
tgcgcttgaa gaaagatgct gcagcctccc cagtccccat gccagcgctc ccacttttct    52080
```

```
ctgagctttc ggtggcagac agcgccttgg gcacttttc atgctcataa ttcgaattac     52140
ctgtttaagt cggtcaaatg aaaaaatacc agctccgccc ccacgcgggc tggccggggc     52200
gcctggagcg ccagggcggc tgcagcgcgc tctccgcggc cgtcggccct gagctcattt     52260
cctggggcgc gcgcgccggg ctatttcagc ctggcgctgt gcaaacagga caatttactg     52320
cggccaaaag ggacccaaat tacaatcgta tcacagacaa atatccgcca cgccaggtct     52380
ccaggggcca ggaggggcct ctctcccggc gcgggggcg ggcgcggggt caggcaggtc     52440
cgcggggctc ggctcggcct cgccgtgccc tgatcggcgt ttgccaccga gctgtgcctg     52500
ctctctgcaa caggaagggg cccagctccc ccgggcgacc gttcctatct gagttctcgt     52560
tcctatctgg gttttcgtgc agaaaaactt catctcttcc cagggatttt cccctgattt     52620
agggtcccct tttatttggt ttcttttcag cacttgggat gaaaacatcc ctccatccag     52680
ccactccagg gctcaaagtc atatctcctc gttcagaaac ctcagtgcct gtccaccact     52740
cttccggaaa agtcggaatc cttagtgtga tggtcaaaga ccgctcttag tccagtccac     52800
ctgtccaggg ccagcccctg tacccagatg ctccaaccac ggagagcaca tcagactttc     52860
acaattttat ccttgacaat tgccttttca tcctgcctaa atgttccctt gtttctttct     52920
gcctagtgag ctcttattcc ttctttaaga cccagataca catcacctct tccatgaagc     52980
cttcccagac ttccccttc cctgcttgac atctgccttc caagcagagt cagccccttt     53040
tccttcctag caccgtgcag aggtagatgg tacttctcac atcctgtaat taattgcttg     53100
catgcctgtg gtacaccgta ccattgctca caaatatttc ctcttcctct ctggagaagg     53160
attacacttc cttgatccat tggcctcact caggcttcgc cacatgactg gtgctggcca     53220
gtgaagtggg acatgtgagt tactggggag cagaaacttt caaagccaag catggctcac     53280
cttgttctct cttccctctg ttacaaggat ggcagtgccc cagccagaaa ccacactgcc     53340
agcctggcat aggagtggag cagggcacac ataagtgtga gagaaatgaa cttcacctca     53400
gtgctcgagg cccctgggac catggactca tttgttactg cagcataaac tagctggtct     53460
tgacttcagc ttctgcctct cttccctggc tttgccttca caaaatcaag agtctgatct     53520
tactcatatt atagagctgg tcttcaacca tgttctttt tttttttcc tttttttt     53580
tttgagatgg agtttcgctc atgtagtcca ggatggagtg caatggtgcg atctgggctc     53640
actgcaatct ctgcctccct ggttcaagcg attctcctgc ctcagcctcc caaatgctg     53700
ggattacagg tgcttgccac cacgcctagc taatttttgt attttttagaa gagataggat     53760
ttcaccatgt tggccaggct atctcaaact cctgacctca ggagatctgc ccgcttcggc     53820
ctcccaaagt gctggcatta caggcatgag ccaccatgcc cagccccatg ttcttcgaat     53880
ggccaagaat atcagtaggt aaggtttgtt gagcatggat tgtgtgccag gtgctgtgct     53940
atgcctttgg caagcgttat cccattacat cctttaacag cactctctgg tgggtactgc     54000
tcttatacaa gatttacaaa agagaaaaga gactcagagg aatgtagggg ctcacgtgag     54060
attgtaaagt agtgagaagt ggagctggtc cttcagctca aatccctctg atgccaaaga     54120
actcaaactc tgcagttcca tcatgtgcat cctcactctc tcacttcctg cagaggatct     54180
gtggaggttg taactattgt tttcacctgt ctcttccact gggctctgag ctgcccgaag     54240
acagatcttt tttttttttt tgagacagaa ttttgctctt gttgcccagg ctggagtgca     54300
atggcacgat cttggctcac cacagcctct gcctcttggg ttcaagcgat tctcctgcct     54360
cagcctcccg agtaactggg attacaggca tgcgccacca tgcctggcta cttttgtatt     54420
tttagtagag acggggtttc tctgtgttgg tcaggctggt cttgaactcc cgaccttagg     54480
```

```
tgatctgtct gtctcggcct cccaaagtgc tgggattata ggcgtgagcc accacgcccg    54540
gccccgaaga cagatcttaa tcatctgatt tcccatccat taattcagtc tttcaccaag    54600
gatgtattga gtgccaatta tatgccaggc atcatctgat gtgttgggga cagagaaata    54660
aaacagataa aaatccctgc tgttaattct agcctatggt gacaagaagc agatccgtgg    54720
ctgcctgggg tgagtgtggg gtaggaaatg ggagaaatgg ggatgactgc aactttgggg    54780
gtagtggaaa atgttcagta tcgtggtagt ggtggtggct gtacaggtat atatatccgc    54840
atacatccca cagttcagaa ttatacactt taaatggtaa atggatacag tttattatat    54900
gtaaatgatc cctcaattaa gttgatttag aggaacctgg ccgggcgtgg tggctcacac    54960
ctagtattct cagcactttg ggaggccgag gtgggcggat catgaggtca ggagatagag    55020
accatcctag ctaacatggt gaaaacccat ctctactaaa aacacgaaaa caaaaaatta    55080
gccgggtgtg gtggtgggcg cctgtagtcc cagctactcg ggacactgaa cctgggaggc    55140
ggagctggca gtgagctgag atcgcaccac ttcactccag cctgggcaac agagcaagac    55200
tctgccttga aaaaaaaaa aaaaaagaa cccttgctct tatggagaag cattctactg       55260
gggaaaacag acaataaaca catagataaa taaaacatat gtcagaaagg ggtaagtgat    55320
gctcagaaaa ataggacaag ggatcagaag tgctaggcgt tgcaatttaa aataatgggg    55380
tctggaaagc caccctgaga agggccaatg gagctatgcc cagcctgtgg tatccttcct    55440
caggcagggg actgtaccc cagcttacaa gccttttcga ggcaccttca gggtttgagc     55500
ccaaaatgca ctgcacatta agtgttattg atgggcttgt ggaaatctgc tctccgtcag    55560
gctctgatga aacttttcca acaggagact gaactcagta ctgggcatgg cccctgcac    55620
atagtaagtc cacagcaaat gtgtgtgggg tgaatactgt cttctttatc ctcccttttt    55680
ctactccagt ccaggtagac ggtgtatcta cccacccaat tttgctgttt ctggtaccct    55740
cagtgggtct tgcctgctct tcctccttga aatcattact cagaggtctc cgtgtcagct    55800
ccagacagat gggcctggtg ctcctttatc tcaatacaat tcccccgctc ccaggctcca    55860
ggggaaatcc tgagctaact ttggtctttc ctaaactcca cacttccctt tgggcacctc    55920
tttcccatt gcggggctcc cttcagaat ttgctgcttt atttatttat ttattttgt         55980
cagaggtgca ttaatgatgc tttatttaaa aacaaaaaac ttggccaggc gcggtggctt    56040
atgcctgtaa tcccagcact tgggaggct gaggtgggcg gatcacaagg tcaggagatc     56100
aagaccatcc agaccaacat ggtgaaaccc agtctgtact aaaaatacaa aaaaaaaaa     56160
aaaaaaaat cagccgggcg tggcacatgc ctgtaattcc agctactcag gaggctgagg     56220
caggagaatc acttgaaccc gggaggcaga ggttgcagtg agccgagatt gggccactgc    56280
actccagcct gggtgacaga gcgagactcc atctcaaaca aaaaacacc acaaataaat      56340
aaaaaataaa aacaaaaaac caaaacagt ccattccatg tcgtgttgaa actgatcagt      56400
gtaagttaaa tggtggtttt taggctggac ccatgattta agctgtaccc atccagctca    56460
aactgaaaaa aaaaaaaatc atttgaatgt taaagcaatc gttcagagtc ttcaagaaga    56520
aaccaggcag gaaaatgcca ataatgatga ctggcaaaat caaaatctaa aacaaataaa    56580
ctgtttatca agctgccgac agaaaaagaa atcttgcatg gagactacaa gtctggattt    56640
tctgggatga aattgtacag gaatctcagt ctacagtttc ctcaatcgct gtggagatgg    56700
agctgtcact gaatctgaca gagccctgca ctccccagtc cgccgaccct ttctgtaatc    56760
cagtcttcac tgtagcctga ggaactattt caacctgctc cttttttatc ttcttctttg    56820
gcacaaccte agtggactte tetgattcag aacaagttct aattgatctt ctctgttget    56880
```

```
tcttttctac tgagcctgta gaaccagatg ttgcttcaag agatgatata ttctgcattg    56940
gcttttcatt tctctggttt ggtttagaaa ttataagcct gtcttgcccc ctgacactta    57000
tttctgtttt gttaccaatt ccctttgttg aataaacaaa ttaatttccc atcctctgta    57060
gcattctgaa gagcaaacac ttcttcaatt ttcacagctg gagacatgtt acacttctgc    57120
aaatccaggc tcccttgtg cattgtaatg gaagctggta ggatttcctt gctgccacag     57180
ttttccaggc tattttaaca ggaggtggct cttcctcgtc cgcgcttgtg tgctgcctcg    57240
ggctgtgtct ccaaatgtca gtacttgaga gtgaggaggc caccctcccct gcattgatct   57300
gttctggctg agtttaaagc acagatcttg gtcatcaggt tttttaact tcggctttgg     57360
agacaacatt cttttttttt tttttttttag atggagtctc gctctgtcgc ccaggctgga   57420
atgcagtggg gcgatctccg gttcatgcca ttctcctgcc tcagcctccc gagtacctgg    57480
gattacaggc gcccaccacc atgcccggct aatttttttg tattttttta gtagagacgg    57540
ggtttcaccg tgttagccag gatggtctca atctcctgac cttgtgatcc gcccgcctgg    57600
gcctcccaaa gtgctgggat tacagacgtg agccaccgcg cccggcccca acattctttt   57660
ttgcttggga taaaccctct tcaggctgtt aatcaatata gataaaagta tactgttcta   57720
ttcttttcttc tcaagtcatt ttcaatgctt tctctgcatg ggcaatgcca aaatcccatt   57780
gagcatgttc tctctgaggt cagggttcc aaatcttttg tttctcagag tgattgctgg     57840
cttgtttggt tgcctcagcc agtaattctt cataccgctt atgacccttta tactcctgta   57900
cccattttc atgaacccac accctctctg gctgtttgct aaaacactgg acatgatatt     57960
ttcgggcacc tcctgtgtta attttggtat gaacctccag ctggggatca cttcaatcca   58020
tacaaggcca gcacggatag gttcccacct tggaccacac aagatcacca acttgaaact   58080
taacaccagt ggacacttct gttgttggaa cagaagatag tattggctga actggggctt   58140
cctcttttag tactggatct tcccttggtt tttctgatat ggtgtgaacc ctctcatttg   58200
gtctattttg ttcctctggt tctaatttgg ggattttgtg tgacttgcgc tcttcagatc    58260
ttgatgagtc atgcttttg ggtttttcc tcttttcttt tctgctttca tgctttgagt     58320
tcgtgtgctc acttgcctgt acttcattta aaggtctcc acaaagggaa gacttgaaca    58380
attccctgcc attctggata gttttggtta tttttagttt aacttcaggt gagccactct   58440
tctttggaat cacagtttgt ggtaccgaag tggtggctgt ggaggggaag ggttttctag    58500
aatttaatgt ggtcttctgt ttagaatttc tgaatggtaa tagtcagtgg ggctaaagtt   58560
tctagctgcg ccaaagtcat tggctgaccc attaggatat tgattatgcg actggtattt    58620
ggtttgaatt tcatacatgc tgattgatgg caggtagcca tttgtgagtg gaggaagatc    58680
tgttgtaggt gagtattgaa agctttgctg caaggtagct tcgtatggtg tctggccacc    58740
atcttcagca atgtcacttt tgttatcaaa ggcatcctcc tgacggatgc tggcggagtc    58800
agtgagttga ggtggttgtt gaactgtgtt tcccgtgatc ccttgcatga aagagaaaga    58860
gaaatccatt gttctgctcc agcattctta actttcccctt tctctcatcg ggccttcagt   58920
ttgtcccgtt ctaaccgccc ggccgtctca atgcgatcac aggagggaca cggagatcga   58980
ggagggccac agccggacca ggccaggcgt gctgcggcag gaggaaggct ccggaggtgg    59040
ggtgggaagg ggaggccgag agacgggtgt cgccgcgccc ccgctgccgc cagagaggag   59100
cctacggctg gcagcctggc ctgggcagca gggtcctcgg cgctcggctg ggaaatcgca   59160
cgtctctccg cggtgacctg tgcacagccc ctgggcctcc gcctccgtgc tggcagcctc    59220
cgcctcagcg cacaaagccc cgtcaccccg actctcggag cgccgccgcc gccaaatcct   59280
```

```
cagcccctcc ctcattggcc gcggcgtctg ccgggaagtg cagtcccggg tttggggcga   59340
tggagcccag gaggaagcgg cgagtcagcg cggcggagag ggcggagggg acggagggg    59400 cggaagggga cgaaccacga acgcccgcgg ccgcgaaggg tctggacgac aaggagaga   59460 ctagcgagag ggcttgttgc tttttttttt tttttttttt tttttttttt tgagacgag   59520 tctcgctctg tcacccaggc tggagtgcaa tggcgcgatc tcggctcgct gcaacctccg   59580
cctcccgggt tcaagcgatt ctcctgcctc agcctccgag gagctgggat tacggggcg    59640 cgcctccacg cccagctaat tctttgtact tttagtagag atgaggtttc accatgttgg   59700
ccaggctggt atcgaactcc tgacctcgcg atccacccgc cttggtgttg cacttttata   59760 actctttta ccttctcacc aaactagcat ttaggaaaaa aaaaaaatc aacaaaaca      59820 aaacaaaaaa accaaaaacc tctatcagtc atttacacgt tagttggaaa taatttagac   59880
cagtgtgtct ctccttcgca gaacacattc agtcctctct gattattaga agcaaggttc   59940 acctttgat cttggttaaa gaatttcag gctaaatttc tggggaggag atgtatttca     60000
ggttccagga tcccagaatt gctctgcaca agtcacagcc atccttgttc cctgaagtct   60060
ctgttggctg caccatgtct gctgctcctt tatgagtggt tttgggagag gccaggctga   60120
gctcttacta gctccttgca acaaaacaag cgaatgtgaa aagtcttaaa cactcagctt   60180
tctggtcaga ggaaatccca aaatcagcat gactcaggat tttaagtgcc ccatagagtg   60240
tccaagagaa gaaacctagg agtctagggt ctttcaaaac cccaaagtta aaaccttta    60300 tcacccttc ctgaccttcc tggcttagga ttttaggcag cctcttggag gcctcccttg    60360
cctggggcac acttggccat aaacccattc attcagccct actgatttag tgcccattat   60420
gtgccaggca gaggaaaagt agaaatggta ggatctatct tcaaggggct caaagtctgc   60480
aggaaacagg atccgctaac aaattagagc acaagggtgt gccgagtgct ataatagcag   60540
tgtgggttgc tgttgagaaa atacagagga gggtaccacc agggagcttc tatgagttga   60600
gctgagcctt gaaggttgaa gaggcatttc tcacatagag aagacgaaat agtaccctga   60660
ttgtatacta ggaatgaaaa caccaagtgc ttaccaagct cagataggta acgtaaatga   60720
atggagtagg tgagtaaagt agcagggatt gtcagcggtg gtggggaagt ggaaggcctg   60780
catcctgcct acagggcttc tgctggaaag acagcctggc ctggattcag cctccatttg   60840
caccttctgc taggtgcttt tgtgcagtgc acaactcaca caacctcaca tggctgccct   60900
gcctgcctaa gctggccatc agctgcttgt tgccatactg aaaaagaggg tttggttttg   60960
cctcgccttg cttttcaat agaagccaga aacttgaatt tttatgtaaa aatttccaat    61020
ttgtcaaatg ccattgtagc caaacaaaaa tctagcctca ggctggatcc accatagagt   61080
ttcagtttga gaccccgatg ggaaccagtc ccctgggcac atgctgctct ctctcctcca   61140
taccatgcaa cacagtcctt tgctgagatt tgacaaggga aacacagtca tagatgaaac   61200
cccctacagc tgctgcaaag ccccttcagaa acatgagatt ggcctctgaa ccagaggaaa   61260
gtaacgtggg gctgtacaac agcagccagc ctgtgagact gatggataaa gctttaattt   61320
atcggtgcac cttgttttgga gaaagcttcc ctgccctctt ggctgccccc acctccaacc   61380
cctcctgttt tgctaatgat aaatgacaag cagtggacat ttattaatta aaccacccgc   61440
tgtagccatt ggtaaaaccc aaggccacat gcagggaag cattcaaagc attcctgctg    61500
cccctgccca gggcacaggc cccagggtta tcctttgctg gagagagcag gccacggcgg   61560
ccacagcctc acatgatggg ccttcctagg atctgtctgg gttctggctg ataaatggaa   61620
atcacctcca tgggccacac agtaattaaa ctcctggcat tcttttgaca aaaaaaagt    61680
```

```
tcctcatggg acattcccac aagctgctga aggtctggga cctgcaagct cccagctgat   61740
taccaaggag ttttcgaagt tggccttgac tgaggatcaa aggaggatgg gagttcaggg   61800
aatgagggtg ggggtgggaa atgccttaga attaagttga tgatggcctg ttgcggtggc   61860
ttatgcctct aatctcagtg ctttgggagg ctgaggcggg aaaatcactt gagcccagga   61920
gtttgagacc agcatggaca acatggtgag acctttctt  aacaaaaaat ttaaaaatta   61980
gcctggtgtg gtggcacatg cctgtggtcc catctacacg aggaggctga ggtgctagga   62040
ttgcttgagt ccaggaggtt gaggatgcag tgagctgtgt ttgcaccact gcacttcagc   62100
ctggtgaagg aggagaccct gagacagaag gagaccctgt ctcaaaaaaa agttgatcat   62160
ttggatgttc ggcctgaaac acccacattt atttccccag gaccgagatg gcagagaga    62220 taaaagcagg ccttcaaggc tcatttattt atatttctac tgtttatttg ttccactgat   62280 gtacccaag  tacctaaaac agagcctggc acatagtagg tgctcaataa atatttgttg   62340
actgattagc tggagatgtg ctcatgtctt tttaacgaaa gcagtaatca ggagaaattc   62400
ctaattaagg tcctagaacc agtggcttct aattgtttgc tgccacagga ttgtaaacat   62460
gttgaagatg aggccagtgt cttattcaat tgactgtccc cagaagcagg cacagtgccc   62520
agcctagggc ctacacaccg tggtttctca acgatatcaa ttgtctgaat gactcagggg   62580
taaaccattt ttcagtgctg ggtcaggcag agccccactg ggacgtgacc tgcacacact   62640
ttggcagtcc cctgggatgc agtggtagca gcagcagagt cataaagcct ggggatcaga   62700
gccacactgg atatcacagc tggaaaggcc tgagatctca gccagtccct tgctaagcag   62760
aaagaagaaa tgaattagct acaaatcttg gggcctctaa aaacacagct tcattttct   62820 gtttctccta tagactcccc attctgtcca actgccaaaa acatttaagt ttatttaata   62880
atcaatgtca gctgaagttg gtcatatcag acttaaattc aatctattcc cagttgcctc   62940
aacttccctt gtcaggtcat ctacttagtt ctagtggctt ctgtgccata ggaggggag    63000 ctggaggagg gggagagccg agccatggtc atcagtatct gtcttcacta acctcttggg   63060
catggtcacc ccattttgtt ggtgtctgct aaatccacat ctttttttc  tgtagtaatt   63120 agcccacaca ctctgtgtcc tcctgactct gcagctgagg ccctcccagc ccaccaggcc   63180
ctgcccagca ccttccatgc cttccttgga agtgttggaa aactagctgg cccctcatac   63240
tatagggacc cagggaagtt ctgattgacc ctgggtgcca tgatagaaca ggactccacc   63300
cactcagcat tccagataaa cagtggacac agtctccttt gcactcctat tttcccaact   63360
ggttgggagg attctgttgg tgcctgctcc ccaccctatt gggatctctg tctccctggt   63420
gagctgtgta tgtgcatgat ggtgagggtc tccagcaaca aggaaaggag ttacatttgt   63480
ccatattcac actgctataa agaaatacct gagactgggt aatttataaa gaaagaggt    63540 tcaattgact catagttcca catggctggg gaagcctcag gaaacttaca atcatggcgg   63600
aagggaaaag gcatgtctta catggtggca ggtgagagag agtgtgtagg aagtgaaggg   63660
ggaagagcat cttataaaac cgtcagatct cctgagaact cactcactat caccagaaca   63720
gcatggggga accaccctca tgatccagtc acctcccagc agctctctcc ctcaacacct   63780
ggaaattaca attcaagatg agacttgggt ggggacacaa agcctgacca tatcagaggt   63840
tgatcttgca gcattttatt ctctgaatgt cacatgggga aacggaggtc aagaaggtgg   63900
aaaagacttg cctaaggcca cacagcatga gtgagtgtgc ctaaggccac acagcattgg   63960
gccaagagcc tgggacttgg taagcccctc ctgagccctc ctcctgagcc aggcctgtc    64020 tcaggttcta gcacatgcaa ctgcaaccag cagggtatgt gtcatagtct taaaatatgg   64080
```

```
ccacaaattc tttgatggtc ttcccattga gctgtggggt ctatttctct cttttctttg   64140
aatattggca gggttatgac tgcttcaatt aattgagtac agagaggtga tgctgtatga   64200
cttccaagcc taagtcatct caggccatca gcttctgcct tgttaatgg aacacttgcc    64260
tttggagtcc tgagcctcca ggtaaaaagt tcaactatcc caaggctacc atgctgtgag   64320
gaagcccaaa ctacacagag gggccatgtg aaggcactct ggttgacagt ccccactgag   64380
atgtctcagt ccaggcacca ggcatgtgag ggaagaagcc cccaggtgat ttcagccctc   64440
agccttttcca gccacctcta gccatttgag tcttcacaac cctggcccta gacattggag   64500
agcagagaca ggccaccctg ttgggccctg gccaaattct taaacctctg aatctgtgag   64560
cctaataaaa tggttgttgt tttatgtcac caactttggg gtggcttgtt acacagccac   64620
agatagctgt gccatcttaa cctgctggat tggtacccct taagtctctg atatccatgc   64680
ttctgcccgg ccactaatga agccacatct gttcccacca aagaccact gagaaggcca    64740
gtgagtgtgt ggtggggacc cttgtttgaa ggaagttggg tgaaggaagt tgctgacatg   64800
catgactgct aacaaaagaa tatacatctg cggaggttgt tctggaagta tcttagggaa   64860
gtaaaggaaa ggaattaaga ctcatcgaca acagactcca ttccttgccc tgcccatcct   64920
tattcattta ttcaacaagg ggtctatgag caactacgag gtgccaggcc ctgtgttaag   64980
attctgggac atggacacag gcctggccct agtggttctc ctagtccagc tagagacaaa   65040
cattaaacga tgattaatat acatactttg aatgaaaaac ttagggtgtt ctgagagtgc   65100
gtggagacct atttaatcct cataatatcc ttctgaggta ggcaccatcc tttctatttt   65160
gcagggggaat actaaggctc agaggggtta agagaccttc ccaaggtcac ccagcagggg   65220
agacaccaga ttgcaaagaa gcagccccca cccacctagt gaggcagga aagcagaggc    65280
ataaatgtcc agctgagcat gagactcctt gggccaacag gagcacggtg gggtcagcac   65340
cctcagacag gcaacctctg agggagcagc attaacccct gggaagccag ggtagcttgt   65400
taatccagca aacctgcact tctcaagaaa aaatggccct ctgttgggaa ggaatgattg   65460
agctctaatc atctagcagt ccctgggcag ccacactcac catctctata atgagggcag   65520
aaatagaggg caagaggtat ggtaaccatc cagaggcagt gactgggact cctaaacccc   65580
tccttgattc tgagtcccca ggggccagtg gagggcatt gggaggtgag acaagacatg    65640
cagacaaccc gcctccaaga gatgtcatag agaagtgggc ttcagacctt ggggtgtgga   65700
agcacctgga gaataggtga aaacgctgat gcttggcccc accctgaggg atttgggttc   65760
atttggtctg gggcgaagcc cgggcatctg tgggtttttt tttttttttt ttttttgagac   65820
agtcttgctt tgttgcccag gctggagtgc attggcatga tctgagctca ctgcaacttc   65880
tgcctcctgg gttcaagcga ttctcctgcc tcagcctcct gagtagctgg gattacaggc   65940
acctgctcac acacctggct aattttttgta ttttgagtag agacggggtt tcaccatgtt   66000
ggccaggctg gtctgaaact ccagcactca agcgatccgc ctgcctcggc ctcccaaagt   66060
gctaggatta caggcatgag ccaccgtact ctgccaaaaa tatatatctt tagattagct   66120
tttaatagag ttcttcaaat acccaaaaga ttagggaaaa ctaggatgct aaaagatgaa   66180
ataggtgact aggcaaataa atcattaggg aaattggttt caggctcatg gtattgttcc   66240
ccacaatgct gggcaagtta cttgtccatt ccaagtttca ttttccccta cctgaacaat   66300
ggagctaata aaattgattt caccgggcgt ggtgggtcat gcctgtaatc ctagcatttg   66360
ggaggccaaa gtggggatgg atcacctgag gtcaggagtt cgagaccagc ctggcccatg   66420
tggtgaaacc tcatttctac taaaaaaaat acaaaaaatt agccgggcat ggtgtggcat   66480
```

```
gtctgtagtc ccagttactc gggaggctga ggcagagaat tgcttgaact tgggaggcgg   66540
aggttgcagt gagccgagat cgcatcactg cactcagcct gggtgagtgc agagtgagtg   66600
agactctgcc taaaaaaaaa aaaaaaaaaa tttcacagtg tagttttgag gacgttgtaa   66660
gagggcgtga gttatgtgcc aagtgggtgg taaacgttca atagatgcta ctttccttcc   66720
ttcctgagca tttggaccac acagagacct ccctgctctt ggctttggct ttaaggagct   66780
tgtggtcact gagaggattt tgcactggaa gtacatgcat tcaaaatgga tacctaagtg   66840
tatattttct ggtgtaaact atatgtcgac tctaacttta gcccggggga gctttattat   66900
ttgtctccct ttcatgaaag ctataataga ggaagagaaa accctgcctc gcacattccg   66960
attcctaaat acataattta taattttctg ggatattatt taagtttatt ttagttctgg   67020
atacacacca tccccgtggg gtgcttattt aagtatcggg tgggctctgg aaaggcctgg   67080
aatgcctcaa aaggagggaa gaagattctt tccattcatt aaacagcagg gcctggggtc   67140
tttgcaggtt ctagggctta gaagtttcct taacaccaac tgaggagtcc cagggtggga   67200
gctgagctca cacgaagctc tacttcgcgt gtcctgaagc tttgacagtt gggcctcttt   67260
ctggcttttg catcctctgc tcatactaag gccagcagag ctacaggttg gaccatggtc   67320
tggccgggag ctccagcttc ctcttttcct ctcagtagtc atcgggccag ctgcccatac   67380
ctggtgccca ggtatgagaa gagacctttg gctttcacca ggttcttgag agggtcaggg   67440
acctccaaaa ggataaatgc cattggtcag atagtcactg tctacctccc tcccatccat   67500
ttcctgcctt caacccctgt tcttgggaca aggccttcgc tggcattcaa tggcgggtcc   67560
ctgaggaagg ccccagcctt gccgaacatc cttcaaggga gacttcagcc cctggccctg   67620
cagtgagtgt gttgttagca gcagagggc tgagtgaggc agtgggatgg ggcttttctt   67680
ttttgttctg gttgcaaatt ataaaccccc aaatgctgga gttccagact gaggttcaca   67740
aactttagag ggcagaacta aagtcaaatg tgcttttaaa agcacccag gagatgctga   67800 tgtgggtgga cacttgaaga aacactggtt gataaagttt ctctctttct ttttttttg    67860 agatggagtc tcgctctgcg gcccaggctg gagtacagtg gggccatctc acctcaccac   67920
aacctccacc tcccgggttc aagcaattct cctgcctcag cctcctgagt agctgggatt   67980
acaggcgtgc gccaccatga ccagctaatt tttgtatttt tagtagagat ggggtttcgc   68040
catggtggcc aggctggtct cgaactcctg acctcaggtg atccgcctgt ctcggcctcc   68100
caaagtgctg ggattacagg tgtgagccac cacgcccagc catggttgat agtttctaga   68160
aagctgttcc aagttactgg ctgtttttga attgttcaag cttaaaaaaa agtaggcacc   68220
ctttaggaag gccagtagaa gtcccattcc caaggagggc aggcctgtga gcacgttaat   68280
ggcaacagtg gcagctaaca accacttttg tagccctact gtgccccaga cactgttcta   68340
agcactcata acattaatc taaacctccc aacagcccca catgccagga cacccgtgcc    68400
tctatttcag gaaaggccat ctggatcttg caggacggca aatgggagag gacaaacaga   68460
gccccatagg tgaaaaggag gaacgagagg ctggagagga atggggagca ttagagatca   68520
caaaatgtgg tagacagaat aatggtcccc agatgttcgc atccacatcc ctggaacttt   68580
tgaacgttac cttatcttac cttatgtggc aaaagggact ttgcaggtat gattacgtta   68640
agaatcctga catgtgaaga tcattctgga ttatccagat taatccaggt ggattggggg   68700
aacccagtgt catcacattt aagggtcctt agatgtggaa gatagggta gaagggtgag    68760 tcaagggagt gccatgagag aaggtggaag gggtcacaag ccgaggaatg caggccactt   68820
ctcggatccg caaaaggcga ggatatgtgg tctctccaga taggagcaca gccctgctgg   68880
```

```
aacctggatt ttagccccat gagacccatc ttacacttgt gacctttaga gctgtaaggt  68940
cataaatttg tgttgcttta aggctctaag tttgtggtaa tttgttgcag cagccataga  69000
aaactagtag aaggaagaaa aggagcatta agagagattt cccactttgc tttgaaaagt  69060
ggctagaaat agatggggaa acggggagaa gatggcccag agcggaacgg gggagaaagt  69120
cttcttctat gactaaggaa gagtgaggct tctaaacggc cctcaggaaa gtgtttgtgc  69180
catgatgctt ttcaggagag agtagagatc aattgatctc tgtgctgtgt tcttacatga  69240
aatatttggg agggaagtgt tgtggtgagt cacttgtatt ttttttttaaa tacctgccac  69300 tcccagtttt ccagatagct gaggaaaggc tggggttcaa atcccataaa aaaccaacat  69360
cattcaattg gtacattctc taaaatgtac ataagacatc taggaggact tcataatgat  69420
taagagcaat caactgttaa tgcagtgagt gcttatttttt tccaggcact gtaccaggca  69480
tgctgcttca tttaaatttt gcagggactt ttgaagtagg tcctaccttg atttccattt  69540
tgcaagtgaa aagcatcaca ttgagatgtg gcccttcagc cttagccctt tgatatggtt  69600
tggctctgtg tctgcaccca atctcatttt tgaattgtgc tgccataatt cccatgtgtt  69660
gtgggaggac ctggtgggag ataattgaat cgtgggggca gtttcccca tactgttctc  69720 gtgatagtga ataagtctca cgagatctta tggttttatc aggggtttcc actttagcgt  69780
cttcctcatt ctcactttgc ctgctgccat ccatgtaaga cgggacttgc tcctccttgc  69840
tttctgccat gattatgagg cttccctaat cacatggaac tgtaagtcca attaaacctc  69900
tttcttttgt aaattgccca atgtcaggta tgtctttatt agcagtgtga aaatggacta  69960 atagacccctt cttcctcctt gctaaaatac ttttttgatg gtgatcatga attggccttt  70020
gcgtgcagtg agttttgact ggtctgccaa tgccttttcct ttccagctat gaatggtttt  70080
aaaaaatatc aatgacaagg ccccacctca taaccattaa atgcaaaact ctggtagggg  70140
cccaggtgtt tcttttcttt tcttttcttt tcttttttttt ttttttttgag acggagtctc  70200 tctctgtcgc cagggtggag tgcagtggca caatctcagc tcactgcaac ctccacctcc  70260
caggttcaag agattctcct gcttcagcct cccaagtagc tgggactaca ggtgcgtacc  70320
accacgcccg gctaatttttc tgtatttttta gtagagatgg agtttcacct tgttagccag  70380
gatggtctca atctcctgac ctcattatcc tcccacctcc gcctcccaaa gtgctgggat  70440
tacaggtgtg agccactgtg cccagctggg cccaggtgtt tcttaaaagc tctcaggtga  70500
ttctaatgtt gcagccaggg atgagaccat ttgtctaagg caatctggat aactcctttc  70560
ccattagcca gggattagcc tgtgaactat tctgaccaag gaggcatgaa cttttctgtt  70620
tctggatgtt gtcatctgca aataacagga aggaacctag gatctgaaga tgctgctgag  70680
ctgcctgagt agctcacctg gatccaccct atttctagac ttcttgttat atggtgaata  70740
aatgtcctcc tggtttaaga caagggttgg caaactatga cccaggagcc aagtctggcc  70800
cactgcttga ttttgtaaat aaagttttat tggaatacag ccatgcccat ttgtttatgt  70860
attgtctaca tattgtttag tgctacaatg gcagggatgc atagtcatga cagagacctt  70920
atggcctgca aagcctcaaa tatttactct ctggcccttg gccctttgca gaaaaagttt  70980
gccagctcct ggtctaaggg tcttttttgtg ggcctttcta ttacttgcag ttgagggtat  71040
ctgttaattt gggagtttag cttccccaag gtggcattgt tagtgatggc aagttttgcc  71100
ccctttaagc cattttttca tgggagaata attacagaat gatctttaag ggatttcaat  71160
aatatcagcc aatcctactg cccatgggga agtgggatca cacaggttgg ggcttcagat  71220
aggcctggat ttatggcctg gttttatcat atagatccaa ttgtctttga aaagtgactt  71280
```

```
catcttctag tcctcaactt tctcatctaa aatgaggaca gttatatcta cacgaaggat    71340
gggtaccctc atggaggcaa ttccagacaa aggaatcagt gcaagcaaag gaagcgaggt    71400
gaaaaatctc caggtccaca tggagagccg caagctgctc tgcctgacct aagccaagag    71460
catagaaaag gggtcatggg gcacactgtg gtgaagatag gctggcattt gttgcataat    71520
aatttctcca gttgtcttgg gtttctgaga ggtagcttct aaaccttgg aatttcccaa     71580 gtgataggaa tgtctttgtt attcatagtg agccactggg accatgcctg agttcatact    71640
aacaaggtga ctcatggtgg gcccctagat agtttcaaga tggggactag ccattaggaa    71700
ccaaccaaat gattagaggg ttggggtttt gagccagatt atatcagcct gacttccagg    71760
gaggttagag attgagttca atcacatggc caattatttg atcaatcatg cctcgtgatg    71820
aaacaccaat aaaaactctg gacctcaagg ctcaattgag cctcctggtg ggtgaacacc    71880
agtgtgctag gagggtgata catcctgact ccatggggag aagatatgga agctctgtgt    71940
ttgggatcct cccagacctc acctatgga tctcttcatt tggctggtcc tgatttgtac      72000
cctttataat aaaagtgtaa tggtaagtat agcactttgc tgagttatgt gagtcattgt    72060
agcaaattat caaatatgag gggttgtggg aaccccaaa tttgtagcca gttgatcaga     72120
aatgcaggta gcctggggac cccatattat gtggggtctc tgaagtgagg gcagtcttgt    72180
tgaagactat gtccttaacc tgtggagtct gtactaactc caggtagttg acactgcaaa    72240
agtatatact gctgtattgc agagctggat tcatgaatgc ctgtttccag acttggattt    72300
aatttggttg gtggtgggga gccatagaag gtttatgaga agatgaatga caggatcact    72360
aactgagatt ctggaagaat aattgggcag agataaaggc tatctagagc tctccctgag    72420
tcacaggatc ttttggtcat gcactctcaa cttgacatg tgatgctggt caccaaagat      72480
gcttcctttc aaaaataaac agcagctata aaggaactca catatattgg tagggttgga    72540
gccatcccag ggcaggccag gcctaggagc tacaggaaat cctcacttct ggaagcagaa    72600
ggtcagttgc ttcttcctgg accacaccct ctgcagacac tagggctcat ggaggagtcc    72660
tggagggata cacagcccaa gccttttgctt tccaccgtaa gaggatggca gtagaatctg    72720
ggtacagctt cctcttggag gtttggggaa cccagtgaca ttcaggagcc cccttttta      72780 aaccttctgt gccctccagc ttgcttcttt ccagcaacag ctagccactg gggcattgta    72840
tttcagcctt tctggggcat ccctgcaag ataggcaccg gcactgcctg ctctctctct       72900
ccctggatct gatttagcct tcactgaaac cctgcccaag atgatgactt aatctctggg    72960
ctgagcgaat gcagccaata tgttcagatg gattttgcaa gacaaaagct caaatctgtt    73020
ttgtggctgc agatacacat tcagactgaa ccacatccgt ggtcattcca gtcacaaaca    73080
caaagggtgc catgaattct ttccatgaaa ataatttcc attgtattgt ttctgtcatc      73140
attcatttca tgataagtca gttaaaacag ccggtccgag tctgtcattg attccaagag    73200
ccccattgtc gtgtccttaa cttactgata gttttaggtc ttaattgtta gtagcaaagt    73260
ttcttttcag gaattctgtt ttctcattga ctttgatgag aaagaaaatg tagagagatg    73320
ctagcgaaaa aatttaattg ccctcaaaga agtagcaatc ttttttcttt aatatatatt    73380
atgcatcaag caaaatcatt ttctgagaac tagttccaga ttgcgtccaa tgtcatgggt    73440
tgtgtgtctt atttatttat tttctcattg agatataatt cacataccgt aaaatttacc    73500 atttttaaagt gtacaattca gtggttttag tatattcaaa agactgtaca accatcacca   73560
ctacttccag aacattttca tgacagaaaa aagaaacttc gtcctcatta gcagtcactc    73620
tccacttcca ctgtcttaca ttccctgaca acaactaatc tctcttccat ctctatgtac    73680
```

```
ttgcctattc tggacatttc atataagtgg agtcatataa tatgtggcct tttggtctgg    73740
cttctttcac ttagcatgtt ttcaaggttc atccatgtcg tgcgatatat cagtacttca    73800
tttcacttca gaattgcata atactctatt gtatgtgatg cagggcagat gaaccccaaa    73860
ttgggactta gtccatgagg attttttggct ttgcccagga aggaattcaa gggcaagcca    73920
gaggtagaag acagctttat tgaagcagca gtggttacag ctctgtgact gctcctgcag    73980
aacagggcta ccccataggc aaagagtagc agctcagggt attttgcagt catatttata    74040 ccactttttaa ttacatatgg attaagggggt ggtttatgca gaaatttcta gggaaggggt    74100
agtcactttt gggtcagcgg gtcattgcca tggaaaggag tggtaactcc caggtgttgt    74160
catggcaatg gtaaactgac atggctcact ggtgggcata tcttatggaa agctggttct    74220 gcccttcct tgttttagct agtccgcagt ttggtgtctg acttcatctc tggagtcgag    74280
tctcacttcc tacctcatat ggatatacaa taatgtgtat atccattcat caattgatgg    74340
atattggatt gtttccaatt tttggctatt atgaataatg ctgctatgaa cattcatgtg    74400 caagttttttg tactgacata ttttcaaatc tcttgggtat atacctagga gtggaattga    74460
cgtgtcatat agtaaactct atgtttaacc tactgaatta gagtatctgg gactacggcc    74520
cagcaatctg ttttaacagc tctccaggtg attctatgat caccacaatt tgagaggcac    74580
tgccctagag taaggggcag taaacagcta gatagtaaat attggggttt gcaggccaag    74640
agtcaaaact gaggatgtta ggtaagcact tacttgataa gacggtaaac aaatttccaa    74700 acattttat tgacaaattg aaaaatataa taataataat tggtaacagg ttgtttctg     74760 tttgttggtt tttggttttt tgagacatgg tctcactctg tctcccaggc ttgaatgcat    74820
agctcactgc agccttgacc tcctgggctc aagtgatcct cccaagtaac ttggagctac    74880
aggcatgcac cagcacactg gctacttttt acattttttg taaagatgag gtctccctgt    74940
gtcgcccagg ctggtctcaa acttctgggc tcatgcgatc ctcccacttc agcttcccaa    75000
agtgctggga ttataggcat gagtcactga gtcctgccag gaacagtttt ttgtaatgca    75060
ggtttactaa tgagaagaat gtgtttggtt ttttttgtttt tttgtttgtt tgttttttgc    75120
tttgttttgt tttttgcagg attgggaggg caacattttta cttaattggg attcaaagtt    75180
ggtgttccct gtcatcaaat caattgcaga tattcatctg taaaaaccat tcttccggcc    75240
agcgcagtgg ctcatgcctg taatcccagc actttgggag gccgaggcgg gcggatcacc    75300
tgatgcaggg agtctgagac cagcctgacc aacatggaga acccccgttt ctactaaaaa    75360
tacaaaatta gctgggcgtg gtggtgcatg cctgtaatcc cagctacttg ggagctgagg    75420
caggagaatc atttgaacgc gggaggtgga ggttgcagtg agctgagatt gcgccattgc    75480
actccagcct gggcaacaag agcaaaactc tgtctcaaaa ctacaacacc aacaaaaacc    75540
attcttcctt catgggctgt aaagtaataa gccgtgggcc agatttggcc tgtggctcta    75600
tggtttcaac tagttctggt gcatagcagc ccccaaagtt ttagcagcgt ggttagtgga    75660
gagctgtggc ttttgcctcc atctaaattt ttctttgagc aaattacctc tctcctgaca    75720
gccctgttgg gggtgtcagt tgtgggggttc tggtacctcc catcccggcc ccagctagag    75780
caggcaggcc cacaggaatt tgaatctgga gggagttatc agtggtggag cgtagaggct    75840
gcaggaatct tcatataagt ggagtcatat aatatgtggt cttttggtct ggcttcttta    75900
cttagcatgc tttcaaggtt catccatgtc gtgggatata ttagtgcttc atttcacttc    75960
tgatggcagg gtcctgaatt aagtcctgcc ctgaggatca cactgttaca tctaggcctt    76020
gtaggattcc tgaaaattgc atcccatctg ccctgctcta aaatctacac agcctttgcc    76080
```

| | |
|---|---|
| atatccattt atcgatttgg ctcagcaaca tctactaatg atgcttaaat cctgggcaag | 76140 |
| tgtatttgaa gtggcccag aggttaaaga tctggatgtt ctccctccag caacagcacc | 76200 |
| actgccccac agcctggga ttttctgttc tgcttgctat taatcactta cttattgcat | 76260 |
| acttatatgt gccaaaaatg ggatcctctc ttgccctatt gtaaagtgat acccatcttc | 76320 |
| tagaaaccaa tccagcaata tatgagaaga gccatagaaa tgtgcccct tggggaaaag | 76380 |
| aaataatcct aagtagagaa aaatgtattt gagcaaagtc attcatggcc acattctgcc | 76440 |
| cttccgtggc cagaaatgga taaaagctga atctactgcc agcaagtatc acctccactc | 76500 |
| attcatgatg cagagcgtcc ccacccttcc cactgggttg ccttccagaa aacagcttcc | 76560 |
| atgatgccca gtaatctctg tttcccttga tctctctcat ctccttcctt gtctaacctt | 76620 |
| cttctcttag aaaaggagct tcatcccctt tggtcagtag ccagcaaatc tggattgctc | 76680 |
| cctgtggccc ttgtgctcaa ggcaaataga accacctgct ccacatcctc ccatcttctg | 76740 |
| agtggagggg ccttgagata atccacttct ctgcttagag tggattcttg atgtatcact | 76800 |
| ctaatgattt atgaggttaa aagactccct cctcagtagg ggtgagctta aatgttccc | 76860 |
| tcctcagtaa ggatgagcat agagagggaa aaggagctga cagaaccaga gaatcccatc | 76920 |
| caccacattt acgatagtga aaacattaga agccatccaa tgttccaaac acctctggta | 76980 |
| ccagccaagg gggctgaccc aaggcaggat cccaggagct agggttgagt gggtggggga | 77040 |
| ggcactccag gcaacaaggc atcagatctg aggacaggtg ccaggctcag cctgacaagg | 77100 |
| taggccaagg gacagttcta gagaagcagc caggataacc tgttttattt tgttttaat | 77160 |
| tgggtgcaga cacaagggga gtatggaaag ccattggctc aggtctcaat gggtctcaaa | 77220 |
| tttagacttc tgctatttt ttcttcaagt gcaattgcat atttagtctc agagagtgac | 77280 |
| tctgacaaga cccaaagaga acatttgtca tttggccttg accttgtctc cacatctgga | 77340 |
| gagttggtat cacgtgtggt accttatttg tacatttctt gggggttcat aacaatgtta | 77400 |
| taccacatta ctggtgaaag gaatattaat ttgttcagtg taaacactga aatagctgac | 77460 |
| aatcttttat ttttaatttt aatctatta tttgtttga gactgggtta agagattggc | 77520 |
| taatatttgt attttgggta gaggtgggat tttaccatgt tgccaaggtt ggtcctgaac | 77580 |
| tcttgggctc aagaaatcca ccccccttgg cctcccaaag tgctgggatt acaggtgtga | 77640 |
| gccaccacac ccagcctaaa atagctgaca atctttataa ccctctttag gcatatttac | 77700 |
| attttatagt atattaggaa cctcaaaaac tgatggcaat tcaggttttt ccagtattca | 77760 |
| agaaggcatt atctaagctg tcagatctag ggggtggtg agtgtgatac ataaattggg | 77820 |
| aggtaaatca aaaagtctgg agcaggcaga agaatgcagg aagaggtcag ggagtgaagg | 77880 |
| actgattga gagggccaag atttgggtt tgaacagggc tgacttcagg gagcgggagt | 77940 |
| ctggccccag gtaaaactta gtgtcattgt gtgggtcaga agacaacaaa ggatccttaa | 78000 |
| ggaaactatg gccatcatc tcagtagacc aggcagcctt tgggaatgat ggtcacaaag | 78060 |
| actctgtggc aacatagaaa atgctaatgg tgtcatacag aatacagaac tttatggacc | 78120 |
| tatggtacaa acaaacacat gcatgtgcct gcacacacac acacacacac acacacacac | 78180 |
| atacacagag gaaacaagac tggaagggt tacacctaaa tataagtagt gcttgtgtcc | 78240 |
| atggggtgga gtgatattgt gggtttattt gctctgtatt tttaaataaa acaatggctc | 78300 |
| aactcagaag ataactgagt cagcgtctca tccagcagcc cccggggccc ctgggagaag | 78360 |
| ccacctccca ccacctggcc aagaagatct agacaggctg agaggctccc tctccctctc | 78420 |
| ctggggtccc gagccacaaa tctaaagcca cattccttgg gtgaccaggc agggactggg | 78480 |

```
gacagatgtc gaaactggca aggccccact ctgtggtacc cagcctgctg tggctcctgt   78540
cctagtgcca gctcctctgc tgtcatcccg tccccacccc acacatcccc acctcccag    78600 ccagttgggc ccaaggtgcc ctcactgata tgttggagga ataatctgct tctctccagc   78660
tcctcaggag acccgcgtgg gaggtcccgc gtcacgggct actgaggcac atgctgagtc   78720
ccctcccatg ggcctcagca cacctactat ggcttagctc ttcccaccca ggacctcctc   78780
agggcttctc ggcattccag aaagacaaga agattttctt ggggccaagg cgttgctggg   78840
cctctctgtc ccggccaggc cctcggcaag ctccatgcct cgactctact gccttctctc   78900
tggtcctctc tgtcacccctt cagagacttt taaatcccat agtctgggct tcagggcctc   78960
caataaaagc agaataagac ctataaggac ttaatagagc ttttatctat aaaagagaca   79020
gaccttctaa tctaactaga aactaaggtt aaaaaaaatg aaaagagtta gacttaaact   79080
cttaaaaaaa taaaaaaga ttcagctctg tcagagtcag cctgatgtgg tagacaaatt    79140
gctcatgaat tactcacagt gtttgctaaa aaatgctggt tcctgggagt ctctgagcct   79200
actctggctc tagaggctgc ccaatttaaa aaaagaaaa atgcaggttc ctgagtctag    79260
ctccagaact accaaatcaa aatctcgggg aggtgaggac tgggaatctg aatgtgtaac   79320
acgttcccta cgtgattctg aagcacactg caccggtggt ttagtggttt ccatgccagg   79380
agggcattgc gccctccttg agaaccctgc cttcccagca ctagctgctg ggaggctggc   79440
cagcacagac acagtcctcc ttcccaagag attcctagcc ctggcgagga ggaagactcg   79500
gtgggtaaca ggagttgcaa tgtgggtttg tacccagttc ttggggagca cagaggagag   79560
gggagttctc agagagggaa gatgtctcag ggaatgagtc tctggggcca gatcctgagg   79620
gctcagtagc attgactagc taagaagag agcagaggta tcccaaattg aggacatagc    79680
atgggcagag gcacaatggg gagctgtaaa cagtttaggg cctgggcaca ggtagggagt   79740 agagggagg aggccagaga gatgagtggg gctggtcttc ctgctggttt gtgttttgtc    79800
catttggcta atctgggaat aatacttccc agaaacccct tctccagagg ggtctagggt   79860
agagttggtc aaaagaggag cttgcatgag atttggaaaa taaaagtgaa gcagcatcct   79920
gactctcagg gggttgtcac ggtcatgtgc cgtgatgaca ctgaggcaga gatatgcctg   79980
gccaatccac ctctcgggct gctggctccc ggtctggccc gtgttctggc cagctgggct   80040
tgctgagcta cagctgcccg cagacctgtc caccggctcc cttcacggcc tcactcaggc   80100
agctgatgtg cttgcttctt gggcttccct gcaaactctg acttgtcacc cgtattaggc   80160
cattcttgca ttgctataaa gaaatatctg agaccagatg cggtggctca tgcctctgat   80220
cccagcagtt tgggagccca aggcaggagg atcacttaag cctaggaaga ggaagttgca   80280
gtgagccaag attgcaccac tacactccag cctgggcaac agaggaaaac tctgtctcaa   80340
aattaaaaaa tttaaagaa ggaaggaagg aaggctgact gacctgagtc tgggtaattt     80400
ataaagaaaa gaggtttaat tggcttgtgg tcctgcaggc ggtacaggaa gcatggtgct   80460
gggcatctgc tgggtttctg gggaggcctc aggaagcttc caatcatgtc aaaaggtgaa   80520
gggggaagcc agcacctcac atggagaggg ggagcaaggg agataatggg ggagaggagg   80580
gaagtgctac acgccttttt ttttcttaga cagggtcttg ctctgtcacc caggctgggg   80640
tgcggtggtg caaccacagc tcactgcagc ctcaaactcc caggctcagg tgatcctccc   80700
acctcagtct gcctagtagc tgggactaca ggtgcacacc accattcctg ctaattttt    80760 ttttttttgt attttttgcc atgttgacca ggctggtctt gaactcctgg gctaaagtga   80820
tccacctgac tcagcctcct aaagtattgg aattacaagc atgagccacc atgcccagcc   80880
```

```
aggagtccct ttttgttctt tttttaaatt ttattttaga cagagtttca ctcttgttgc    80940
cccggctgga gggtagtgga gcgatctcgg ctcaccgcaa cctctgcctc ctgggttcaa    81000
gcaattctcc tgcctcagcc tcccgagtag ctgggattac aggcatgtgc caccatgccc    81060
ggctaatttt gtattttat  tagagacagg gtttctccat gttggtcagg ctggtctcga    81120
attcctgacc tcaggtgatc cacctgcctc ggcctcccaa actgcttgga ttacaggcat    81180
gagccaccat gcctggcagg agtccctttt taagagcagg aaaatatttt tccataagca    81240
actcctccaa cacacacaca cacacacaca cacacacaca cacacacact cagagtccct    81300
ccatggctca tcggggtaga cctttaata  tccagggctg gagaaggaca atcccttcac    81360
acttgaacgc tgtgaagtct gtgcccttgt ccagggcacc tgccaggagg agtaggcagt    81420
gggtccggtc tttcagtgga gggcttctgc agcttcagat cgtctctagg agtctggagg    81480
tctatcttat ggcttgtatt tctggaaccg agtcatgcct gcttgaagat aagaagatca    81540
aacaacagga tgctgtggct tctcctatcc caggggcctc gaggacaaat cagttccctt    81600
cctgggggag cagatcctcc tggctgggat cttcagtcca agttggttca atttatatcc    81660
ttcacgtctg gcttctcctg catgtccaag tcacaggaat tttaagtcag gatcttctct    81720
gcacccctga gcatgacagc cagcctctgc cctcatgaag ctcccagtct aagggaagaa    81780
ataataaatt ggtggccggg catagtggct catgcctata atcccagcac tttgggaggc    81840
caaggtgggc agatcacttg aggtcgggag ttcgagacca gcctggacaa catggtgaaa    81900
ccccatctct actaacaata caaaaattag ccaggcgtgg tggcatgtgc ctgtagtccc    81960
agctactcag gaggctgagg caggagaatc gctggaacct gggaggcaga ggttgcagtg    82020
agccaagatc atgccactgc cctccagcct gggtgacaga gcaagactct gagattatta    82080
tctcaaaata ataataataa taaaataata ataaataatt ggcagttaga gggcacttca    82140
ccaaggcaat atgagggaaa ctacaatctg tcaggaaaac acaggggaag gccctaactg    82200
gcccaggagg ttcagcgggg catccaggag gatgtatgag agccgaggag ggagtagaag    82260
gtgatgtagg aaaaccactt agctgaaaga ctcgctgccc aaaggccgga ggtgggagag    82320
agtgcgggac ttgcaggaac taagaggagc ccagagaggc atctgagaag agaagggctt    82380
ggagagctgg gagcatcaga tcgggtttag cctgggggcc tggctgaggt gagtgctctc    82440
catcctaagg ccacaggaag cagaggaggg acaggatcag attctgcgcc cagaggaaga    82500
ctggcttaga ggaggtgagt ccagaggcca ggagaatatc agaggccagg acaagggaga    82560
cggcggccaa accagggaag tggcactgga gagaaatgga tggattcaag agacgttagg    82620
caaatggaca gaaaacagaa accgcgcacg tggtggttgg tgagttgaat gcatgcagga    82680 gatagggggcc caagggagaa ccataggggg ttgattccaa gggtctggtg gagccctga  82740 ggggttggag acacccagct ggtcagccac acagtctggt attaaatgac acacggctgg    82800
tcagccacac agaagctggg cagtgtgaat gggtccagta ccgacttcag agtgtgcacc    82860
tctgtctccc cagacagcaa cagaaggacc agggaaattt aaaagggagt ctatgaatga    82920
tattgtaata taaaatctct aatgaagatg tgactactag aaaaaaggga aataaagcga    82980
ttgaggaaag gaaaacaact tgtgcataaa gaagcaaaga ataagcaact gaaagctcaa    83040
aacatttttc caggcctggg ggatgaggtg gagagagtct cttgctccca ctccaggagg    83100
agggctgcct ggaactaaag ttggtgctta tgatctggta tttaaatgac attcttagtg    83160
gtggtgttag cggtagcaga gcaattgtgc cagggcccac cgaccccttg ctggttcact    83220
cagttgccaa catatactga tatactgagc acctgctgca ggccaggctc tgtggtctca    83280
```

```
gatctcaaga acaagccagc tcagtccctg tctaatagag cttacaactg ggcagcggag   83340
gcagacctgc catgagacaa atataaaatg acaacttgtg acaagggtta ggaaaaagaa   83400
tagtggaatc ctgttttaga tgggatggtc agggaaggcc tctgaggagg tgatatttga   83460
gccgacatca gatggatggc agagaatgca agaagagtgt ccctggcaga gggaacagca   83520
tcgtcataat tgggagctgg tgctttcgag gaactaacag acaggcaggg tgggtggagg   83580
gtgggagcca gggctgggct gggggttgtg aggacactga caagagacca gttggagagg   83640 gggcggggc tgaccatgca ggaattggaa tctttcagta aagtccagac caaatgattc   83700
ttcagggtcc ttgttccccc aggtttcaat gacactttaa aggtgttgtc gtaaaaggct   83760
ggggagtctg tttctatgcc cccaatctca tttaagaagg ggggcatcca ggccatcatg   83820
gaacaggtga cctggaagat gttccttggt ccagtttctg caaactgccc cgcagcattt   83880
ttagaaaatg ttccctttta gattcgattt atcttagcca aattgaccag ggaaaatagg   83940
tgcctacaaa tagcgatcac tggcaaacaa ggagagttat tatcttaaat taaggctggt   84000
ttctaacaac aaaaaaaaac ccaccaaatg ccactggcca ccccccacca accccgatcc   84060
ccagcgcata cgtgaggacg atggctccac caccctccct gtaagtacca ggctcaatgc   84120
cgggctctgt gcaagggaa ggaaacagac agaggaagga aggcaagaga ttagagaagc   84180
tgacagatgt aaatagcctc agaggagcca cactgtcccg gcatttctcc ccagggagcc   84240
ttttgtacca aggaatctgg ttgcctgaaa gaaaaatggt atcatttatt tctttagtca   84300
gagctgagct gttttcttca gacatagaaa taacctaaca tcacacacca aattgttggc   84360
caaatgacag agatacctgt aatgtgggtg tttaataatg tccagggtaa acaatcatgg   84420
acttggtttc ttgggaaggg ccccgttccc cgccatggtt gcaaagctac agagggtctt   84480
gaatgaaata agtgctttgg aaaagttgtc ccaaagttct tgcctgctgc tgagctggga   84540
ggaagctggg cttttcattt ctgctgctca aatcatgccc cagcagccaa acatccatta   84600
attcaacaaa tatttatgga gcccggattc tggccaagcc ctgtgcaaaa gcactgaggc   84660
tacaaatgtg cagaggctgg ggtcctgtcc tcaatagcct catagtccag aggggagacg   84720
gccacgttca gcctgtgtgt caatcttgta acacagcctg gatgtggcgt ggtggtcagc   84780
tctgtggagg aggcagtctc ctcaaaagga gacttgaagg ggaatttcca ggccagagga   84840
gttggaggag gggatcctag acagactaag gagaatgtgc aaaagcagag gcttgaaacc   84900
ccctgggcga tttagaaatt aagagaaata cgatattgca gagaacaaag tgctaaggaa   84960
gtcagcggtc aaatgcgtgg ctggacaggt agatggatac cagatcatgt acttgtaagc   85020
taaggagttt agagttgacc ttttaggtaa taaattccat ggaggaattt gagcggggaa   85080
atagcatgat tagattttg tattagaaca ctcactcctc tctgtcctga agaaactcta   85140
gcatatgtcg cgtcaggaga caaattcggg catcttcctt agtgcattgg gtttgatggt   85200
gaaaacactg gaaacaaact aaatcagtag aaaaatagat aagcaggcca ggcgcagtgg   85260
ctcacgcctg taatctcagc actttgggag gccgaggcag gtggatcacc tgaggccagg   85320
agttcgagac cagcctggcc aacatggtga aacctcgtct ctactacaaa tacaaaaaat   85380
tagctgggtg tggtggcaca tacctgtagt tccagctact caggaagctg aggcaggaga   85440
attgcttgaa ctcaggaggc agaagttgca gtgagccaac attgcgccat tgcactccag   85500
cctgggtgac agagcgagac tctgtctcaa aaaaaaaaa aaagaaaaa tagataagca   85560 aatagtggta tagtcataaa atataatacc attcaagatt ttaaataat ccaacatggc   85620 tagatcttaa aagcataatt ttgagtaaaa aaaaaaggtg agtttcagca tatgtatggt   85680
```

```
atgataaaat gcatgtgaaa tttaaaaacg cacgtttgta tattgattat aaataatata   85740
tgtaggatgg tatgaaaaca tggattgttg cctttggaaa caatccatgg agggaaaggc   85800
atggaaagag aaatacatag aatttttcta ttggttttat atctaaaaga aatatgggcg   85860
gggcatggtg gcttacacct ataatcccag cactttggga ggccaaggca ggaggatcac   85920
ttgagctcag gagtttaaga ccagcctggg aaacatagtg agaccttgtc tctaataaaa   85980
ataaaaaaca ttagctaggt gtagtggtgc acacctgtag tctcagcttc ttgggaggct   86040
gaggtaggaa gaccacttga gcccaggaga tagaggctgc agtgagctat gattgtgcca   86100
ctgtactgca gtctgggcaa cagagtgaaa ccctgtgtaa aaataaaga aatactgtag    86160 atggagctaa aatgctaacg tattaaattt cctgtgttta aaatatttt tgaactttgc    86220 ttttaaaaa aacagagaaa gtaaaatcca tctggcagcg gcatagcaga tggaagggag    86280
gggattgggg aatgggaccc cgagccagtc tctgtctcca cacagcagct cctgggtgga   86340
ggagagctgg aggccgatct tgggggaccc agggagtaat gcatgcagag aacacttcac   86400
cttgttgggc tgcttttggc ctctgggcag agcggaggcg tggtcctggc atcttgtcta   86460
gtgtccctgg aagatacggg gctctgtctt gatcggaact ggcgaccatt ctgacctggg   86520
atgtcagtat catttttgga catctgccaa ccaagggtca gaaacaggag gattttagaa   86580
tacctgggaa agcttggcat tgtatattca gagtaaagat ggtgtgaatg tgtgtgtgtg   86640
agtgtgtgtg tgcatatgca agcacatgtg caaatccaga agcacagtga aggtgagtgt   86700
tccccaaggg ggtttgcagt ggatgcagtg acgaatacat tcactgatga ggatgctctt   86760
ctatagttca gagaagtaag aatgaatcat gaatctttcc agaaggaatt catttctaga   86820
ctccttctta ccttctcagat ctccatcgcc tgacctagag tctcggctga atagcataaa   86880
cctgtatcca tctacatata tttatacatc tggcttagag ccacagcagg gaagaattca   86940
cagcaggatc ttataggcac acagcctata ggatcttata gattacagcc tggatcttat   87000
aggcatccat taaagaaaac tacaggcatt tccgcaactg catatgaatt gtgtcacatc   87060
tgtatgtgct agaaggagtt caagggcatc aatattccta ttgtaataca tctgcccagt   87120
gctagcagca ttacttaagc aaacctatca aaagcctaaa gaataaagat gtggcggggt   87180
gcagtggctc acacctgtaa tcccaacact ttgggaggcc gaggcggggg aatcacgagg   87240
tcaggagatt gagaccatcc tggctaacac agtgaaaccc cgtctctact aaaaatacaa   87300
aaacaaatta gccgggcgtg gtggcacgtg cctgtagtcc cggctactca ggaggctgag   87360
gcaggagaat cacttgaagc caggaggcag aggttgcagt gagccgtgag atcgcaccac   87420
tgcactccag cctgggcgac agagtgagac tctgtctcaa aaaaaaaaa aaaaagaat    87480 aaagatgtgc accagcttgg gcaacaaagt gaagcccat ctctaaaaaa atacaaaaat    87540
tagccgggca tggtggcaac tgcctgtagc ccagctactc aggagagtga gacaggagga   87600
tggcttgagc ctgggaggca gaggctgcag tgagccatga ttgctgccac tgcactccag   87660
tctgggtgac aaagcaagac tttgtctcaa aaaaacatg tatagctaca taattaataa    87720
tatgcaaata ttcttctta gggtcactta ggttttcaac atacagaccc aagagaaggt    87780
acagagactc attctctctc tctttcaatc acacacacac acacacacac acacacacac   87840
acacccctct tcactataat tataattact atgttggctt ccacatcagg ggttagagcc   87900
ttggcatgga gacgcctgaa aggcacccaa ggcaattagt ggtgtccctt ctccaccccc   87960
tacatacctt caggcccttt gcacttgctg ctccccctcc cagtgcacac ccccccagat   88020
ccttgtgtgg ctccctctcc caccacattt tggtcttagc tcaaatgcca cctcctcaga   88080
```

```
aatgcctggc ctggccgcct tcagggctgt ctatatgctc accagcttta ttttctttc    88140
gagaactttc cattcccgga cattgtacta aatgtttatt tgttatccgt ccattatcca    88200
tctccttgcc agcactccct gtgagctcca tgaggctcca agattacaac cacatgccca    88260
gagctagggt ggtgcctggc tcacagctgg catccagtca gtagcaatgg aatgaatgaa    88320
tgatcaccct ctcttcctct ccatccccac cctctccttt ttcacttcct ctcccgcccc    88380
atctcccctg cctccgcctt aaatctgctg gcatgaccag ccctcaggaa gttgtcaggc    88440
aggggaggtg tgtgctctgc acccctctcc ttccatctct ctttcccacc tcccttatgg    88500
gtacctatct ctcctacctg cagctgctcg ctgccagctc tggccctctt ggtgggcaga    88560
agcttaggca ccccagacaa ttgtagggaa attgggcatt ggagggcagc cgtaagaaag    88620
gattcagtac ctgccaagga atgatgaatt tagtctctca cccatgaaca ggcatgcact    88680
ttcagggctc aggttcggtc tctaaagcag aacgtcattc agggcaccct tcagtaccca    88740
tgacccagtg tctcgccttt cctgcaggag tcggtgctgc cactatggtg actcagcccc    88800
tctcttctcc tcattcatta cctgggttct tcctgcagtg attgacagta tccttttttct    88860
tttgagatga agtcttgctc tgttgccagg gctggagggc agtggcacaa tcttggctca    88920
ctgcaacctc tgcctcctgg gttcaagcca ttctcctgtc tcagcctccc gagtacctgg    88980
gattacaggt gcatgccacc atgccttgct aattttgta tttttagtaa agatggggtt    89040
ttgccatgct ggccaggcca gtctctaact cgtgacctca ggtgatccac ccgccttgac    89100
gtcccaaagt actgggatta caggtgtgag ccaccacgcc cagcaagttg cagctcttaa    89160
tagcatgggc accatataat ttactgccca gattgggtca ttttttagag tagaagtggg    89220
agctgttaat aattacgctt ggcctacagg tgtaaacgag accaccctgg gcaaaccagg    89280
cacatggtcg cattgactaa gaggaatatt cccctgcctc ctgcatctcc agccacaaaa    89340
ggagcctcag ctgttggtca aagctgccca atagctgagc ccttgcctgc ccttggacaa    89400
gggagaagac agagggcagg ttccaagaat ggggtgggga tgtggcagga aggacggtgc    89460
aggcccagda gctataatca atgatctggg agcggggttg tggagcacag ggctgtgtca    89520
aggagcaggt gggaggtggg cgggtgtggg acatggcacc agcttttggt gtctgtgact    89580
ctgaacttgg cttactcgca ggtggcttct gcaggctctc caccctccca gctgcgtaag    89640
tcctgcctga ttcaaggaaa acagggaatt tggggtcct gtggctcctc caacgttctt    89700
ttcctttacc tccttgtgta aatgtggcct gatttgtact tggagcataa gtagacccct    89760
acagagcgtg tgtgtgtgtc tgtgtgtgtg tgtgagagag agagagagtg agagagagag    89820
agagagagag agagaaaggg acctatttcc ttctatccct ctgtctgtct tactctcaga    89880
ctattaatac aagccctgag tctggctgta ccccagaac atgtgcccg ccccctacaa    89940
caaaatgctg cccctcccag ctaggtctgt tgtttgttcc ttttctgatt ggcgccaggc    90000
ttatagaccc catgtaggta gaatataact ttccataaat aacctctaac ccgacctaca    90060
atttagcctt caggtttttt tccccctcgt ggtaatggga ttgcagcctg gctgatcca    90120
tcctgtatct tcaggtccca gaaagcagac cctaggtttg acattgcttt ggaattcctg    90180
gtaccccat gttgccttgc acatggcaag gactcggtac atgttgagga atggtggatt    90240
ctcttctacc catgagcagc catgcacttg cagtcttttgc ttgggctatg ccttctgcct    90300
agaagccccc ttctccacct ggaaaatctc taagcaacac ccactttgtg aagctttccc    90360
taaccactat ccctcatccc ctccacagag caaattactc ctatcttgga ttcccataac    90420
acttggtaca aaacagtgtg acctggttat tgcccatgtg cccaccaggt tctaagcagc    90480
```

-continued

| | | | | | |
|---|---|---|---|---|---|
| tcaagtgagg | ggtagggcaa | ggaactgagc | ccaagtatgg | ctgtgggcaa | aacatttaac | 90540 |
| cccttggtgc | ttcagtctcc | tcagattcaa | acaccaacct | ggggctgggt | gtggtggctc | 90600 |
| acgcctgtaa | tcccagcact | ttgggaggcc | gaggcaggca | gatcacttga | ggtcaagagt | 90660 |
| tcgagactag | cctggccaac | atggtgaaac | cccgtctcta | tcaaaaatac | aaaaattagc | 90720 |
| caggcgtggt | ggcacgcacc | tgtaatccca | gctactctgg | aggctgaggc | aggagaatca | 90780 |
| cttgaatccg | ggaaggcaga | agttgcagta | agccgagatt | gtgacactgc | actccagcct | 90840 |
| gggcaataga | gcgagactct | gtctcaaaac | aaacaaacaa | acaacacaaa | cctgacccag | 90900 |
| agcccgtgtc | cccacccact | ggaccgcact | gcctctcagg | gatggaagat | gtctctgttt | 90960 |
| cctacctgct | ctcatattct | gggccctgag | acactcatga | tgcatggatt | ttctgcaggg | 91020 |
| gctcactgag | gcctcctcgg | gggctggagc | cccaggaagg | gaccggccac | tgatacccac | 91080 |
| tcacacctat | caaagacttg | atgatgatga | ttaattcaag | tgggttattg | gtagttaaac | 91140 |
| tgacaagtca | tcaggaggga | cctcagcttt | ctttgtgggg | gtgggttccc | ccaaggtagg | 91200 |
| ctggacttaa | tttaaagctt | tccagttgac | catcccacct | tagggcaact | gaagagtaac | 91260 |
| tttagggtta | ctcttcatct | gaagatgcta | actcagctag | catccagcac | tattaagaca | 91320 |
| ccttggggag | gcgagacttt | gagagaagtg | caggaggctg | gcccactttt | gaagatccta | 91380 |
| catttctacc | caggaggcat | caaatccaca | cttcgaagaa | gatgaagttt | cctgtgagct | 91440 |
| ggtcctgaat | tgtacttggc | tttgtgttgt | ctatgccagt | actaagcagg | acttggccag | 91500 |
| gctggtcctc | catgaatgac | tgtcaaatgg | aaaacagaat | taggaaccaa | agtagtggtg | 91560 |
| tagacaaaag | gggctggaac | ctcagaggag | agagggatca | tgggagattg | gaacatctct | 91620 |
| ggaaggttag | gggaagagat | gacaagtaat | gtgaatccta | aagaaagagg | attagttatt | 91680 |
| gggggtgcta | agtgtggatg | gcaaactaag | gaagcaggga | tctgcatgac | catttggagt | 91740 |
| cagtaggaag | cttggtggag | tgggaggtgg | gagtcaagca | gagaaggcct | cccatgtcag | 91800 |
| atagggaaac | tgcacttgat | cctgggcaag | ggggagctat | ggaaggcttt | tgagcagggg | 91860 |
| agtgatacaa | tgagaacagc | attttggaag | ccagcatgga | ggggaggctg | ctaaaaggat | 91920 |
| acaaggctga | ggttattacc | atgccctggg | tgaagaaatg | cggtctgggt | ttggaaagga | 91980 |
| agggataaac | atgacttttc | aaaggaagac | ataattgcca | caagggccac | cagagagcag | 92040 |
| tcaaaggtgt | gtccaaggtt | ggagctctag | tgaccaagag | aagggtgtca | actttgacag | 92100 |
| aaatgacgtc | atgtgtggtt | gacaaaatga | gaccacatc | | | 92139 |

<210> SEQ ID NO 2
<211> LENGTH: 51719
<212> TYPE: DNA
<213> ORGANISM: Homo sapiens
<220> FEATURE:
<221> NAME/KEY: misc_feature
<222> LOCATION: 1246, 2572, 2604
<223> OTHER INFORMATION: n = A,T,C or G

<400> SEQUENCE: 2

| | | | | | |
|---|---|---|---|---|---|
| ggctaatatt | ttttattttt | attttattt | atttatttat | ttttgagatg | gagtctcgct | 60 |
| ctgtcaccag | gctggagtgc | agtggtgcaa | tctcggctca | ctgcaacctc | tgcctcccaa | 120 |
| gtttaagtga | ttctcttgcc | tcagcctccc | aagtagctgg | gactataggc | acgcgccacc | 180 |
| acacccagcc | aattttttgt | acttttaata | gagacgaggt | ttcactatat | tggctagggt | 240 |
| ggtcttgaac | tcctgacctc | aggtgatctg | cccgcctcag | cctccaaaag | tgctggaatt | 300 |
| acaggcatga | gccaccgcgc | ctggccctga | cagggctttg | taatgctcaa | ataatatgat | 360 |

```
ccaagggtca gagttgagta aactatagaa catagtcctt gcattccacc ccaggggccc    420
aataacgagg tctttctcta aatctcagaa aacactaagc taagggaggt aagttctgca    480
gatgggtttt ctctgtgtgt gtgtgtgtgt gtgtgtatac atatatatat acacacacac    540
atatatatat atacacacat atatatacat ttaaacctttt ggtgctctac ttgtctgcta    600
ccaaaattgt aggcagatga ctgaaaaatg taacacacag aatggcctgc atagaaacct    660
ggctcttgga agtcatatga gtcagttttcc tcaactgtaa agtggtggct cactgtacag    720
acactcagta agcacccagc aaatgaacac cttccagggg ttctgtattg gagtcagctg    780
tatagaatga aaacaaatga caaaggggga aacacacaga gtttattatt ctcccccata    840
aaaaaggccg gaggtgacag tccaagctga gatggcctct cccccaggca ctgtctctct    900
actttgcccc cctgcggcac cttgttcagc tggcatgtca gcattccaca cagcacgaag    960
gaggaaggac aaatggactc tccccatctc tctgcccact gccccctcc ccacaacccg   1020 tttaaaaaat agatatgggg ggccgggtgc ggtggctcgt gcctgtaacc ccagcacttt   1080
gggaggccga ggcgggtgga tcacgaggtc aggagatcga gaccatcctg gctaacacgg   1140
tgaaaccccg tctccactaa aaatacaaaa aattctccag gcatggtggt ggcaggcgcc   1200
tgtagtctca gctactctgg aggctgaggc aggagaatag cgtganccgg gaggcgtagc   1260
ttgcagcaag gcgagattgc gccactgcac tccaagccta ggcgacagag cgagactcca   1320
tctcaaaaaa aaaaaaaaaa aaaaaataga catgggggcc tggcgcggtg gctcacgccc   1380
gtaatcctag cactttggga gtccgaggtg ggcggatcac gaggtcaggg gttcgagacc   1440
agcctggtca gcgtggtgaa aatccatctc tactaaaaat ataaaaatca gctgggcgtg   1500
gtggcgcatg gctgtagtcc caaccactca ggaggctgag gcaggagaat ctcttgaacc   1560
cgggaggcgg agcttgcagc gagccgagat cgtgccacca cactccagcc tgggcgacag   1620
aggcgagact ccgtctcaaa aaaaaaaaaa aaatagacat agggtcttgc tatgttgccc   1680
aggctggtct taaactcctt ccttgagtga ttctcccacc ttggcttccc aaagtgctgg   1740
gatttacagg agtgagacac agtgcccagc ctctctacat ttttttttttt ttttttttaag   1800 acagactctc actcagtccc tcaggctgga gtgcagtggg tgatctcag ctcactgcaa   1860 tctccacctc ccaggttcaa ttgattctcc tgcctcagcc tcccaagtag ctgggactac   1920
acgcctggct aattttttgta ttttttagtag agacagggt ttgtcatgtt ggccaggctg   1980
atctcaaact cctgacctca aatcatccac ccgccttggc ctcccaaagt cctgggatta   2040
caggcatgag ccattgtgcc caaccctccc tgccctgttt taaggagggt cctgttcaac   2100
aattactcta cagaccaatt gcccgcaact atatacttgg cagtgaggaa ctgctgggga   2160
ggctgggaga ttcagcctat aggcacccttg gtggccctaa taactctttt atcttcttct   2220
tcttccccat cagaacctgt tctcaaggaa aagagctaag gtaggctgcc agataaaatg   2280
ctgaggtaag tctgttccag aaaatattgg gacatagact aaaaaattgt tgtttgttta   2340
tctgaaactc aaatttaact gagtgtcttc tttttcccct aaatctggca atcctaatcc   2400
aaggctaaac tcattttcag gacgcaaaag gctctggcct tacctttttga gtcaggacgt   2460 tgcactttga cagaaggctc tggaaggaaa ctttaaaggg agccttccag agggaaatgc   2520
ggtgttgggg taggtctgcc tttggctatg ggctttctgg ctgccggagg gnccagggt   2580 ccccccaggaa agccttctgt ggangtgtctt ttgagagaga caaagcagag gggtggagga   2640
agggcggctc agtggaagg agtgaggaca aaggtgagtg cccctgggca ggaagtgctg   2700
aaagagagaa ggagggaggc caccaggcct gggcctggag ccagcctggg agactcccag   2760
```

```
ccgcccactt ctcggggcct ccctttcca gcccttgct ttcgaggcag cagtgccatt    2820
atttggggaa accagctaac cagataggac agcaaaccgg ggatttatgt ggtgtgggaa    2880
cagctcaggt ttccctccct gtttacccag cagtatttt taaaacagaa atcagcgtgt    2940
gggtaaccgc agctgtgagt tactagctct ggctgtgagg gctggggtgg ggggagtctc    3000
ttcagagccc tctgtccact ggcctgggag ctactgaagg aatgtgcctc tccccatccc    3060
aggccaggtg gagaaggtgg ccctgcggaa gttcccagat cactgcccac ctcacccttc    3120
ccctcccgac gaaggccagc acacctgggg gaggtgtgat gatggttcaa ggtctaaagc    3180
tttagagatc agtcagttta ggggtcagaa cccatggagc caggcaagta aacacaggtt    3240
ccccaagcca gctgggaggg agacacctgg gtgcctttga tgggagaaag agggggccaa    3300
cagctacttg gcactggcca atttccctt gcatgaacat gggcccagtg taaccaacca    3360
tatctttcca tttgtcaaaa aaaagccata tttccagatt ttttataggc aacctgtcaa    3420
cttttaaatg ttggcaatga attcaaaaca ctgccattca attaaaagca gcccagaaca    3480
tggcacgact ggttcttgga ataccaatct gcaatctctg atcttgtcca actctctctg    3540
ctccccattt tacagatcag gaagctgagg cccagagagg cctagggact tagccatggc    3600
tgcagcagtt gttattggga atgccatgag gccaggatgc ctgttatgtg ttctttgccc    3660
agcctagcag tttggctggc ttggctatgc cagaggtctc accatgcagt tctcaagtgc    3720
ttcctgagca tctctcattt gcatagacat gacatttaca aacacatcca tcatctactt    3780
gattctggca atgacaccga gggagcagaa ctggcattaa tccatttttt ttaatggtga    3840
gaacactgag gtttggagag gctggtgacc tgccaaagtc acagtcctag aaagggctgc    3900
agccagggcc tccaattaca gatcaagggt ttttccaccc ccaaactcag tcatctcgta    3960
aaaacgtcag gctccttggg gaatacagct tgagatggat aatcaactcc tcctaaaagg    4020
gaaccataaa tggatgagat acttgggtaa actgaatatt cttgtaact taaagttaat    4080 tgaaaatcca taggttatca atttccaag caggagaata aaatagaagg tatttcaaag    4140
agcaattata gtaggcatgg cttaatcttt ctttgatgat tctgaaggca tttcagggga    4200
atgtaatgcc ttagggcatc attatgaaca ccaataatta ctgtgtaggg ctgtgacgca    4260
aattctcatc aatccctcc tggctgtcgg ggtgttttca gagaggatca tgcagggagt    4320
gtgaacgtgt gcctgtctgt ttcttgctgc tctctccgcc tttgtcaatt tcagggtgct    4380
gttgtggaaa atgcagtgtc cctggaaggg ggaggtcact taaccttaat gagcttctgt    4440
ttctttatta aaatggggta atgcagactc ctatactcac tgtcaaggtt ttgtggggct    4500
cagatgtcag tgtcagagca ggaagaaact ttagatcatg atatgcacca gcttcattct    4560
gccatggaaa aatctgaggc ccagagaggt taggagcctc gtccaaggtc acccagccag    4620
ggagagggtg ctagaacctg ggtttctgc ttcctaacct cttcctgaa tataacacta    4680 tggaagaaaa agatctggag gaacggaaag atgaacacat gattcacat gcaaacaata    4740 ctggggtctc tctgatcaga gaaggtgtga tcttccagcc tcaggagagg ggccatccaa    4800
gtcctggagg aggtgaaccc cttagttcag ggctggagt agcctgggg cagcagagac    4860 actgctgtga ggtttatagt ttcatgactg tcagagcttt ttaaaatgtg gtaatttaa    4920 gtgtgcagcc tccagggtc tttcttcttt taattgaaga aataaaccat ctcccctaag    4980
gcatgcttgg cgaaggagaa aggcaggtgc aaggctcaca gaggagagca gcagcctaga    5040
agggctctgt gtcatgggga agtaaaacat cccagaaaca gagagcagaa ggccttgact    5100 gagcccagg agaggcagga caccaggggt gcacacccat aaacacacac atacacatgt    5160
```

```
atgtctcctc cctggagcct gagagtccct atatacagca ggtgcatgtg ggccacacat    5220
cacacaaaat tgaatacagg caggctcaga gcaccagcac acacgtatgt ccttgacacc    5280
cttagagata ctactaagca cgtgtgtgta cctgctcacc catatggcag agcccctgga    5340
tctgggcaga aatgccaaag caggggcagg cgcgtgtgcg cgcacacaca cacacacaca    5400
cacacacaca cactagcaca gccacaaaag ctcaatccac atccagcatt cctaacaaca    5460
cacacacagc tagacacgct aggagacaca tcaggacaat gtttccactc ccgctgccat    5520
acacatatgc aggtccacat tcaccagtgg ggtagggtag agtctcatca gtccagactc    5580
gcagacagct ggacacagag gtgatctctg aaacccaatg tctacacact gtggtctttg    5640
ttacacacac acacacacac attgaaatga tgtcctcagc cttggttat ttttggtttc     5700 ttctgagctg gagtttcact cttgttgcct aggctagagt gcagtggcgt gatctcagct    5760
cactgcaacc tccacctccc gggttcaagt gattctcctg cctcagcctc ccaagtggtt    5820
gggactacag gcgcccgcca ccacacccta ctaattttg tattttagt ggaaacaggg       5880 tttcaccatg ttggccaggc tggccttgaa ctcctgacct cagatgatcc ttccgccttg    5940
gcctcccaaa gtgctgggat tacaagcttg agccaccgca cccggccgag ccttcgggta    6000
ttttgaaagc tgaatgtgtg gttacatttt cttttctttt tcttcttttt tttttgagac    6060
ggagtctctc tctgtcacca ggctggagtg cagtggcgcg atcctggctc actgcaacct    6120
ctgactcccc ggttcaagtg attctcctgt ctcagcctcc tgagtagcta ggattacagg    6180
catgcaccac cacgtccagc taattttgt atttttagta gagccagggt ttcaccatgt      6240
tggccaggat ggtctccatc tcctcaaatc gtcatccgcc cgccttggcc tcccgaagtg    6300
ctgggattac aggcgtgagc cacagtgccc ggcctacgtt tcaaacagc aatagcattc      6360 gcctcctctg tcagtttaac ccccatcaca actcccactt ttggcaccta aacagttaat    6420
ttcccagttc atgggccttc aaagtcctgc tctagtctct ggaggaactt tcacctacag    6480
aggaaggtgt aagggaaact agttcatgga tttaagtaga aacatttag gtgtagcttt     6540 cacatacaga ggagtgagaa aaaactgatt catggatta tgatggaaaca ttgtagtatg   6600 aacccagcgg agggtctggg agcgccttct ggtggtgaga attagaaccg cagcactttc    6660
tgcaatgtgc ccaggccaga aagctctacc ttctgatagg acccacttct gaccctagaa    6720
tgggggaact gatggaggtg tcaagccact gtggtcccac agctgcatgc aggcacaggg    6780
gataggaaga gagctaccta caggttacta aaccattccc ttttaaaaca gcaccaggct    6840
tatgtctact ctgcgcttcc attttctagg tttaagtgg aagatatgtg aacacccagt      6900
gggctggatg gctgtccctg ctacaagtct gtgatgtctc cgtccagtgg cagagctgga    6960
aggcaggtgc tgtcggggct gcatctgcct tgttcaccag cataggccta aaaccatgga    7020
gggggtgctt tggcttagat ccccacttgg cctgtgtgtg taagaggctc tcaggcacct    7080
taatgctaca tcaccaacca aacctcctga tgattctttt aggttctccg tttccaggca    7140
gattcacttc tgtagattta tttatttatt tttgagacag ggtctggctc tgtcccgcag    7200
gctggagtac agtgatgcaa tctcggctca ctgtagcctt gacctcaact tcaagtgatc    7260
ctccaacctc agcctcccag tatgagggac cacaggtgtg caccatcaca cctggctaat    7320
ttttgtactt tttgtagaga cggggtctca ccatgttgcc cagctggtct caaactccta    7380
ggctcaagcg atccaccaac cttggcctct gaaatgctgg gattccaggt gtgaagcacc    7440
gcgcccagtc cctgacttct gtagacgttt gtattgttta catctactgt gtgcaatgta    7500
cgagatgcag tcaggtgtct ggatggacca ggggatctgg catcttatag acttgggttt    7560
```

```
gaaccccaac tgagccattt actggctggg tgactttggg tgagttctta aacctctctg    7620
acccttaagg tggtaacagt atcaccagtg aagttggtgc acacagcagg gcccaaactg    7680
acatctcaca gcacccagca ggtcactgtg ggcatgatag gatgatgggt cactgtgcca    7740
gccctgaagg agttcaagtc cagataggggg aaggtggtgg accagaccca gacagagatt    7800
ctgagtcgct gctgagactg ggtgagggta gtgggtacat gggaggacat atagcccggc    7860
agcccagggc tggagtccac actcaggttg gggcagcctg gtctgcctct cctgcaggag    7920
acttttccag gcaggcttgt ccctccagaa tgcacgaatc aaatcctctc aggatcagtc    7980
tcattttcct cgtgctgggg gagcaggcta ctcacagaag atgttgttgc aaatgtaaga    8040
atcacatgtc gatccacaaa ctggcattga gcagctacct aggagatcaa agaaactctt    8100
actttgggag ctcctgccag ggctcttttgg gaggtctggc tagctctgga ggaagagaat    8160
gaacttgggg agggcgtgga acagatgagg acgcaggcac tgccattcaa agaggagagg    8220
tctcccggac agggctggcc tgggcaggcc caggagggt ggggctggag cagggacttg    8280
aaaaagggag agggctcagg agactcagag gaggaggaaa gtgtgtgagc agtaggcagg    8340
gtgtgtgtgt gtgtgtgtgt gtgtgtgtgt gtgtgcac gcgcgcgcat gcaggcctgt    8400
gtagggctgg gaaagaacaa agcaaagggg tgcacaaggc atccagaagc cagggcaatg    8460
cagaacagga acaaagcagt ttggctcaag gggaaagttc tgatggaaag caaggaaaga    8520
gaatgttaga agggctgaga gccagaatgc ccagtatggg gtacagaggg caacagaggg    8580
gctgatgttg gtggcgaggt ggggaggagc atttcacagg gaactgggca gctccaagga    8640
tgggctggag gagggacggt cctaaagggg gtggtgggag acaggcagtt agtgatgggg    8700
ggagagaaat gctctgaggg gggctgctgt aggcagggag gggcaggtag caggaggcag    8760
agggttgagc ctgcagaagc ccggagcagt ctgtagcttt ctaatgcttc ctagggaatt    8820
ctgctgctga gtagccatgg gttcaacagg tctctaggat ttgccttgaa ttactgccct    8880
gaggccccct aagtctgggg tctcataaat tcagcgggga gggcacacct gtgtctgagt    8940
ctgagcagcc cagagccccc agtgttgtca gtgaacagct cactgaactt gcagagcaat    9000
taaatcccag ggcagaagaa agagcaggag ggcagggtgg ccccccagctc cctcccatcc    9060 cgggtttggg gagagacacc tctggcctga gactcctcgt ggcctctaac aagtcttgct    9120
ctctctctct tttttttttt tttttaaatt attgtctccc gccctccttc cttcttcttg    9180
ggaatcagaa aagaaacctc aatgcctggc tttgccccctc cctggctgtg gtcaagccat    9240
gtgacattta gacatttcag agcctcctga ctcctgaggc tggagacagc atgaagccaa    9300
atgggcttgg caaacagaag agaggggcag ttaacattct ctgcaatgct ctcttacttc    9360
ccgtttaaac accccctccta ctcggacaca gaccccccaac ccctgtgcca ttgtgctcac    9420
tcccaccttg gaggggtcag gctgtggtga aaggtcaagg tgaaaagtca tgatgatcct    9480
attgctgcca cctccctggg gtgagcaaga ttctgtggtg gctccagctc tcccatggca    9540
gtccacacag aggctgttcc aggttctgga gaggtcactt ggtgtgacct gggaatctgc    9600 atctttttctc tgccaaagca gagggcattg cagcaaccac acctgggtcc cagtcctcaa    9660
caaagtccct ccagctcccg ctgctgtctg caaggtttgg tcatctgtcc ctgcattgga    9720
gaagagtttg cactgtgaat cttgcctcca ccagggaagg ctggtaaaag tccctgcccc    9780 ggggggccctc attgctccag ggtgcatctg ggggccagac ctgtggaccc tcacccttga    9840
gcctcatttt gttcctctta gaacaaagcc atttctggta aataggtttg atgggtttgg    9900
cagcagggaa ggcacagaac ctttcacgat tagcaggctc atgacaattt ctctttaggc    9960
```

```
aagagagaag gttgaggagg aaagactggc agggcttgga gagctggaaa ggaagaaagg    10020
ccctacaggc ctgggatcc catctctgac caccgacccc agcccccaac tctcatagac     10080
tctgatttga tattcttatt taccaaagaa gctgcatgta tttgcatatc aattctcttt    10140
cccatatcga cacgcaggga ggcttcttcg ttttggatca accagagatc accaatgtct    10200
gcagggtgct cagcccctgg taccttggtc actctaggca gcctcctaga tgtgcctctt    10260
aagataggtt ttctgaaatg ggagaggacc acgccccgcc ccccaccatg gactctggag    10320
tctgcggcgc acaaatcctg cgattttaca gatggggaaa cagaggcacg gagaaagtct    10380
cagctttccc acggcccact gggaccagaa cccaggtcgc aggacgggga cagccacctc    10440
ctttttctct ccttgcaacc agcctgagct cgctcagcgg gtgggggctg ccgctatcca    10500
gagcaccctg tttctggatg caaaataaag gcccaggcag tgtttggccc tcctctgccc    10560
acagactttg gctccagggc agtctccgag agagaagcct tgggtcccac tggtccgagc    10620
tctgcgtgct gagtctagag gctgcagtct ctaagccgaa actagcccag gcctcacagc    10680
cgccttcccg ccggtctccc actgccttgg cggggcgctg gcgccctctg ctggccaagt    10740
ctcgctctgc gcgcaaacgc cccagaaatc agccggaagt tccctggggc cccacaggag    10800
tgaggaccca cctggattca ctttgtcatt ttttttttagc tgcatgacct taagaaagct    10860
aatgaacctc agagcactac ctgtgaagtg gaaataatag cgcctacact tcagggtcgg    10920
tgtaaggatt gcatagaata ccgtatagaa agcacccagc acattgtagg tatgtttaat    10980
ggtagcgatt attaataatg cccaactcac atggtgagat gagatctgag aagcctcctt    11040
ataaaggtaa atgataacca agtcttgttg caaggcagct ggtgtgttac taatacatca    11100
tgaggtggtg ggccctctgg ggactgtcag gagacagcct ctgttttatt aggaaataaa    11160
acagaatctg gtctgctcca gttttcttcc ttttatttac tgcattagaa aactttcatt    11220
ttatttattg cctattctgg gggttgaggg tgagggaag gcatgactcc agccaggtag     11280
gatacaaaag tatctcaccc cccaggaggg gtttgaggac cggccctccg gcttttagag    11340
aagggcagct ggcttctgtt gctaacgatt tggatttggc ttttaacaga atatcaaggt    11400
gaaagtgaaa ggagcttttc actccttgga gagtcaagag ggtgtggggt gggacctcca    11460
ggggaatgaa gagtgagcga gggtgctggg gggatcccag acctaggaat cagatctggg    11520
gaaggggtct gcaagacccc tccatgagtc aagaaaagcc ggtgggtgga tggtgagaag    11580
gaccagtgaa gacactgttt gctggagttg tcccagccag tggctatgac tgagactgtc    11640
ccatggcgtg tgcccaggggt cctgccattg gatgatggga cattctttt tttttttttt    11700 tttttgagac ggagtctcgc tctgtcatcc agagctggag tgcagtggcg caatatcaaa    11760
gtcgctgcag cctccacctc ccgggttcaa gcaattctcc tgcctcagcc tcccaagtag    11820
ctgggattac aggcgtgggc caccacatct ggctaattt tgtattttta gtagagatgg     11880
agtttctact ccatcaggct ggtctccaac ttctggcctc aagtgatctg ctgcctcggc    11940
ctcccaaagt gctgggatta cagacgtgag tcactgtgcc tggcctggat ggaacattct    12000
gctctttctc catctgctgc ctacccatga tgtcttggga ctcctagaac cctaaaggaa    12060
gcccctggac acgcaggaag gtgtggagag gagttctcat acttgcactt gggaggaggg    12120
ctcaggagaa acagaggctg gcaacacccc ctcacacact ggtcctctgg agggccagtg    12180
tctacagaca ctgtggactg agtccacaga gaggaaaggg tcctgccttc atcagaactg    12240
ctcagcaagc agttccatcc caggggtcc tgcgaggtaa gggagggca gctagctagg      12300 tgaggggctg agagagtggg gagggaaag agggaagaag agagtgagag ggagagggag     12360
```

```
ggactgagcc gattctcagc tccttgaccg tttgctgagc tctgtctgag tggacagatg    12420
gtcccaagtc aggccacacc agagtggcct ttctgctccc ctacaccctg cattcctcaa    12480
cattgctggc cccggagaga ctttccttca gagaagcaaa tggctgggga atggtgaaag    12540
acactgcaga gaaagaaag cacagcctgc tgccctggga attaacatga tttaggagac     12600
ctgcaggtca ccccctcatg actaaaagcc atcctggaat gaaggtctgt ggctattcct    12660
aggcaaaact gtctgataag ataaaatagc tcaactcctg accattaagt cgtgaaggcc    12720
atggccatcg taaatctcat ctttccggcc ctctggcctg catgcagtgc agcccagcca    12780
gtcggtggca gccaccttgg taggaagggc cctcatcctc ctggctgtgc ccaaggact     12840
gggcaggctt cggtgccaag ggtagtgcga gcacttgaaa gccgccctgt atgtttattg    12900
ttttccccag gtgatccaga attactcccg aactctacca gctgaaatcc tcctcaactc    12960
acatcagaca agacggccct gccacttacc tgtcagatca ctttgggcag gtaagctcat    13020
tttcctgaat ctttacttcc acaccttaaa atgtgagcaa tactatctcc ctggcaaggt    13080
tgtttgtgag ggtaaaatga aacaataatc acgggtgcat cctggagctc tttcttacaa    13140
ggcgtgcccc caaatctgtc ccctctttct gaggatgccc ttcccctatt gtctccctgg    13200
ccatttccta cccattctca agggccatga tctcagggag ttctcctgac tcacccaggc    13260
atattggatc tcctacgtac tgctacgact gcacacaggt gcaggaaatg gctgtttgct    13320
ttgcgtttga ggaacttgga aagggagacg tggtagggaa agtagtggtt aggggcactt    13380
tcagactgaa ggatgtgggt tggggaatac gggattcttg gagttgagga cgccgcttct    13440
ctcgtctcta gctaatgtga gaaagaccct tctggacact aagcctgcaa ttccactggt    13500
ggctaccagg tgtccgtggt gtcctggggc gggtgtaatg agagcgggag cctgtgaaac    13560
caaaagcatt gttttttataa attcagcact cttcaatccc tattaataag gttagcggtg   13620
cagttcttgc gtctcctgcc ctgcctcacc ttgcaatcat attcattggc attcctttct    13680
tccaagaacc cacctaggag gccttgcagg agatatctct ggtgctggct gttcctgcag    13740
tctgaaaagc cagttaagat acaaatatgt gagaggacac tgcttgaatc tgatttcatt    13800
ttttaaaaag tttaattatt cacagacttt gcttctttct gactagtaat gtgacacctg    13860
tgactcagtt caagatggtg tgtggtgacc ttgcagttga aagcactga gcgctatagc     13920
catgccaaga aggttgccct cctgggacca gcaaaaattc catccagggg gccatctctg    13980
tcaggcttgt cctgactatc ttttggaga ggcggcagag tggagtggtt aaaagcatga     14040
ttctggagcc cagctacctg ggagcaaagc tcgtctctac cgcttaccag ctctgagagc    14100
ttaggcaagt gacctattct ctctgtgcct ctgagttttc atctgtgaaa tgggagtaac    14160
aatagtcctg tctcacaggg ttgctggag gcttgaatga gttaatgtcc atggggtgct     14220
gaatcagtgc ctggcatacg gtgaaggcca tgtgagcagt aaatattatt attattagaa    14280
aggttggctg gcgtggtgg ctcacacctg taatcccagc actttgggag gctgaggtgg     14340
gcagattacg aggtcaagag ttagagacca gcctggccaa catggtgaaa ccccatctct    14400
actaaaaata caaagacat tagccggtat agtggtgcgt gcttgtagtc ccagctactc     14460
aggaggctaa ggcagaagga tcgcttgaac ccgggaggca gaggtttcag tgagctgaga    14520
tcacgccact gcactccagc ctgggcaaca gagtgagact ccatctcaaa aaaaaaaaa    14580
aaagaaaga aagaaagaaa aaaagaaag gtcccaacct actcacttat tgttcacttg     14640
catcaaaatgc taggttcagt gtattgttct tgtaagatta gaaatggaga gatgggtcag   14700
aaggggttgg tcaaaataga cctctcaacc caagcagaca gggctggctt catggccggg    14760
```

```
caaccatgca ggacccaggg ctctaagata agaaaggcac gtagtttaat gctttgctgt    14820
cccatcttga tactgttttt tttttctttt tttttggaa atggagtttc actattgtca     14880
cccaagataa agtacaatgg cgtgatctca gctcactgca atctctgcct cctgggttca    14940
agcaattctc ctgcttcagc tccttgagta gctgggatta caggcatgta ccaccacact    15000
cagctaattt ttgtattttt agtagagacg gggtttcacc atgttggcca ggctggctgg    15060
tctcgaactc ctgatcgcag gtgatccacc cacctcggcc ccacaaagtg ctgggattac    15120
aggcatgaac caccgtgcct agctgatatt cttaatttat gaaggaaggg ccccaaattt    15180
tcattttgca ctgggcccac aaataacgta gcaggtccca caaacaaatt cgtctagatt    15240
cagagggccc cttgccttcc tcctctgctc acattcgttc ctttctccca tcacaggcgg    15300
gtaccctacc ttgggggatt tgccccagaa taagcctttt ttttcccttc taacatttta    15360
atgaaaaatt tcaagtgtat agcaatgttg aaaagatttt atagtgagca cccatacacc    15420
tgccacccaa agtctaccat taatgtcttc tggacttact tttgccgtct tattcatact    15480
ctgcctggac tgtcctcagc tacaggactc acatctcttg ccgacagctc taaggcttcc    15540
agtcctgctg tctggaccaa gaaaggcttc ctgggctctg agtgtcaaat ggcggccttc    15600
aaggaagggg aatggtggaa aaggccgtgg ggggttttgg agaaattgct agggaaagac    15660
tggcaccaga gttccaccag cccaggcaat gggggtaca gaacccataa gatgagttct     15720
agaaaagcaa ggaaggtttc gttctggagt ttgtggactg aggtttccat ttgtgactag    15780
gattctcatt ggttccttat gtagtttctt acgccctgca tagtcttcta agcatttctc    15840
acagacgtgg tctgggggcg aacaccagca gccctgagag gtggctaaag aggagattct    15900
tctctccact tcacatcgta ggaaactgag tctcagaggt tccttccctg gcctgcccac    15960
aaccccaggg ctaaaagagg cagaccaagc ccagggcctt gaaccccaac aatgggcctc    16020
tttcttttga tcccatgata gggtgcaaa agcattgcat tccctgggt aattgaaga      16080 aaaacccaa aaaactccaa ctttgtctcc aggaaaaga gggtgtctgg gctatgattt      16140
acctctgagg gtgtggttgc actgagcgtg atcacacttc aaagggttag atctcatttc    16200
tctgcctttc tagcttgggc ccagggctca gaaatgtgtg gactccctca gcccctcc     16260 cagcatccct gccccctccc aactgccttg ggcaggtgac acctgtatta ttgctaaggg    16320
ttaaaaagcc cccaaatcaa taaaacccat taatgagtgt tggtacctcg aaggctacag    16380
ataaatccct tctactcagt gagttcaatc ccataaaaca gctctcccct ttcaatccta    16440
gcattcattt gatagaaaat gtggagaaat tttaaaaagg tgacttacta attgcctgta    16500
aaataaaagg cagatggaag ctttattaca gttgaaggaa gtcgggaata ttaaggtaaa    16560
atgtcaaata acaattgatt ttccttagac ataaaggggc gatttatggc ttcctagtta    16620
ctacaaacga gaattatttt gaagttctga aaagtatgag gagaaataaa gattaaatag    16680
aagatgaaat cataggggatt tctctgggag gtgacttcag tgcccctggg gactagaatt   16740
catgtggcca gtggcctagc cagctgggc ttggcagttt caagatttag aggcaaggtg     16800
tctctgagga gcgggaagt ggctgttttgc tttgtgtctg aggaactagg aaagaaagat    16860
gaagataggg aaagttgtgg ttagggccaa tttcagactg agggatgtgg gattagggga    16920
ttcttgtgga tgggcctata gctctgcttc ctgactagca gatactgggg atctgggaa     16980 gggaagggtg agctgccttt cctgggactt cgatggcatc cttacagtca ggggacactg    17040
tccttgctgg gtcccggaca tcagtgtcta tgtatccctg caagccacag cactatccag    17100
gccctctggt ggctttgctt ggtctgggcc aacctggtct ccacactgac agtcaaagac    17160
```

```
gaggagagga aaaagaactc acggctaggc gtggtggctc ctgcctgtaa ttccagcact    17220
ttgagaggcc gaggcgggtg gatcccttga gcccaggagt tgagaccag cctgggcaac     17280 atggcgaaat ccccgtctct acaaaaaata gagaacaatt acccaggaat ggtggtactc    17340
tggaggttga ggtgggaaga tggcttgagc tcgggaggtt gaggctacag tgagctgtga    17400
ttgtgccacc gcactccagc atgggcgaca gagcaagaca ctgtctcaaa aaaaaggctc    17460
atttccaggc tgccaggctt atgttagcct ggggtcccgc aggagctgac ctgagacaag    17520
tacttgaggg caagttgttt gtttgaggga tgctcacagg aagctccagt aggagggtag    17580
ggaggtgacc cagggaagga aggcagctta caggggcgtg ttgtcaggaa gggcaccccg    17640
gcgggtgacg gaagcttaat tttgctggga aactcaggag ccagcatgga acctgcacct    17700
cagagttatc ccactggaag gatgagggag cgggtactta taccaact  ccatcccgt      17760 cctttgttaa ggctgctgga tggagtgggt gggacactca ttcttcagca ctcccagggg   17820
ccctcaggct gtcagaagtt aggtccgttg ggctccagga tgaggggacc cccagaagat   17880
gcgggagggc gtccgcagca tctgcctctg tgctttccct gtttatctga atcctcataa   17940
ttcccgccac atgcagatca gagccccag ctttatggaa gagaacacag gtttggagaa    18000
gataaagagc attcccacaa ctaggaggtg gggaaagcta ggagttcagc ccagagctcc   18060
ctgacttcaa agtccattct ctttctactt cctgattttt tttttttttt tttttttttg   18120
agacggagtt tcactctgtt gtctaggctg gggtgcagtg gcacaaactt ggctcactgc   18180
agtctctgcc tcctgggttc aagcaattct cctgcctcag cctctcgagt agctgggact   18240
acaggcgccc gctaccatgc ctggctaatt ttttgtgttt ttaatagaga cagggtttca   18300
ccgtgttggc caggctggtc tcgaactcct gacctcaggt gatccgcttg ccttggcctc   18360
ccaaagtgct gggattacaa gcacgagcca ctgtgctcgg cctacttcct gattttgta    18420 taagacacat cccagcagca tggtagactg aagactcctg ggcccactct cagagattct   18480
gctctggcaa ggatgtgttt attggtgaga ggggtgtcca ggaatacgtg cctttttttt   18540
tttttctaga gacagggtct cgttgtccag gctggagtgc agtggtgcaa tcatagctta   18600
ctgcaatctc aaacttctgg gttcgagcga tcctcctatc tcagcctcct aagtagctgg   18660
gactacaggt gcacgccacc atgtctggct aattttttaaa tttttttctgg agttggggtc    18720 ttgtgatgtt gcccaggctg atctttaact tcaggtctca agagatcctc ccaccttggc   18780
ctcccaaatt tttgggatta cagccatgag ccactatgcc caactagaat atgcactttt   18840
ttttttttga gaccgagttt tgctcttgtt gcccaggctg gagtataatg gtgcgatctc   18900
ggctcaccgc aacctccccc tcccaggtcc aagcgattct tctgcctcag cctcctgagg   18960
agctgggatt acaggcatgt gccaccatac caggctaatt ttgtattttt agtagagatg   19020
gggtttcttc gtgttggtca ggctggtctt gaactcctga cctcaggtga tcagccccgc   19080
ctgctttggc ctcccaaagt gctaggatta caggcatgag ccaccaagcc tgacctttt    19140 tttttttttt gagacagagt cttgctttgt cacccaggct ggagtgcagt ggcacgatct   19200
cggctcactg caagctctgc ctcccaggtt catgccattc tcctgcctca ggctcccaag   19260
tagctgggac tacaggcact tgccaccacg cccggctaat ttttgtatt tttagtagag    19320 atggggtttc accgtgttag ccaggatggt cttgatttcc tgacctcgtg atccacctgc   19380
cttggcctcc caaagtgctg ggattatagg cgtgagccac cgtgcccggc ctttttttt    19440 tttttttttt tttttgagac aggatcttgc ttggttgccc aggctggagt gcagtggcct   19500
gattacagct cactgcagcc tcaatctcct ggactcaagc aatcctctca cctcagcctc   19560
```

```
ttgagtagct gggaccacag gtgtgtgcta ccacacccag ataattttttg tgcttttttgt    19620
agagacaggg tttcgacatg ttgcccaggc cggactaaaa ttcctgggct caagtgatcc    19680
tcctgcctca gcttcccaaa gtgctgggat tacaggtatg tgccatcgtc accagccaga    19740
atatgcattt tcttttttttc agacggggtc tcactctgtt gcccaggctg gagtgcagtg    19800
gtgtgatctc agctcactgc aacctctgcc ttctgagttc aagcgattct cctgcctcag    19860
cctcccaagc agctaggatt acaggtgtct gccacaacac ccggctaatt tttgcatttt    19920
tagtaaagat ggggtttcac catgttggtc aggctgatca caaactcccg actgcaagtg    19980
atccgcttac ctcggcctcc caaagtgtta ggattacagg catgagccat tgtgcctggc    20040
cgaatatgca cttttaataa gcatcagcca ggctaggcag gccgggggcc acactcgaga    20100
acatttgcac cacagccact ggctacctgc ccctttttcc ataaggttcc actgccctct    20160
ctcccctcta tctgggtctg ttcttcaggt tcttccctgg gagctctctg agtgacataa    20220
ctgtccccaa gtgctgggag atggagagag gaatcaccag actggagcag gcccccagag    20280
cggagatggg aaggggaggc tggtgttctg aggctcccga ggcagtgaga ggtgaccgga    20340
ggcagtgaga ggtgaccgaa gacagtggct gagaaccagg gaggggctgc gggaaaaagc    20400
cctgggtgca agtcgctctt tccttagcgt cttttgagagg agggatgggg aaaggtgagg    20460
tactagggaa aaccatctgg aaggaggtca ggctgcagaa aagctgcagg agtctggggg    20520
actaagaaaa cagtgggaga ccccgctgca gcccagcacg tgagggtgag aacgtcatga    20580
atgagggaag agcaggcagg gggtggtggc cttgtggcct ctggagagga ggagccacat    20640
gactctgggg tgatctgggg tgaccctcag ggtaagggta cctccctagc actgagtaca    20700
gagggaagcc tacactgcca ggtgcagttt ccctggcaat gcttctcctt ctaacactat    20760
gtgagtttcc tagtgctgct gtaacaaact gccataaacc aagtggcttc agagaacaca    20820
gacggactat gacagttgtg gagggaagaa gtttgaaaag cggggtgccc gcaggctgca    20880
gtgcttctgc aggctccagg gagaatctgg tccttgcctc ttccagcctc tagagcctgc    20940
cgcactcctt ggctcatggc cccgtgtcat tgtagcctct gcttctgcca tcacatctcc    21000
tcctctgcct ctcctgcctc cctctgtcct ttataagaac gcttttgagt atattggacc    21060
catctggata gtccaggata aatcccctcca tcctcatatc cttaatttaa tcacacctgg    21120
aaggttccct ttgccacata aggtaacata ttcacattgg gacagttagg ggattgggat    21180
gtggacatct tttgaggtgg gaagaaggag ctggggttct ttttaacatt tttttgagac    21240
agggtctctg tcacctaggc tggagtgcag tggtgtgatt gagactcact gcagcagcct    21300
caacctcctg ggctcaagtg atcctcccac ctcagcttcc tgagtagctg ggactacagg    21360
tgtgcaccac catgcccaga tgatttttgt attattttaa tattttgtac acatggaggt    21420
cttttaatgc tgcccaggct ggactcaaac tcctgggctc aagcaatcct cccgtcttag    21480
cctcccaaag tgctgggatt acaggtgtgt gccaccagac ccagcccgga cctgggttc    21540
ctgtctcatg tcagccttag caatctgggt gaccctgggc aaggcctatc ccctctctgg    21600
gcctttgttt ctccacctgt gcaatgaggc tgttccctct ggctccttca ctctgagttt    21660
ttcagttggg agaatatctt ggcagggagc agaggtcggc gggggtggtt gtcattccat    21720
ttcagggcct ctcagagtcc tgccgtggtg tgcactgtgt gtgtgtttaa ttttctacat    21780
ttggatgtga tcctaatcca ataaatgctt aggagacttc tatagaatag attaattttt    21840
actagaaaaa aatataattg gctgatgtta aggctactgc cctgacaaat ctgccttggc    21900
catatatctg agaaggtaaa agacccgcta cgcttgcaca taaatatgcc atcttcccca    21960
```

```
caggccctgg agaagcaccc cggggaggtt tcccttggtg atttattctt cattaataag    22020
ctctatgcta tattaggatc agatttatga ctctgccttt ctaatatttc tgacatttca    22080
tctgaaaaga attacaaatg aaatcttgaa actttgccac ttctccctgc tagtgctctg    22140
gcactctgtg tccaagggga gatggtgggc tggggagacc ccaagaagca gggacagagg    22200
catgtttctc agggaaagga gcgatcagct tgactttggg agagctttat tcagtttgca    22260
agcagcttgg gaggtgagcg gttcaggcga aaggctgca gaccagacca caagcccagc    22320
agcagcagtg atgcctgtaa catgtatgag atggtggcag gcacattcat tcattcaaca    22380
gctatttgtt aagcacttta ctgtgtgcca aacactgtgc tgcttggtgc ttgggataca    22440
ggaaagaata aaagtgaagc agtgatgaag atcttggcct tcatgcatat ggtgttctag    22500
cagaggtagg ggagtgtcaa gcactgatga atgaaaatcc tgaataggta aaatatatca    22560
tatgttcaca cgtggtaagg gctatggcaa aacagaaaca aaccctccac acagggaaaa    22620
gggaaccaag agtgccgggt ggtcaagttg caatgttaat taagaaagca cttcaactca    22680
tcaactcaag gaaccgtatt atccccattt tacagatgag gacggaggct cagcgtggat    22740
taggagctac acaaagacac aaagggaact ttgcacaact tgaaagtttg caaagtgccg    22800
tctgagccat tagtctccct tctccccact gactgcccta ccacaatcac atggggacca    22860
taaaaatact gttgcctggg tcccgctccc ctgaggcttt gattcaattg gtttggatgc    22920
agcctgggac ttggcatgtg actcttgtgg tgccaggact aagaatcttg tgtgaactcc    22980
cagcacagcc tctcaggcct ctattttctc acctgcaaga tgtgggtaaa aatattcacc    23040
ctgtactgca agaggatgtc aggagtgaag gcagaaacac agcaccagcc ctccaggacc    23100
cccaacccct cccccacccc aatccttcac ccctgttgta ccttctgacc tcaaagtggc    23160
tctgattatt tcactcccac aggccactgg ctcagaggta tagagctcac ctgtggcaga    23220
tggagatgcg gatctgaggc ttctgatgct gccacaccca gcggcgcccc ccaaattccg    23280
ggcccctgga tgacatctgg tctgttcctg cagcatcaga gcacaataga gccagccacc    23340
agtcccagcc ctgcctgcat cccatccatt cctgggtgcc taaccccgag gatccctgg    23400
cagtatgatg cggacctgtc ttggatccca gggatatgct ggccacgggg aggagccgga    23460
aaccaacctt tgtgtcactg tgtagtgaca agtgcctttg gaggtcacaa tagccagtgg    23520
tgatttctac cactgccccc agcagccaag gtggcagagg agccctgtca gtcacccca    23580
ttctgttcat ggtctcacgg tgggctccac atggggggtg gcagccctct cccccacccc    23640
acccgacccc tttcgacaga tagggtaata caaatacaaa taacaccaaa agattgagtt    23700
gctgggcaga aagggaccaa aggccagtgt gtgtgtgagg ggtgggggca gggcaggaga    23760
ggagcagcaa aaggctgtga ccgcctggct gagcactgga tactcactga agggcaggga    23820
ggcttcctgg agaaggagac ctggcagggg ctgagggagt gatgccaggc atggggttt    23880
ggagggaccc caggcatggc atgcctccat tcctccctgt gctatccact ctatataagg    23940
ggtgctgtgc agggagacag cttgcatcca agcagggagg cagggaggat gagaggcaga    24000
gaggagccca gctgggttga tgaaagtct gggaaatgca ggaaatccag gagggggaga    24060
atgattccaa gctgtggcct gtgatgggcc ttgaaaccag gtgtaggcac ttggatctga    24120
tcgctgggga gccagagctg cttcctgagc agcagaaggg caggatgcga atcagactag    24180
gggcagtggg aggaactgag aggcctcagg tcaccggaga aaatgcacag ggccgggagg    24240
cagagatgct cctgttttct tgctctgggg ctcaggacag tcagtcaccc tgagcttcag    24300
actcagctca ctccattttgc agagatcctg acggcgatgc ttcaggatga tctgggaaga    24360
```

```
gtcaatgagg taaaatatgt gaaatatgcc ttgaaaacta caaaccacag cacatgttct   24420
gtttttgctt ctgcttgatg gactcagtga gatggtgggg acaagaatta gagaagccca   24480
tgaggaggcc aagggcacc  aaatagaccc accaaggacc agtggggact tagagaaagg    24540
atgagtcaga gagaaatgac aggagcagaa ggcaggcctt gtatggagga tgaaggtgaa   24600
gatcatacac cattaaactt gagaaagagg cgggaggagc tgccatttct tgagtctact   24660
ggatgccagc agtagtgctg ggcaagggct taacaggtgg ggaaatcgag gcacagagag   24720
gttaagtagc ttgcctaaga tcacccagtt agtaagtagc agagcctggc agcttaactc   24780
caaagtcttt gtactaaagc cagatttttcc aaatttgccc aactgtaaga atcacctggg   24840
cctgtaatcc tagcattttg ggaggctgag gtgggtggat cacctgaggt caggagtttg   24900
agaccagcct ggccaacatg gtgaaaccct gtctctacta aaaatacaaa caattagccg   24960
ggcgtggtgg caggtgcctg taatcctgta atcccagcta cttgggaggc tgaggcagga   25020
gaattgcttg aaccccaaag gtggaggttg cagtgagctg agattgcgcc atcgcactcc   25080
agcctgggca acaagagaga aacgccatct caaaaaaata aaagcccggg agtttattac   25140
agatgcatat tcccaggcac ctcctacgga ggttttgagt tagtgagtcc aaggccttct   25200
gcctcttccc aatgtattca ttatgcacca tcattactct tgttcagata caatgtgagt   25260
gatagcttgt ctctggcagc acagcagcca cacccaacca atccagacct cagtcatgag   25320
ggtgccaatc acagctaaca ttttttttt  tgagacggag tcttgctctg tcgcccaggc    25380
tggagtgcag tggcacgatc ttggttcact gcagcctctg cctcctgggt tcaagcgatt   25440
ctcctgcctc agcctcctaa gtagctggga ttacaggcac ctgccaccat gcccggctaa   25500
ttgtattttt agtagagatg ggggtttcac tatgttggcc aggctggcct tgaactcctg   25560
accttgtgag ccacctgcct cagcttccca aagtgctggg attacaggtg tgagccaccg   25620
cacctggccc acatagctaa catttaatca gcacatacag gccatgctc  atcatttttt    25680 gcgcacaatg ccatttaacc ttcacaacag cctgtgagaa ggtgtgttag cctcattta    25740 cagaggaaga aactaaggcc cagagaagtt atgcaacttg cccaaggaca cacagcttga   25800
aggagctgag gtttaacccg tttctacggg gtctgaatcc tccttaccac ccctatctcc   25860
cctgactccc aggttgtgtt tggtgtactt gggtagtgtc cagctgacaa atgagatgtt   25920
ttagcttcag acagtctatg ccatgtagaa atgcacccag gactgtgcat attagggagg   25980
tttgcaaatg tgtccacatt agataatttt tctcaaaatg cccctcactg aacttctgtc   26040
atgcagtatg tactgagcac ctgcctcttg ctaggtcccg ggagagagga tgaagagggc   26100
agagccccca ccctcagggg acctgaaaaa tgggagtcct ttgtgctcat ggaagcaggg   26160
ccttggggcc tcagcactat ggacatttgg ggccgggtaa ttctttgttg tgggggggctg   26220 tcctgtagat tgcaggatgc tccgccgcat cccttgcccc tgccctctag aagccagtag   26280
caccctccag ttgtgaaagc cgtaaaatgt ctccagacat tgctcccagt tgagagccac   26340
ttcattaaag aaaaaaaaat aaaaaagatt tctgtatcct ctatacatgg actgaatttc   26400
actgacattt ctctaaaata actgaatcta tttctatact catttttttt taccagctgc   26460 catttattt  atttttcttt tctttctttt tttaagaaac agggtctcac tctgtcaccc    26520
aggctggagt gcagtggcgc aattatggct cactgcagcc tcgacctcct gggctcaagc   26580
aatcctccca ccttagcgtc cccagtagct ggcacgccac tgtgcccggc tatttatttt   26640
attttatttt atttttttg  tggagacagg gtctcccaat gttgttcagg ctggtctcaa    26700
actcctgggt ttaagcaatt cttctgcctt catttcccag agtgttagga ttgcaggcgt   26760
```

```
gagccactgc acccggccat tttatttctt aacaaagcac aaatcaaatg tacaatgcag   26820
ctagattttc ctttataaat aatgtctaat ggatttgttt ctgtcagctg cctagaacat   26880
tctggtatcc cagacagaag tgcaacacca ggtggaggtg ttgcagctga gaagttctga   26940
ccagcatacc agcacccccct taaaagctgt ctatacttgc ggttctcagc taggctgcca   27000
cagaatcgcc caagtcttaa aaaaacaggt ctctgtccta ctgcttgaga tgctggttct   27060
ctaggtctga ggttctggca cctgtgtgtt tttaaaactt tacaaataat ttaaaagcgc   27120
cttcaagtcc acaacaacag aatatttccc tccactcctc attgtcctgg agttctctaa   27180
cagtgcagtt ctacaactgg acacacgatg tcgcttttca gccacagttc tcactaagcg   27240
gccccacagg gcggcaggtg ccttctgcag agagagagag agggccttgg ctgacaggcc   27300
aagaccggga atcctggctc ctcctctgta cagacttttc acagatgtga actctcccta   27360
ctccctgtct tctgccccca aatgaagcct ctcagctggc aagagctgag aactaccaag   27420
cgagccattg ctaatttcta ttgtgtttgg aaccacaaaa ggcagaatta ttaaggctgt   27480
aaaggacctc agagcatctg gtgcagtgag tttccaactt gtgaaaatct gatgtgatct   27540
cggacaagtc acttaacccc ctgcctcaat ttcttcatct gtaaaatagg ataggaatat   27600
atcttgcccg tctgattgtt atgaagacaa agagaacaaa tgcacataaa gcccgtgacc   27660
atgtgctttg tgaatggaag ctttaattta ttcattcatt tatttattta tttattttta   27720
tttatttatt tattttgag acatagtctc gctctgttgc ccaggctgga gtgcaatggt   27780
gcgacctcgg ctcactgcaa cctccatctc ccggattcaa acaattctcc tgcctcagcc   27840
ttctgagtag ctgggattac aggtgcctgt caccatggcc agctagtttt tgtatttta   27900
gtagagactg ggttttcacca tgttggccag ggtggtctca aactcctgac ctcgtgatct   27960
gcccgctttg gcctcccaaa ggaagctttt atttttatta tagttttaca taaggataaa   28020
ttcagcctta gtgaagggaa gtgacttgcc caagatcata cagtgagact gctggatctg   28080
gggctctact tcagaatttt ttttgagat ggagtttcac tctgttgccc aggctggagt   28140
gcagtggcac aatctcggct cactgcaacc tccacctccc gggttcaagc gattctcctg   28200
cctcagcatc cctgatagct gggactacag gctcccacca ccacgcccag ctaatttta   28260
tatttgagt agagacaggg tttcaccatg ttggccaggc tggtctcaac ctgcctggcc   28320
tcccagagtg ctgagattac aggtgtgagc caccacgcca gtctactgcc attgtccatg   28380
atttttccta cagggaaaat cacaatccca gaagataaga caaagaacag taaaaggtgg   28440
cttttgaggc agtgagttct acctgaaggt gggaacagcc cagagtgtct ggggacagag   28500
tggtaaattc taatcaagcc ttcccatggc tttgtggatg aggatgagtt ctaccctga   28560
agctcggcct gttcagccat aaaatcagga taatggtggc tgtgcctcct tagagtagaa   28620
tgagaatcag agcagaacaa gggaaagctg cagtgacttg tcaggtgtca accttcagca   28680
tgatgggaga gccatgggac ccttcccctt tccctaagag agccagccct cacagcaggc   28740
ctgggatcca atgcccagca cccagctggg agcccaggga ccttggccaa aatctggttc   28800
tgcttcaact tggtgcccgg cctttgtcaa gtcacttcct catttgcaaa ctgggagagt   28860
ttggatgaaa ctattgaatg aaattatttt gggggtttct ttctggctct cacagtcctc   28920
gcatgctcac catgttccct tcaatttcat tagcacagcc caacaaaggg ttaagcagtg   28980
gcagttcctc tcgttctttg gttaggacag gaaggtcagg ggtgaggcca atacaagagg   29040
tagccgccac agctgatgct ggaaatgaca atagttcttt cctagactca tatttgtccc   29100
ctctccctga agctttgcct gcagtgccct tgtaaagaag ttggcaagaa gcaggagtga   29160
```

-continued

```
ggctcagccc ctctctgaaa tggatacgcc ggttgctccc cctcatggct ggtctcattt    29220
gccttcttca ttttagaca cattccaaac ttttcagcaa attatagtgt ttgccaactg    29280
gccgtctggg gcccaggaga gatgctattt atagcgatgc tgggatgctg ccatcccaga    29340
gcagcctggt aagaaacgga gccagagtgc ctggagtgg cgtcctgcac cctggggaga    29400
ggccagggcc ctggagcagg gtggcaaagc tggtggcccg tggcaaggac cactggcaca    29460 tccccctgcct gcctgggccc tggggtctgt gcccataccc cacacggggg gctgcttccg    29520
tgctccttgg agagacgatg gtgctgtggg gccactgagc acagtaaagg ctaagaccca    29580
ccataggtca gcccttgctc atgctgactg ttgccccatt tcccttcatt ctctcactcg    29640
ttcattcctc agaatctgca tcctggtttt gtcactacct ggagttgtaa agataccacc    29700
aagctcacct tgtggtgtga gccttgattt tccccatctg tgtaaagggt ggatctgagc    29760
tccaaagttc cttctagtca tatgcagagt gcataataaa tgtgtttgta ttcccactgt    29820
gctcagtggg cactgggca tgcagaagag aaattggaat aaatgtgacc cttgtcctcc    29880
agaggctcag taccagactg aaccaggac ccagatgagg ggcctaccca gagagggcag    29940
cgtgctctcc tatttgtgtt aggcgttacc atttacaaag ggctttacgg ctttgaaggt    30000
ccccacaacg ccctgaggag gtgaagtgtg gcaatgcccg ttcacttggg aaaatactgc    30060
atctcagaga gaccaaggga ctcgcttaag gtcacacaga tacagtaagt aagtagggaa    30120
agagctgggg cctctgggct ccttttccgg ggctctggcc tcggttttaa cccgttctcc    30180
tagacctctc agtctctggg cctccccctct gtgttcccca ccccactttt ccatcaagag    30240
ctcagttctc ttaagttcta tattctctct tccccaccc tagaaatctc tgcccgcttc    30300
cagaaaaggc tttgattccg tcattttttgg catttcccac ccaggaatca aggctgcctc    30360
ctctgtgagg aaggcgtgtg gaaggcgagc agctgaggac acctcttttt aagagaagct    30420
tctccatgtt cttagccagg ttatataact tcttttgctt cttttcttttc cacattctac    30480 atattttca caatgaggat gtgtcacttc tatagttaaa aatggaaatc ttcatttaaa    30540
agaacaatca gacacaaggc aaggtatgct taccttccca atgaccaagg agcagggaga    30600
cattggtcgt ggaggccata ggtgaccagc cttgagggaa gggaaggaag gggaggtgca    30660
gggaggcgca gcagaggcac ccgagtgtgc tctacgaatg taagtctgcc agctgctcct    30720
ctgtgcctag caccctggaa agcgcccgca cacagtgggc cctcagcaaa ctcccactga    30780
gcaaagggcc ctgtgagtaa ggacctagaa gcagggtgtg cttgaggcat ggggtgggag    30840
ggcatccagc ttggctggcg gtgggagccg atgcaaaggt gagctgagac cagacggtag    30900
aagaccttca gtgctgggcc gaggagggtt ccttcatccc atagagaaga gctgccatcc    30960
aagacagaag gctggggagt gacatgttga aatcagtatc ttaggaaaat aaagccactg    31020
gctgggccac tggctcccct ttgtagaggg gtctacgaag ctcccgaggt ttcagatagt    31080
ccctgagagc ccttcccctc gcgatgggct ccgtttgagg catgtccagt gtgaaaggac    31140
cacaggccac ctgagggaca ggaccaagca gagagctagt gacagaatgc ccagggctcc    31200 aagcagggc tggagaggtg ggagtggtcc ccaccttgag agccaaaggg gctgagggct    31260
gagggttgaa ggccgagagc caggaaggtc caggggagca aaaggggag cagaggggga    31320 gctgagggtg ttggggtggt gggtagagag ccaagatagg gaggggacaa gagagggggag    31380 aatctcaagg aaaagcagga gcatgagact gagagaaggc ccctggaaca ctggcttgaa    31440
tgtggctgac attggcactg ccagtactca tcccaaacca gggagctcag ccagcgcccct    31500 ttctgcatgt ccgctcttc atcagacagc taggaacaag ttatacgaga tgatgtccaa    31560
```

```
gtccaataaa tgtctaagtc cttttccactg gatctggccc cagcctcctc tctgaaccat   31620
ctcctatcac tccaccctat ccctgctggc tccttctgct ccagccatac aggcttgctc   31680
ctgggctcag cttgtgcctg cctggggagc ctcgcgcttg ctgtttcctc cttgagaaat   31740
tcctgccctg gataactcct tcccccactt ccttcagatc tctgctccct tatcaggggg   31800 cttccctgg ctgccctatc tataacagcc ctgaccactc ttttcctctt ctcctgcttt   31860
ctttgtcttc ctgttcttat cactaagaca tcacacatgt cttagttggc ttgtttatat   31920
tctgtctcca cccatcttag tcagctactg ctgaaatgat gctgtgtaac aaaccacccc   31980
gatactcaga ggctccaaac aagtgctgat ctttctcatt tgtgagtctg tgtgtcagcc   32040
cgagcagggc agctccaggc tatggcttgg gtttgggtgg actccatgtc tctctccatt   32100
ctccttggac cagcagctcc ctggggcaca tgcttgtctt ggagaatggc aggaacttaa   32160
aagccaagcc aaacctcaca gcacggttaa gggtgatcat gacacaccgc taacattcta   32220
gtggccaaag aagtctcatg gccaagtgta atagcagtgg attgggcaag tttactctct   32280
tacacctgtt gtgaagggga gtgggagggg atgggggggt gaccgttttc acaacaacag   32340
tgcaaactat cccatctccc aatagaacat aaacaccttta aggttggaac tgggtctgta   32400
tccccagcac ttaaaatagt ttttggcata cagtaagggt gcaatagaca tttgttaaat   32460
aaatatacag actaaccaat tagcataata cagatgacaa aggtgtctct cttctgccag   32520
cttctgtgcc tgaaatgttg atgatctcct ccctatcttc ctaacatctc tcctgtcccc   32580
acctgtccat gcccagggtt tggctgctgt gacagaagtg tgagagcctc ctgtctccct   32640
tgggatccca gtaagagctt ccatgcctct ctccctgctc acctgggctc ccatccctgg   32700
ggaccttctg gaaacagctt ccagggctcc cagagcttac ttagccagat tctacatctg   32760
gctccagctg ttatcctaag cttggccttg ttttctgatc tgaccacagc ttcatcactc   32820
ctacctgact gtgggattct agcccccagt ggggtgggg accaagggtg acaattacct   32880
gggaccttga ctattgaaag gctaatcagg tttgattggg aaaaagagt tgctaaaaag   32940 gattgtattg gataattggt gagatttgaa catggatttt atattagtat tgtgttatta   33000
cattttctga tattagtcat tctttttttt tttttttttt gacggagttt gctctgtcac   33060
caggctggag tgcaatagtg tgatctcggc tcactgcaac ctctgccacc cgggttcaag   33120
cgattcccct gcttcggcct cctgagtagc tgggactaca ggcgggtgcc accacaccca   33180
gcttgttttt gtacttttag tagagacagg gtttcaacat gttggccagg atggtctcga   33240
tctcttgacc tcgtgatctg cccgcctcag cctcccaaag tgctgggatt acaggcatga   33300
gtcaccgctc ccggccgtta gtcattctta taggtatgta agaaaatgtc cttgaggtat   33360
ttagcaggga agttcatgat ctctgcagct tactcacaaa tggttaaaca gaatgagact   33420
aagaacagac tagtaagaaa agactgaaga atataattat taggccaggt gcagtgactc   33480
acacctgtaa atcccaacat tttgggaagc tgagatagga ggatcacttg aggccaggag   33540
tttgagacca gcctgggcaa catagtgaga ccccatctct acaaaaaaaa aaaaaagtaa   33600
aaattacgtg ggcacggtgg tatacgcctg tacttccagc ttcttgggag gctgaagtgg   33660
gatgatcaga ggacctcagg agtttgaggc tgcagtgagc tatgattgca gcactgcact   33720
ccagccaggg agacagactg aggcccggtc tctaaaaaaa aaggaatcta tgtgagtcta   33780
tatattcgtg caacttttct ataggattga aactctttaa aataagctta ataataaaaa   33840
caaaagctgg tgggtgagac ctttcatgta ctctccagga gagttaagcc ccccaacatt   33900
cctgtcccct tgtttactct caagcacccc ctcccccacc caaggaccag gtctttgttt   33960
```

```
actgagcatc tcagcgatga gctctcaccc cctgatttca tcaattataa atgtgctcgc   34020
tactcaccac acggcaattt gtgacggact gtggtttgtg gtgagagtag caccatccaa   34080
gttcaccgca gccgcgagta gagatgaggg ttggggccag acacagggct gtggggcgg    34140
caagggcacg caggcagccc tgccaccttc ctgtttgtca gccaagtgag gcttccgagg   34200
gcagcgggcg agcgggtcac tactcagggc cagctactgc ggccaggcca ggctagtcag   34260
gtctgtgcag ccagaactag aggctccgcc aggatgtgag gtctcccagc tcctgggaac   34320
tgaagcaaac actctgacta cccccttcttg aagtgcctta cggtgtatac atttgtttaa  34380
tctgcacaac aaacctagga gcagttattg ttactgtcct cattttgcag atgaggaaac   34440
tgaggcaaag agaaattaag taactccttc aaagtctggt aagtgacaga accagatttt   34500
accctcttac tcattgtcca tattgccgag taacttacat taatagatac tatgcatgtt   34560
tattttattt tttattttt tttagagatg gggtctcatt cttttttttt tttttttttg    34620
agacggagtc tcgctctgtc gcccaggctg gagtccagtg gggcgtgatc ttggctcact   34680
gcaagctccg cctccctggt tcactccatt ctcctgcctc agcctcccga gtagctggga   34740
ctacaggcac ctgccaccac gcccggctaa ttttttgtat atttagtaga gtcggggttt   34800
caccgcgtta ccagtatggt ctcgatctcc cgaactcgtg atccgcccac ctcggcctcc   34860
caaagtgctg ggattacagg cgtgagccac cgcgcccggt cctcattctt tcactcagac   34920
tggagtgccg tcgtgcaatc tcagctcact gcagcctcaa ctcggggctc aagcaatcct   34980
gccacctcag cctcccgagt agctgggacc acaggcagtg ccaccacacc caactaattt   35040
ttgcatttt tgtagagacc ggcttttgcc atgttgccca ggctggtctc gaactcctga    35100
gctcagacaa tccacttgcc tcggcctcca aaagtgctgg gattatagca ccacgcccag   35160
ccgatactat gcatgtttaa ctgacaccta atgattagg agcaacaatt tcttggctgc    35220
cttattcacc ttcatgaccc ccaacattga aaatgtcttt tcccatgtga aagcatttgt   35280
gggctcctac tgccaatcta taaagtagaa atccttctgt ggtacaaagc cctctttctt   35340
atctaatttc ccatttcccg ttcccccttc ccccttctgc taagagctct tccctaccca   35400
cattgtaagt agggccgggg agctaactcc accttgcgta ctccaaatca accacatgac   35460
ccaggcctga ccaatcaggg ctccaaatcc tctagctata gtgattggtt tagggaggga   35520
catgtgaccc gcctgagcca atgaggatct gttctgggac tcctgtttga actcttggga   35580
aaataaactc cttatgttgg gtggctgagg ggatgaatgt gagctgggag ctgcaagcag   35640
gcatcatgct attcccttca gctttcaagt agtgttttca ctgctgttaa caattccaaa   35700
tcttaagtgt tccttgcatc ttcctctcgc caaaaatatt acagtactgg agggcttaca   35760
tggtgtctca aatgtctgga gtttaaatct gccttgcagc ttccatggcc acagtgagtg   35820
tctgagtcct ggccgctttc tgctgatccc ggggagagtt tagcctgcct gcccttcctc   35880
cctggttcgt tctcatgtac tcagatccct gcctcactct tctctcacac agacaacaaa   35940
agagagtcag attgtggtct taagtgcaca ggactctgaa gttaggacca gaagaccttg   36000
gttagagtct aaaccttgtc agttaccaaa tatcattagg cacattagtt aatctctctg   36060
aggcttattt ccccatcagt aaagtgggta ctgctgaaga tgtagtcttt agaagtgttc   36120
tctagattgt aagcccgtg cttcctggtt attgactaaa cagggataaa aatgagtttc    36180
tcctcacctg ggtgtcattg agtttctggt cattgtgaga tgggtgatga agccaagggc   36240
atcaaacatc ccaacgaggc tgttttctgc atctccaggg ctatcccagc gttaatcaca   36300
tatggacctt taatcagagt ttgcagaata agtgagaatt gtgttagagt atgaatgtag   36360
```

```
atattatctt gttttagtca ttgttactct aggggaccat tcttactaca ggaatattgc   36420
acaaaaccca gaaatttatt gactttctcc taaccaaggc ctaaagagct ggtgttagac   36480
ataggccaag gccagccaga ggcccaaagc ctgtttccca gggtaggact gccctggcct   36540 cccctcttt ctccccaggc tccaccccag agagctgaag accaggctgg gtacggcact    36600
gctgagaaac tgaggaaaag gccactggcc tcctctctca ctgcaggctg cccacccggg   36660
agggggaaag cttgtcacta aatcaggttc agttttggtc actgtcttgg actggatatt   36720
ctagcatcag aactgagatg tttcttgtga cttaaagtaa cttcaggact ctattctacc   36780
taggattggg cagaaaagtt atgggcctgc gggagttcca attcagaaac agggagatt    36840 acttgcacta agaaagtct aaaggaaggt aggagacaaa aataaagttg tgtattgatg    36900
atcctaggag ttatgcttgt ttgacatacc agttatacct gctgtcacgg tagttatgca   36960
ttaggggacc caggtgtctg aagttatatc agaagactt ctgagggtgc accgggggt     37020 cccttggcta aaagtgtgat ttaaacccta agagcctgcc cagactatca gtcccagttt   37080
ctacgtccac tgtccctgaa tctcgctgct tcttccttag gctgctggga gtctgaaccc   37140 tccccgcca acaccctcc cccatgcctc agtcgtggga agggggggcc cttgagcagt     37200
agggccaagc cctgttcagc ctgggaccaa gttcccatca acaaggtggt ctgggcagtg   37260
gccagccaga aagcagtaat tactgtcgag gtgcagggac cccaggtagg gcccccacct   37320
cccacctctg tgtgggcagt gaatgggcct gcccctgggt aaggctgtgt cagcaggcgc   37380
ctgcccaccc cttgctgggt tcccaggccc ctagagccct ctcgtaatag gagccatttg   37440
cgctgtaacc agtgggtgac cagattttta atcttggaga cccccttggat cccaggcggg   37500 aagtgggatt tgtcaaatgg ggagaggcgg ggctgtctgg gaatgccaga cggggttgtg   37560
ctggggaaat atgtctcctt tccatacagc cccctttccca tacctccagc ctccctctac   37620
cccgcaagtc agctctgtag ctcctaggag gtatctccaa catgcttagc tgttgaaagt   37680
aaatgaatgc cggaagttga aatctgaatg gcttgttttg cactaactca ggtgcatgcc   37740 aaatagggggt gtctctttgc ttgatcctaa tccttcctcc tctgaaatcc tttctgacct   37800
gctgcctatc agcaattgcc ctgcaaagac cctctagctg gccgcgggag aagctgtgtt   37860
cttggctatc aggagtgaga acactggacc caagcttgcc tattctctgc cacaactcac   37920
tgtgtgatct tggacaagtc acttcctttc tttcagcctc agtttcagga gacttggcac   37980
ttgctgagtg ccaatgtgtg ccatgttctt gacaagtatg gtcccacaca accttgccaa   38040
tgaccctgtg acctgtgtct tcttgttccc agtttacagg agagaagatg cagcctggga   38100
gagatgcagc aggtgtctga ggccacacag caagtcaccc agggccagga tctgaagctg   38160
ggtctctcca gctccactgc ctgggcactt tctcctccac agcgaccttc aggtcatcat   38220
gaggagcctt tcggactaaa gctagagagc tgggattcca acagttcagc aacccatgac   38280
ttctccatgg cagctgctgc ctgaccacct agtgcctttc cactaagatt gttccttccc   38340
tctcctgaag attatcctcc tgcccctctc tcccaaacat ctgcggtgtg cacctgctgc   38400
ccaaagttga acttttttttt gttagagaca gggcctcact gtgtcatcca ggctggagtg   38460
cagtggcgtg atcatagctc actgcagcct ccaactcctg ggctcaagtg accctctcac   38520
ctcagcttcc tgagtagctg ggactacagg catgcaccac cacgcctggc taattttttaa   38580 atttttttgca gagacagggt ctagctatgt tgcccaccct ggtcttgaac tcctgggctc   38640
aagcaatctg tctgccttgg tctcccagct cgctgggatt acaggcatga atcaccatgc   38700
ccggtcctcc aaagttgaac ttttgagact cagtttcctt cttggtaaat tcaggctcct   38760
```

```
aggtgctacc tcctcagaga catcctcctt gaccacatca catgacctct cgcagaggcc    38820
agattcttta atgtattcat ttgtctatta tcatgtttcc ccagtagaag ttgcacaaac    38880
ggcaggggct tcatctgttt tgtttgccgt tatgtcctta gcacctaaaa ttgtgcctgg    38940
cacatatagt actcagtatg tatttgctgg gtcaatgagt gagtgaattt atactaataa    39000
cagcagctac catttctaga gtgtttacca tatattgggc actgtgtcag tcttcccaac    39060
aacccacaga cgaagatcaa ttattacacc cattgtacag atcaggaaac tgagtcaggt    39120
taagaaactt gccctaaatc ctacagtctc acttagaact tctgactgca gtgctcatca    39180
gaatgcattg tcaacccaaa ggtcatttcc agctcaggtg gcttctatca aaagagctca    39240
tcctggcctt tccaagagcc agacctccga catcggtgga gccctgtgca tagctggcct    39300
ctcctgggcg tcttgtccca agtacagaga cctggatcct ttcccactca tgtgcaacag    39360
cccaaaatta aaacaaaag ccatattaaa aaacaaaacc aactttctgc cttaaaatat    39420
tgtgagccag ggggcaatta gcaattatgc tgtattttat tatgagaaga tagaattcta    39480
attggactga tttgaattcc acacacctcc acagattgtt ttgggaatta aggtatcagt    39540
tgtatcggta attatggttt accattcaat taccccccca cagaaaactg ttaaattgtc    39600
tgtgacgggg cttaaaattta gctcagacct atgtcctatg aagactgcgc gagtcaatac    39660
aagccatccg gaaaccaccg ggtgccctgt gccaggcggt aattaggggt tgaggtttcc    39720
aaagttttac ctgagacagc agggacaagt gcctgggctg ggcgtgctca cgtgggggg    39780
cttggatgct cccccagcac agtgctcttg gctcctgccc tgcgttgctg gtgcaatagc    39840
tgatcatctg gaagacaatg tggtttcagc cgcaagtgac attttggcga ggtgcaccag    39900
catagaagcc ctgagacagc gagggaccat gtaaaactca cggacattgt aattggacac    39960
atctgggatt gaattcccac tcttccactt agggagtgaa cttgagaggg ccacttaata    40020
tctttgagcc tctgtttccc cacctgtcaa atgggtacac ctcctgcctc acacacgggt    40080
tattgtgaag atggatggag aataataatg gtgcctggcc caaattgcat ttttttctct    40140
tttttagta ctcactacat gccagatact ttacaaacat ctctaaacct cctaagccct    40200
atagggcagg cactgtggtt attctctgtt ttatggatgg gaaaactgag tcccagagag    40260
gttaaataac atgccgaaag tcccatgact atgaaatggg gcagctggga tccaacccca    40320
ggtgacctag ggccaaaccc taagcatgaa gctgccctgc tgggtgcctt ctgtacctgt    40380
ccctctaagt ggaagtgcct agaaatgacc cagccaaaag cagcagactg tattttatca    40440
tttcaacaat tctctctgtc cataaaaagt tctatgcagc ttggccagtt cctttttcct    40500
gaatacaaaa ctgagaatgg taacagggaa ctgacttttt aatgtcatgg tgcaaaggag    40560
ctagctctgc catgacctcc ttgaagtgac ctggtagagt gagggtaaga caagccacac    40620
tccctaggct atggaggcca ctctccatgg agatagggga ataggggaatc ctgcaaaata    40680
cagtctctgg ggatgggaag gatcaggaa ggggccaggt gcagtagctc atgcctgtaa    40740
tctcagcatt tcgggaggct gaggtgggag gatcgcttga gcccaggagt ttgagaccag    40800
cagtttgaga ccagcctgag caacatatca agaccctgtc tttacaaaaa attaacaaaa    40860
aggccaggcg tgatggctca cacctgtaac cccagtactt tgagaggccg aggtgggcgg    40920
atcacctgag gtcgggagtt tgagaccagc ctggccaacg tggtgaaact ccgtctctac    40980
taaaaataca aaaattagcc aggtgtggtg gctgtaatac cagctactcg ggaggctgag    41040
gcaggagaat cacttgaatc caggaggcag aggttgcagt gagcccagat catgccactg    41100
cactccagcc tgggagacag agtgagactc cgtctcaaaa aaaaaaaaa acaattaaca    41160
```

```
aattagatgg gtgtggtggt gcacagctgt agtcccagct actcaggagg ctgaggtgaa    41220
gggatcactt gatccaggtg ttcgaggcta tagtaagctg tgatcacccc actgcactcc    41280
agcctgggtg acagagtgag atcttgtctc aaaaaaaaaa aattttttt  tttaaaggat    41340 cagggtaggt acatggactc ctcctattcc ttctggcacc atcagtggtt gaacacacaa    41400
actttggttc aaatcctgcc tcttccaatt tgctagctgt gtgaccttga aaaagttact    41460
taacccctct tatccttagt ttcctcatct tcagaataaa aatagtgctt gcctgatggg    41520
ggagatgatg gatgtaaagg gcctcataga gggcttggca tttaccaagt gtttgagaaa    41580
tattggctgt ttttattcaa ggcctgctca ttgctagcat gagctacctg caacagccac    41640
ctctaggcct cttttgctcc ctatagtcca gccacaccaa gaaaccatga tggcctgaat    41700
cctctctgac tttgtcaggc ctccgtgcct ttatacatgc tgttccttct gcctagaagg    41760
cctttctctt ttttcaacct ccttgagtcc attttagtcc ctgccagatg gtcacttctc    41820
tgtgatgctg ccctaactcc ttggcagcca tgctgctccc ttgaccattc actagcccct    41880
ttaattcagc cccagccaca gtgaggatta aatgggatga tgtctgagaa agcccatggg    41940
caagaacctg gcatggagtg gtgccccata aatgatgaat ggagctgggg ttgctttctc    42000
agccagctgc ctggcagggg cctggcttcc tcatcttcac acgtcagtgc ctagagtaac    42060
acctggcaca cagtgaacac aatctcagta actgttagac atttgtcttt tggggagctg    42120
ctcagcctcc cacattgggg tgtgggtttt ttgttttgtt ttgttttgtt ttttgagacg    42180
gagtttcatt cttgttgccc aggctggagt gcaatggtgc gatcttggct cactgcagcc    42240
tccgctgcct gggttcaagt gattctccta cctcagcctc ccgagtagta gctgggatta    42300
caggcacgtg ccaccatgcc tggctaatgt tttgtatttt tagtagagac aggatttcac    42360
catgttggtc aggctggtct tgaactcctg acctcaggtg atccaccgc  cttggcctcc    42420 caaagtgctg agattatagg cgtgagccac cacgcccggc ctaggggtgt ggggtctttt    42480
accgactagg cctggtgggg aagtcaggg  accccaccac aaaagttgga gaggccacat    42540
cctcccacct ccatctgggg ttagacatgt gacccaggct tggccaatcg gatgttcctc    42600
catcttgccc agaattcaca ctcagcagtg gtcttcacga ggggtggtag tggtggccag    42660
taggagcagg gctgggcagc ctccctaacc cacgttcatg agacttgaag ctggctggtt    42720
tcctgtcccc tggcctccct tgcccattcc catcctggtg ctccctccct atggactcct    42780
tttgctcata aatatccctc caattaattg ctttgctgct tcttagctag tgttgtttct    42840
gtcacttgca accaagagcc tattcaggtg caggaaggga tgaatgaaca atggaaatgg    42900
atcaacacat gtttctgagc atgtgctgac aggcaggccc tgggcggagt accacggtgt    42960
tcaaatgatg tgtaagatgt gggcagtgcc ccggggggtc tatggggaga cagaccatgc    43020
atgacatcat aaacaagacc acattataaa gtggggttta gttggacctt gcagacaccc    43080
agagaagacg actttgagcc ctcattggat ggtgccatcg caaagtacaa aacgaattgg    43140
gttgtaggaa ctggaggcac tgggacaata ttccagatta gggattgagc tgaagggtt    43200 ggaaatggct gagtagggtg gtggaaaggg atgcctgcta gtaggcaatt gtcttagtct    43260
gttttgtgct gctgtaatgg attaccacag actgggtaat ttataacaaa cagaaattta    43320
tttggctcat ggttctgaag gatgggaaat ccaaaatcaa ggagccggca tctggtgagg    43380
gccttcttgt tgcatcataa catgccagag ggtgtcacat ggtggaaggg caaagagagg    43440
gagaaaggga aagagaggga gcaggaaagg gcaaacccac tcccatgata ataagctcac    43500
tcatatcatg agtcattcat ccatcgtgag ggcagggtcc acctcccaat accatcacaa    43560
```

```
tggcaactaa acctcaacat gattttggga gaggacaaac attcaaacca tggcagcagc   43620
gtttgtggga aacacgcgcc aaagcaagaa aagaccaacc taagagtgag tgacttggct   43680
cctcattcta cattcatttt catccaatgg ggcccaaggg catgtaccca ttacccatct   43740
gggcagttcc cttgaatgtg ggcttctgtt tgcccgtgga ggtgaggaac ttcaaggaag   43800
aaaccatgaa agacctcttg aggctgaggg ctggcaccag caccaagatc tccaggcagc   43860
tggaacagtg atggctcctc cgtcctcgca ggcggggcac ccaacagggt gtgaccgtca   43920
cctgagggga gacagccaga ggcacaggcc tgatcctggg actgaggttg gcggtttggg   43980
tggagaggtg attctgagtg tgacaccctc cagtgataaa gtgggggggct tcccagcagc   44040 ccctggggaa acaggctgca tctctggaga caggagatat gtggaggcct gaggggcagt   44100
ggaaagccct gtgtgtctgg gtcaggtctc tccttggcag gtaatggttt gtcccagtag   44160
ttttcagact ccccatcctg ccctgtcctt ctcctgtctg atgctcagac ctgtcactcc   44220
cagctcagcc cccaccttac tgtctacccc tcagagtccc tcccaccaag ggcaccttct   44280
gtcccacatc tccatggtgc agtcatggga ggagaacttg ggagcataag aaactccacc   44340
aagttggggc caggcatggt ggctcacgcc tgtaatccca gcactttggg aggccgaggc   44400
tggtgaatca caaggtcagg agtttgagac cagcctgacc aacataatga aatcccgtct   44460
ctattaaaaa tgcaaaaaat tagccgggca tggtggcagg tgcctgtaat cccagctact   44520
cacgaggctg aggcaggaga atcacttgaa ccgggaggca gaggatgcag tgagccaaga   44580
tcgcgccatt gcactccagc ctgggtggca gtgaaagact tggtctcaaa aaaaaaaaa   44640 aagaaagaaa gaaaaaaaaa gaaactccac caagggcttt tgggtcctag ggacagcaat   44700
gatgtggctg gtccagccag aacctcattt tgtcagtaaa gttgggaccc atattcccta   44760
agagatttgt cccaagaaca catgggttgc tacagcggag gagaaatcaa gtctgttttc   44820
cctctggtga attgtcccct gaacgtgctt tcttcctaca gtgttgccag gaaagtaaaa   44880
aaaaaaaaaa aaaaaaaaaa aaagtccacg atgtcagctg gggtgatacc aaaacaattg   44940
tgggaggaac aacatccgca aattgaatag tgtgaggagt gtggacagaa gatgttttgt   45000 cttttggcctc atctcccaga cttgatcttt gtaaatacag aagtttccac cagagccgaa   45060
cctggcaatg acttgaggag cagctgcaag gaagacagcc tctcccaggg tatcacctgg   45120
gggcacaccc cagcttcccc tcctgagcct catcgagggg ttagtgctac ctctcggaa   45180 aacataaaga tgacaagaag ccaaaggtgc caatagttcc catttagtat aaaagctggc   45240
tcagcaaatc atgctatttc agggcctagg gtgggccagt tcccaggcag ccctggcagg   45300
aaggactctg agaggcggac agtaaggtag gggcttggga gtgataggtc taaacatctg   45360
atggaagcaa aagggaggac aagggaggga gtcaaaaaat ccgggaagcc tgtccttcca   45420
gaaagtaccg acaccagggt gaggtggatc ccagcacccg cacctctgaa tggccttttcc   45480 cctgcacccc tatcccgccc ccactcggag ctaccccaag cacctgttcc tctgggcccc   45540
aaggtgacgc cctttgtgtg tgtataggaa aggacggtgt acacatttgg ttagttcctt   45600
cttttacacc ataaattatc agagacaacc cttttggaaa gcaatttggc aataatatca   45660
agtgacataa agatgttcat agcctttggc ccaataatct tcctcctggg aattaatcct   45720
aagaaaataa ttcacaagga agaaagaacc attttgtatc tacaaagaca tttattgggg   45780
tgttatttat gatagggaaa aactggagac accctcccca gccaacatag agggatggtc   45840
ctataaatta tgatacatcc atccaatgaa atgttaccct gccagtaaaa atggtaaatt   45900
gaaaattgtg tagcaacaag aaagagtgtt cagaaaataa aagcaagtga aaaaaggagc   45960
```

| | |
|---|---|
| acaggattgt ctatatgctg tgatcaatgg caatgctgac aaatccatgt atgtgtagat | 46020 |
| agttgtagtg ttacctgtaa ggcacgataa ggcggatgta actgtgcttc aaatgttctt | 46080 |
| ttccatagct gtggagtcct tctagtatga aatcatttt gtaaaatcgc aatttgtcac | 46140 |
| caggggtttt gactttcctt attgcctcgt gggaggtggc agaggcagca catctcagac | 46200 |
| cgagcctcgg ttcctccccc tacctcccac cgctgcgctt gaagaaagat gctgcagcct | 46260 |
| ccccagtccc catgccagcg ctcccacttt tctctgagct ttcggtggca gacagcgcct | 46320 |
| tgggcacttt ttcatgctca taattcgaat tacctgttta agtcggtcaa atgaaaaaat | 46380 |
| accagctccg cccccacgcg ggctggccgg ggcgcctgga gcgccagggc ggctgcagcg | 46440 |
| cgctctccgc ggccgtcggc cctgagctca tttcctgggg cgcgcgcgcc gggctatttc | 46500 |
| agcctggcgc tgtgcaaaca ggacaattta ctgcggccaa aagggaccca aattacaatc | 46560 |
| gtatcacaga caaatatccg ccacgccagg tctccagggg ccaggagggg cctctctccc | 46620 |
| ggcgcggggg gcgggcgcgg ggtcaggcag gtccgcgggg ctcggctcgg cctcgccgtg | 46680 |
| ccctgatcgg cgtttgccac cgagctgtgc ctgctctctg caacaggaag gggcccagct | 46740 |
| cccccgggcg accgttccta tctgagttct cgttcctatc tgggttttcg tgcagaaaaa | 46800 |
| cttcatctct tcccagggat tttcccctga tttagggtcc ccttttattt ggtttctttt | 46860 |
| cagcacttgg gatgaaaaca tccctccatc cagccactcc agggctcaaa gtcatatctc | 46920 |
| ctcgttcaga aacctcagtg cctgtccacc actcttccgg aaaagtcgga atccttagtg | 46980 |
| tgatggtcaa agaccgctct tagtccagtc cacctgtcca gggccagccc ctgtacccag | 47040 |
| atgctccaac cacggagagc acatcagact ttcacaattt tatccttgac aattgccttt | 47100 |
| tcatcctgcc taaatgttcc cttgtttctt tctgcctagt gagctcttat tccttcttta | 47160 |
| agacccagat acacatcacc tcttccatga agccttccca gacttcccct ttccctgctt | 47220 |
| gacatctgcc ttccaagcag agtcagcccc ttttccttcc tagcaccgtg cagaggtaga | 47280 |
| tggtacttct cacatcctgt aattaattgc ttgcatgcct gtggtacacc gtaccattgc | 47340 |
| tcacaaatat ttcctcttcc tctctggaga aggattacac ttccttgatc cattggcctc | 47400 |
| actcaggctt cgccacatga ctggtgctgg ccagtgaagt gggacatgtg agttactggg | 47460 |
| gagcagaaac tttcaaagcc aagcatggct caccttgttc tctcttccct ctgttacaag | 47520 |
| gatggcagtg cccagccag aaaccacact gccagcctgg cataggagtg gagcagggca | 47580 |
| cacataagtg tgagagaaat gaacttcacc tcagtgctcg aggcccctgg gaccatggac | 47640 |
| tcatttgtta ctgcagcata aactagctgg tcttgacttc agcttctgcc tctcttccct | 47700 |
| ggctttgcct tcacaaaatc aagagtctga tcttactcat attatagagc tggtcttcaa | 47760 |
| ccatgttctt ttttttttt tccttttttt tttttgaga tggagtttcg ctcatgtagt | 47820 |
| ccaggatgga gtgcaatggt gcgatctggg ctcactgcaa tctctgcctc cctggttcaa | 47880 |
| gcgattctcc tgcctcagcc tcccaaatgg ctgggattac aggtgcttgc caccacgcct | 47940 |
| agctaatttt tgtattttta gaagagatag gatttcacca tgttggccag gctatctcaa | 48000 |
| actcctgacc tcaggagatc tgcccgcttc ggcctcccaa agtgctggca ttacaggcat | 48060 |
| gagccaccat gcccagcccc atgttcttcg aatggccaag aatatcagta ggtaaggttt | 48120 |
| gttgagcatg gattgtgtgc caggtgctgt gctatgcctt tggcaagcgt tatcccatta | 48180 |
| catcctttaa cagcactctc tggtgggtac tgctcttata caagatttac aaaagagaaa | 48240 |
| agagactcag aggaatgtag gggctcacgt gagattgtaa agtagtgaga agtggagctg | 48300 |
| gtccttcagc tcaaatccct ctgatgccaa agaactcaaa ctctgcagtt ccatcatgtg | 48360 |

```
catcctcact ctctcacttc ctgcagagga tctgtggagg ttgtaactat tgttttcacc    48420
tgtctcttcc actgggctct gagctgcccg aagacagatc ttttttttt ttttgagaca    48480 gaattttgct cttgttgccc aggctggagt gcaatggcac gatcttggct caccacagcc   48540
tctgcctctt gggttcaagc gattctcctg cctcagcctc ccgagtaact gggattacag   48600
gcatgcgcca ccatgcctgg ctacttttgt attttagta gagacggggt ttctctgtgt    48660
tggtcaggct ggtcttgaac tcccgacctt aggtgatctg tctgtctcgg cctcccaaag   48720
tgctgggatt ataggcgtga gccaccacgc ccggccccga agacagatct taatcatctg   48780
atttcccatc cattaattca gtcttttcacc aaggatgtat tgagtgccaa ttatatgcca   48840
ggcatcatct gatgtgttgg ggacagagaa ataaaacaga taaaaatccc tgctgttaat   48900
tctagcctat ggtgacaaga agcagatccg tggctgcctg gggtgagtgt ggggtaggaa   48960
atgggagaaa tggggatgac tgcaacttttg ggggtagtgg aaaatgttca gtatcgtggt   49020
agtggtggtg gctgtacagg tatatatatc cgcatacatc ccacagttca gaattataca    49080
ctttaaatgg taaatggata cagtttatta tatgtaaatg atccctcaat taagttgatt    49140
tagaggaacc tggccgggcg tggtggctca cacctagtat tctcagcact tgggaggcc    49200 gaggtgggcg gatcatgagg tcaggagata gagaccatcc tagctaacat ggtgaaaacc    49260
catctctact aaaacacga aaacaaaaaa ttagccgggt gtggtggtgg gcgcctgtag    49320
tcccagctac tcgggacact gaacctggga ggcggagctg gcagtgagct gagatcgcac   49380
cacttcactc cagcctgggc aacagagcaa gactctgcct tgaaaaaaaa aaaaaaaaa    49440 gaacccttgc tcttatggag aagcattcta ctggggaaaa cagacaataa acacatagat   49500
aaataaaaca tatgtcagaa agggggtaagt gatgctcaga aaaataggac aagggatcag   49560
aagtgctagg cgttgcaatt taaaataatg gggtctggaa agccaccctg agaagggcca   49620
atggagctat gcccagcctg tggtatcctt cctcaggcag gggactgtac ccccagctta   49680
caagcctttt cgaggcacct tcagggtttg agcccaaaat gcactgcaca ttaagtgtta   49740
ttgatgggct tgtggaaatc tgctctccgt caggctctga tgaaacttttt ccaacaggag   49800 actgaactca gtactgggca tggccccctg cacatagtaa gtccacagca aatgtgtgtg   49860
gggtgaatac tgtcttcttt atcctcccctt tttctactcc agtccaggta gacggtgtat   49920
ctacccaccc aattttgctg tttctggtac cctcagtggg tcttgcctgc tcttcctcct   49980
tgaaatcatt actcagaggt ctccgtgtca gctccagaca gatgggcctg gtgctccttt    50040
atctcaatac aattcccccg ctcccaggct ccaggggaaa tcctgagcta actttggtct   50100
ttcctaaact ccacacttcc ctttgggcac ctctttcccc attgcggggc tccctttcag    50160
aatttgctgc tttatttatt tatttattttt tgtcagaggt gcattaatga tgctttattt   50220
aaaaacaaaa aacttggcca ggcgcggtgg cttatgcctg taatcccagc actttgggag    50280
gctgaggtgg gcggatcaca aggtcaggag atcaagacca tccagaccaa catggtgaaa   50340
cccagtctgt actaaaaata caaaaaaaaa aaaaaaaaa aatcagccgg gcgtggcaca    50400
tgcctgtaat tccagctact caggaggctg aggcaggaga atcacttgaa cccgggaggc   50460
agaggttgca gtgagccgag attgggccac tgcactccag cctgggtgac agagcgagac   50520
tccatctcaa acaaaaaaac accacaaata aataaaaaat aaaacaaaa aaccaaaaac    50580 agtccattcc atgtcgtgtt gaaactgatc agtgtaagtt aaatggtggt ttttaggctg    50640
gacccatgat ttaagctgta cccatccagc tcaaactgaa aaaaaaaaa atcatttgaa     50700 tgttaaagca atcgttcaga gtcttcaaga agaaaccagg caggaaaatg ccaataatga   50760
```

-continued

```
tgactggcaa aatcaaaatc taaaacaaat aaactgttta tcaagctgcc gacagaaaaa    50820
gaaatcttgc atggagacta caagtctgga ttttctggga tgaaattgta caggaatctc    50880
agtctacagt ttcctcaatc gctgtggaga tggagctgtc actgaatctg acagagccct    50940
gcactcccca gtccgccgac cctttctgta atccagtctt cactgtagcc tgaggaacta    51000
tttcaacctg ctcctttttt atcttcttct ttggcacaac ctcagtggac ttctctgatt    51060
cagaacaagt tctaattgat cttctctgtt gcttcttttc tactgagcct gtagaaccag    51120
atgttgcttc aagagatgat atattctgca ttggcttttc atttctctgg tttggtttag    51180
aaattataag cctgtcttgc ccctgacac ttatttctgt tttgttacca attccctttg     51240
ttgaataaac aaattaattt cccatcctct gtagcattct gaagagcaaa cacttcttca    51300
attttcacag ctggagacat gttacacttc tgcaaatcca ggctcccttt gtgcattgta    51360
atggaagctg gtaggatttc cttgctgcca cagttttcca ggctattta acaggaggtg      51420 gctcttcctc gtccgcgctt gtgtgctgcc tcgggctgtg tctccaaatg tcagtacttg    51480
agagtgagga ggccacctcc cctgcattga tctgttctgg ctgagtttaa agcacagatc    51540
ttggtcatca ggttttttta acttcggctt tggagacaac attctttttt tttttttttt    51600
tagatggagt ctcgctctgt cgcccaggct ggaatgcagt ggtgcgatct ccggttcatg    51660
ccattctcct gcctcagcct cccgagtacc tgggattaca ggcgcccacc accatgccc    51719

<210> SEQ ID NO 3
<211> LENGTH: 492
<212> TYPE: DNA
<213> ORGANISM: Homo sapiens

<400> SEQUENCE: 3
ggtttcaact agttctggtg catagcagcc cccaaagttt tagcagcgtg gttagtggag        60
agctgtggct tttgcctcca tctaaatttt tctttgagca aattacctct ctcctgacag       120
ccctgttggg ggtgtcagtt gtggggttct ggtacctccc atcccggccc cagctagagc       180
aggcaggccc acaggaattt gaatctggag ggagttatca gtggtggagc gtagaggctg       240
caggaatctt catataagtg gagtcatata atatgtggtc ttttggtctg gcttctttac       300
ttagcatgct ttcaaggttc atccatgtcg tgggatatat tagtgcttca tttcacttct       360
gatggcaggg tcctgaatta agtcctgccc tgaggatcac actgttacat ctaggccttg       420
taggattcct gaaaattgca tcccatctgc cctgctctaa aatctacaca gcctttgcca       480
tatccattta tc                                                           492

<210> SEQ ID NO 4
<211> LENGTH: 557
<212> TYPE: DNA
<213> ORGANISM: Homo sapiens

<400> SEQUENCE: 4
ctagggctta gaagtttcct taacaccaac tgaggagtcc cagggtggga gctgagctca        60
cacgaagctc tacttcgcgt gtcctgaagc tttgacagtt gggcctcttt ctggcttttg       120
catcctctgc tcatactaag gccagcagag ctacaggttg gaccatggtc tggccgggag       180
ctccagcttc ctcttttcct ctcagtagtc atcgggccag ctgcccatac ctggtgccca       240
ggtatgagaa gagacctttg gctttcacca ggttcttgag agggtcaggg acctccaaaa       300
ggataaatgc cattggtcag atagtcactg tctacctccc tcccatccat ttcctgcctt       360 caaccctgt tcttgggaca aggccttcgc tggcattcaa tggcgggtcc ctgaggaagg        420
```

```
cccagcctt gccgaacatc cttcaaggga gacttcagcc cctggccctg cagtgagtgt      480
gttgttagca gcagagggc tgagtgaggc agtgggatgg ggcttttctt ttttgttctg      540
gttgcaaatt ataaacc                                                     557
```

<210> SEQ ID NO 5
<211> LENGTH: 819
<212> TYPE: DNA
<213> ORGANISM: Homo sapiens

<400> SEQUENCE: 5

```
gccttcagtt tgtcccgttc taaccgcccg gccgtctcaa tgcgatcaca ggagggacac       60
ggagatcgag gagggccaca gccggaccag gccaggcgtg ctgcggcagg aggaaggctc      120
cggaggtggg gtgggaaggg gaggccgaga gacgggtgtc gccgcgcccc cgctgccgcc      180
agagaggagc ctacggctgg cagcctggcc tgggcagcag ggtcctcggc gctcggctgg      240
gaaatcgcac gtctctccgc ggtgacctgt gcacagcccc tgggcctccg cctccgtgct      300
ggcagcctcc gcctcagcgc acaaagcccc gtcacccga ctctcggagc gccgccgccg       360
ccaaatcctc agcccctccc tcattggccg cggcgtctgc cgggaagtgc agtcccgggt      420
ttggggcgat ggagcccagg aggaagcggc gagtcagcgc ggcggagagg gcggagggga      480 cggaggggc ggaaggggac gaaccacgaa cgcccgcggc cgcgaagggt ctggacgaca       540 aggagagac tagcgagagg gcttgttgct tttttttttt tttttttttt tttttttttt      600
gagacggagt ctcgctctgt cacccaggct ggagtgcaat ggcgcgatct cggctcgctg      660
caacctccgc ctcccgggtt caagcgattc tcctgcctca gcctccgagg agctgggatt      720 acggggcgc gcctccacgc ccagctaatt ctttgtactt ttagtagaga tgaggtttca      780
ccatgttggc caggctggta tcgaactcct gacctcgcg                             819
```

<210> SEQ ID NO 6
<211> LENGTH: 581
<212> TYPE: DNA
<213> ORGANISM: Homo sapiens

<400> SEQUENCE: 6

```
ccctgccatt ctggatagtt ttggttattt ttagtttaac ttcaggtgag ccactcttct       60
ttggaatcac agtttgtggt accgaagtgg tgctgtgga ggggaagggt tttctagaat       120
ttaatgtggt cttctgttta gaatttctga atggtaatag tcagtggggc taaagtttct      180
agctgcgcca aagtcattgg ctgacccatt aggatattga ttatgcgact ggtatttggt      240
ttgaatttca tacatgctga ttgatggcag gtagccattt gtgagtggag gaagatctgt      300
tgtaggtgag tattgaaagc tttgctgcaa ggtagcttcg tatggtgtct ggccaccatc      360
ttcagcaatg tcacttttgt tatcaaaggc atcctcctga cggatgctgg cggagtcagt      420
gagttgaggt ggttgttgaa ctgtgtttcc cgtgatccct tgcatgaaag agaaagagaa      480
atccattgtt ctgctccagc attcttaact ttcccttcct ctcatcgggc cttcagtttg      540
tcccgttcta accgcccggc cgtctcaatg cgatcacagg a                          581
```

<210> SEQ ID NO 7
<211> LENGTH: 602
<212> TYPE: DNA
<213> ORGANISM: Homo sapiens

<400> SEQUENCE: 7

```
attccctaag agatttgtcc caagaacaca tgggttgcta cagcggagga gaaatcaagt       60
```

```
ctgttttccc tctggtgaat tgtccoctga acgtgctttc ttcctacagt gttgccagga    120
aagtaaaaaa aaaaaaaaaa aaaaaaaaaa agtccacgat gtcagctggg gtgataccaa    180
aacaattgtg ggaggaacaa catccgcaaa ttgaatagtg tgaggagtgt ggacagaaga    240
tgttttgtct ttggcctcat ctcccagact tgatctttgt aaatacagaa gtttccacca    300
gagccgaacc tggcaatgac ttgaggagca gctgcaagga agacagcctc tcccagggta    360
tcacctgggg gcacaccoca gcttcccctc ctgagcctca tcgaggggtt agtgctacct    420
ctcgggaaaa cataaagatg acaagaagcc aaggtgcca atagttccca tttagtataa     480
aagctggctc agcaaatcat gctatttcag ggcctagggt gggccagttc ccaggcagcc    540
ctggcaggaa ggactctgag aggcggacag taaggtaggg gcttgggagt gataggtcta    600
aa                                                                   602

<210> SEQ ID NO 8
<211> LENGTH: 572
<212> TYPE: DNA
<213> ORGANISM: Homo sapiens

<400> SEQUENCE: 8
gagaggacaa acattcaaac catggcagca gcgtttgtgg gaaacacgcg ccaaagcaag     60
aaaagaccaa cctaagagtg agtgacttgg ctcctcattc tacattcatt ttcatccaat    120
ggggcccaag ggcatgtacc cattacccat ctgggcagtt cccttgaatg tgggcttctg    180
tttgcccgtg gaggtgagga acttcaagga agaaaccatg aaagacctct tgaggctgag    240
ggctggcacc agcaccaaga tctccaggca gctggaacag tgatggctcc tccgtcctcg    300
caggcggggc acccaacagg gtgtgaccgt cacctgaggg gagacagcca gaggcacagg    360
cctgatcctg ggactgaggt tggcggtttg ggtggagagg tgattctgag tgtgacaccc    420
tccagtgata aagtgggggg cttcccagca gcccctgggg aaacaggctg catctctgga    480
gacaggagat atgtggaggc ctgaggggca gtggaaagcc ctgtgtgtct gggtcaggtc    540
tctccttggc aggtaatggt ttgtcccagt ag                                  572

<210> SEQ ID NO 9
<211> LENGTH: 606
<212> TYPE: DNA
<213> ORGANISM: Homo sapiens

<400> SEQUENCE: 9
gaagcttctc catgttctta gccaggttat ataacttctt ttgcttcttt cttttccaca     60
ttctacatat ttttcacaat gaggatgtgt cacttctata gttaaaaatg gaaatcttca    120
tttaaaagaa caatcagaca caaggcaagg tatgcttacc ttcccaatga ccaaggagca    180
gggagacatt ggtcgtggag gccataggtg accagccttg agggaaggga aggaagggga    240
ggtgcaggga ggcgcagcag aggcacccga gtgtgctcta cgaatgtaag tctgccagct    300
gctcctctgt gcctagcacc ctggaaagcg cccgcacaca gtgggccctc agcaaactcc    360
cactgagcaa agggccctgt gagtaaggac ctagaagcag ggtgtgcttg aggcatgggg    420
tgggagggca tccagcttgg ctggcggtgg gagccgatgc aaaggtgagc tgagaccaga    480
cggtagaaga ccttcagtgc tgggccgagg agggttcctt catcccatag agaagagctg    540
ccatccaaga cagaaggctg gggagtgaca tgttgaaatc agtatcttag gaaaataaag    600
ccactg                                                               606

<210> SEQ ID NO 10
```

<211> LENGTH: 664
<212> TYPE: DNA
<213> ORGANISM: Homo sapiens

<400> SEQUENCE: 10

| | | | | | |
|---|---|---|---|---|---|
| gccataaaat | caggataatg | gtggctgtgc | ctccttagag | tagaatgaga | atcagagcag | 60 |
| aacaagggaa | agctgcagtg | acttgtcagg | tgtcaacctt | cagcatgatg | ggagagccat | 120 |
| gggacccttc | ccctttccct | aagagagcca | gccctcacag | caggcctggg | atccaatgcc | 180 |
| cagcacccag | ctgggagccc | agggaccttg | gccaaaatct | ggttctgctt | caacttggtg | 240 |
| cccggccttt | gtcaagtcac | ttcctcattt | gcaaactggg | agagtttgga | tgaaactatt | 300 |
| gaatgaaatt | attttggggg | tttctttctg | gctctcacag | tcctcgcatg | ctcaccatgt | 360 |
| tcccttcaat | ttcattagca | cagcccaaca | aagggttaag | cagtggcagt | tcctctcgtt | 420 |
| ctttggttag | gacaggaagg | tcaggggtga | ggccaataca | agaggtagcc | gccacagctg | 480 |
| atgctggaaa | tgacaatagt | tctttcctag | actcatattt | gtcccctctc | cctgaagctt | 540 |
| tgcctgcagt | gcccttgtaa | agaagttggc | aagaagcagg | agtgaggctc | agcccctctc | 600 |
| tgaaatggat | acgccggttg | ctccccctca | tggctggtct | catttgcctt | cttcattttt | 660 |
| agac | | | | | | 664 |

<210> SEQ ID NO 11
<211> LENGTH: 688
<212> TYPE: DNA
<213> ORGANISM: Homo sapiens

<400> SEQUENCE: 11

| | | | | | |
|---|---|---|---|---|---|
| tgcctagaac | attctggtat | cccagacaga | agtgcaacac | caggtggagg | tgttgcagct | 60 |
| gagaagttct | gaccagcata | ccagcacccc | cttaaaagct | gtctatactt | gcggttctca | 120 |
| gctaggctgc | cacagaatcg | cccaagtctt | aaaaaaacag | gtctctgtcc | tactgcttga | 180 |
| gatgctggtt | ctctaggtct | gaggttctgg | cacctgtgtg | ttttttaaaac | tttacaaata | 240 |
| atttaaaagc | gccttcaagt | ccacaacaac | agaatatttc | cctccactcc | tcattgtcct | 300 |
| ggagttctct | aacagtgcag | ttctacaact | ggacacacga | tgtcgctttt | cagccacagt | 360 |
| tctcactaag | cggccccaca | gggcggcagg | tgccttctgc | agagagagag | agagggcctt | 420 |
| ggctgacagg | ccaagaccgg | gcatcctggc | tcctcctctg | tacagacttt | tcacagatgt | 480 |
| gaactctccc | tactccctgt | cttctgcccc | caaatgaagc | ctctcagctg | gcaagagctg | 540 |
| agaactacca | agcgagccat | tgctaatttc | tattgtgttt | ggaaccacaa | aaggcagaat | 600 |
| tattaaggct | gtaaaggacc | tcagagcatc | tggtgcagtg | agtttccaac | ttgtgaaaat | 660 |
| ctgatgtgat | ctcggacaag | tcacttaa | | | | 688 |

<210> SEQ ID NO 12
<211> LENGTH: 550
<212> TYPE: DNA
<213> ORGANISM: Homo sapiens

<400> SEQUENCE: 12

| | | | | | |
|---|---|---|---|---|---|
| caaagtggct | ctgattattt | cactcccaca | ggccactggc | tcagaggtat | agagctcacc | 60 |
| tgtggcagat | ggagatgcgg | atctgaggct | tctgatgctg | ccacacccag | cggcgccccc | 120 |
| caaattccgg | gcccctggat | gacatctggt | ctgttcctgc | agcatcagag | cacaatagag | 180 |
| ccagccacca | gtcccagccc | tgcctgcatc | ccatccattc | ctgggtgcct | aaccccgagg | 240 |
| atcccctggc | agtatgatgc | ggacctgtct | tggatcccag | ggatatgctg | gccacgggga | 300 |

```
ggagccggaa accaaccttt gtgtcactgt gtagtgacaa gtgcctttgg aggtcacaat    360
agccagtggt gatttctacc actgccccca gcagccaagg tggcagagga gccctgtcag    420 tcaccccat tctgttcatg gtctcacggt gggctccaca tgggggtgg cagccctctc    480 ccccacccca cccgacccct ttcgacagat agggtaatac aaatacaaat aacaccaaaa    540
gattgagttg                                                           550
```

<210> SEQ ID NO 13
<211> LENGTH: 531
<212> TYPE: DNA
<213> ORGANISM: Homo sapiens

<400> SEQUENCE: 13

```
ggatctccta cgtactgcta cgactgcaca caggtgcagg aaatggctgt ttgctttgcg    60
tttgaggaac ttggaaaggg agacgtggta gggaaagtag tggttagggg cactttcaga   120
ctgaaggatg tggggtgggg aatacgggat tcttggagtt gaggacgccg cttctctcgt   180
ctctagctaa tgtgagaaag acccttctgg acactaagcc tgcaattcca ctggtggcta   240
ccaggtgtcc gtggtgtcct ggggcgggtg taatgagagc gggagcctgt gaaaccaaaa   300
gcattgtttt tataaattca gcactcttca tccctatta ataaggttag cggtgcagtt    360
cttgcgtctc ctgccctgcc tcaccttgca atcatattca ttggcattcc tttcttccaa   420
gaacccacct aggaggcctt gcaggagata tctctggtgc tggctgttcc tgcagtctga   480
aaagccagtt aagatacaaa tatgtgagag acactgcttt gaatctgatt t            531
```

<210> SEQ ID NO 14
<211> LENGTH: 673
<212> TYPE: DNA
<213> ORGANISM: Homo sapiens

<400> SEQUENCE: 14

```
tgagggtaaa atgaaacaat aatcacgggt gcatcctgga gctctttctt acaaggcgtg    60
cccccaaatc tgtcccctct ttctgaggat gcccttcccc tattgtctcc ctggccattt   120
cctacccatt ctcaagggcc atgatctcag ggagttctcc tgactcaccc aggcatattg   180
gatctcctac gtactgctac gactgcacac aggtgcagga aatggctgtt tgctttgcgt   240
ttgaggaact tggaaaggga gacgtggtag ggaaagtagt ggttagggc actttcagac    300 tgaaggatgt ggggttgggga atacgggatt cttggagttg aggacgccgc ttctctcgtc   360
tctagctaat gtgagaaaga cccttctgga cactaagcct gcaattccac tggtggctac   420
caggtgtccg tggtgtcctg gggcgggtgt aatgagagcg ggagcctgtg aaaccaaaag   480
cattgttttt ataaattcag cactcttcaa tccctattaa taaggttagc ggtgcagttc   540
ttgcgtctcc tgccctgcct caccttgcaa tcatattcat tggcattcct ttcttccaag   600
aacccaccta ggaggccttg caggagatat ctctggtgct ggctgttcct gcagtctgaa   660
aagccagtta aga                                                       673
```

<210> SEQ ID NO 15
<211> LENGTH: 570
<212> TYPE: DNA
<213> ORGANISM: Homo sapiens

<400> SEQUENCE: 15

```
aaagacactg cagagaaaag aaagcacagc ctgctgccct gggaattaac atgatttagg    60
agacctgcag gtcaccccct catgactaaa agccatcctg gaatgaaggt ctgtggctat   120
```

```
ttctaggcaa aactgtctga taagataaaa tagctcaact cctgaccatt aagtcgtgaa        180
ggccatggcc atcgtaaatc tcatctttcc ggccctctgg cctgcatgca gtgcagccca        240
gccagtcggt ggcagccacc ttggtaggaa gggccctcat cctcctggct gtgcccaag         300 gactgggcag gcttcggtgc caagggtagt gcgagcactt gaaagccgcc ctgtatgttt        360
attgttttcc ccaggtgatc cagaattact cccgaactct accagctgaa atcctcctca        420
actcacatca gacaagacgg ccctgccact tacctgtcag atcactttgg gcaggtaagc        480 tcatttttcct gaatctttac ttccacacct taaaatgtga gcaatactat ctccctggca       540
aggttgtttg tgagggtaaa atgaaacaat                                         570

<210> SEQ ID NO 16
<211> LENGTH: 517
<212> TYPE: DNA
<213> ORGANISM: Homo sapiens

<400> SEQUENCE: 16
actcctagaa ccctaaagga agcccctgga cacgcaggaa ggtgtggaga ggagttctca         60
tacttgcact tgggaggagg gctcaggaga aacagaggct ggcaacaccc cctcacacac        120
tggtcctctg gagggccagt gtctacagac actgtggact gagtccacag agaggaaagg       180
gtcctgcctt catcagaact gctcagcaag cagttccatc ccaggggtc ctgcgaggta        240 agggaggggc agctagctag gtgaggggct gagagagtgg ggagggaaa gagggaagaa         300 gagagtgaga gggagaggga gggactgagc cgattctcag ctccttgacc gtttgctgag        360
ctctgtctga gtggacagat ggtcccaagt caggccacac cagagtggcc tttctgctcc       420
cctacaccct gcattcctca acattgctgg ccccggagag actttccttc agagaagcaa        480
atggctgggg aatggtgaaa gacactgcag agaaaag                                 517

<210> SEQ ID NO 17
<211> LENGTH: 586
<212> TYPE: DNA
<213> ORGANISM: Homo sapiens

<400> SEQUENCE: 17
gtatcaccag tgaagttggt gcacacagca gggcccaaac tgacatctca cagcacccag         60
caggtcactg tgggcatgat aggatgatgg gtcactgtgc cagccctgaa ggagttcaag        120
tccagatagg ggaaggtggt ggaccagacc cagacagaga ttctgagtcg ctgctgagac        180
tgggtgaggg tagtgggtac atgggaggac atatagcccg gcagcccagg gctggagtcc        240
acactcaggt tggggcagcc tggtctgcct ctcctgcagg agacttttcc aggcaggctt        300
gtccctccag aatgcacgaa tcaaatcctc tcaggatcag tctcatttc ctcgtgctgg         360 gggagcaggc tactcacaga agatgttgtt gcaaatgtaa gaatcacatg tcgatccaca        420
aactggcatt gagcagctac ctaggagatc aaagaaactc ttactttggg agctcctgcc        480
agggctcttt gggaggtctg gctagctctg gaggaagaga atgaacttgg ggagggcgtg        540
gaacagatga ggacgcaggc actgccattc aaagaggaga ggtctc                      586

<210> SEQ ID NO 18
<211> LENGTH: 1100
<212> TYPE: DNA
<213> ORGANISM: Homo sapiens

<400> SEQUENCE: 18
cacagctgga gacatgttac acttctgcaa atccaggctc cctttgtgca ttgtaatgga         60
```

```
agctggtagg atttccttgc tgccacagtt ttccaggcta ttttaacagg aggtggctct      120
tcctcgtccg cgcttgtgtg ctgcctcggg ctgtgtctcc aaatgtcagt acttgagagt      180
gaggaggcca cctcccctgc attgatctgt tctggctgag tttaaagcac agatcttggt      240
catcaggttt ttttaacttc ggctttggag acaacattct tttttttttt tttttttagat     300 ggagtctcgc tctgtcgccc aggctggaat gcagtggtgc gatctccggt tcatgccatt      360
ctcctgcctc agcctcccga gtacctggga ttacaggcgc ccaccaccat gcccggctaa      420 ttttttttgta tttttttagt agagacgggg tttcaccgtg ttagccagga tggtctcaat     480
ctcctgacct tgtgatccgc ccgcctgggc ctcccaaagt gctgggatta cagacgtgag      540
ccaccgcgcc cggccccaac attcttttt gcttgggata aaccctcttc aggctgttaa       600
tcaatataga taaaagtata ctgttctatt ctttcttctc aagtcatttt caatgctttc      660
tctgcatggg caatgccaaa atcccattga gcatgttctc tctgaggtca gggtttccaa      720
atcttttgtt tctcagagtg attgctggct tgtttggttg cctcagccag taattcttca      780
taccgcttat gacctttata ctcctgtacc cattttttcat gaacccacac cctctctggc     840
tgtttgctaa aacactggac atgatatttt cgggcacctc ctgtgttaat tttggtatga      900
acctccagct ggggatcact tcaatccata caaggccagc acggataggt tcccaccttg      960
gaccacacaa gatcaccaac ttgaaactta acaccagtgg acacttctgt tgttggaaca     1020
gaagatagta ttggctgaac tggggcttcc tcttttagta ctggatcttc ccttggtttt     1080
tctgatatgg tgtgaaccct                                                 1100

<210> SEQ ID NO 19
<211> LENGTH: 1236
<212> TYPE: DNA
<213> ORGANISM: Homo sapiens

<400> SEQUENCE: 19
gagctgagat cgcaccactt cactccagcc tgggcaacag agcaagactc tgccttgaaa       60
aaaaaaaaaa aaaagaacc cttgctctta tggagaagca ttctactggg gaaaacagac      120
aataaacaca tagataaata aaacatatgt cagaaagggg taagtgatgc tcagaaaaat      180
aggacaaggg atcagaagtg ctaggcgttg caatttaaaa taatgggtc tggaaagcca      240 cccctgagaag ggccaatgga gctatgccca gcctgtggta tccttcctca ggcaggggac     300
tgtaccccca gcttacaagc ttttcgagg caccttcagg gtttgagccc aaaatgcact       360
gcacattaag tgttattgat gggcttgtgg aaatctgctc tccgtcaggc tctgatgaaa      420 ctttttccaac aggagactga actcagtact gggcatggcc ccctgcacat agtaagtcca     480
cagcaaatgt gtgtgggtg aatactgtct tctttatcct ccctttttct actccagtcc      540
aggtagacgg tgtatctacc cacccaattt tgctgtttct ggtaccctca gtgggtcttg     600
cctgctcttc ctccttgaaa tcattactca gaggtctccg tgtcagctcc agacagatgg      660
gcctggtgct cctttatctc aatacaattc ccccgctccc aggctccagg ggaaatcctg      720
agctaacttt ggtctttcct aaactccaca cttcccttg gcacctctt tccccattgc       780 ggggctccct ttcagaattt gctgctttat ttatttattt attttgtca gaggtgcatt      840 aatgatgctt tatttaaaaa caaaaaactt ggccaggcgc ggtggcttat gcctgtaatc      900
ccagcacttt gggaggctga ggtgggcgga tcacaaggtc aggagatcaa gaccatccag      960
accaacatgg tgaaacccag tctgtactaa aaatacaaaa aaaaaaaaaa aaaaaatca     1020 gccgggcgtg gcacatgcct gtaattccag ctactcagga ggctgaggca ggagaatcac     1080
```

```
ttgaacccgg gaggcagagg ttgcagtgag ccgagattgg gccactgcac tccagcctgg   1140
gtgacagagc gagactccat ctcaaacaaa aaaacaccac aaataaataa aaataaaaa    1200 caaaaaacca aaaacagtcc attccatgtc gtgttg                             1236
```

<210> SEQ ID NO 20
<211> LENGTH: 1171
<212> TYPE: DNA
<213> ORGANISM: Homo sapiens

<400> SEQUENCE: 20

```
accgtgcaga ggtagatggt acttctcaca tcctgtaatt aattgcttgc atgcctgtgg     60
tacaccgtac cattgctcac aaatatttcc tcttcctctc tggagaagga ttacacttcc    120
ttgatccatt ggcctcactc aggcttcgcc acatgactgg tgctggccag tgaagtggga    180
catgtgagtt actggggagc agaaactttc aaagccaagc atggctcacc ttgttctctc    240
ttccctctgt tacaaggatg gcagtgcccc agccagaaac cacactgcca gcctggcata    300
ggagtggagc agggcacaca taagtgtgag agaaatgaac ttcacctcag tgctcgaggc    360
ccctgggacc atggactcat tgttactgc agcataaact agctggtctt gacttcagct     420
tctgcctctc ttccctggct tgccttcac aaaatcaaga gtctgatctt actcatatta     480
tagagctggt cttcaaccat gttctttttt tttttttcct tttttttttt ttgagatgga    540
gtttcgctca tgtagtccag gatggagtgc aatggtgcga tctgggctca ctgcaatctc    600 tgcctcctg gttcaagcga ttctcctgcc tcagcctccc aaatggctgg gattacaggt     660
gcttgccacc acgcctagct aattttttgta tttttagaag agataggatt tcaccatgtt    720
ggccaggcta tctcaaactc ctgacctcag gagatctgcc cgcttcggcc tcccaaagtg    780
ctggcattac aggcatgagc caccatgccc agccccatgt tcttcgaatg gccaagaata    840
tcagtaggta aggtttgttg agcatggatt gtgtgccagg tgctgtgcta tgccctttggc   900 aagcgttatc ccattacatc ctttaacagc actctctggt gggtactgct cttatacaag    960
atttacaaaa gagaaaagag actcagagga atgtaggggc tcacgtgaga ttgtaaagta    1020
gtgagaagtg gagctggtcc ttcagctcaa atccctctga tgccaaagaa ctcaaactct    1080
gcagttccat catgtgcatc ctcactctct cacttcctgc agaggatctg tggaggttgt    1140
aactattgtt ttcacctgtc tcttccactg g                                  1171
```

<210> SEQ ID NO 21
<211> LENGTH: 1007
<212> TYPE: DNA
<213> ORGANISM: Homo sapiens

<400> SEQUENCE: 21

```
acggtgtaca catttggtta gttccttctt ttacaccata aattatcaga gacaacccctt    60 ttggaaagca atttggcaat aatatcaagt gacataaaga tgttcatagc ctttggccca    120
ataatcttcc tcctgggaat taatcctaag aaaataattc acaaggaaga aagaaccatt    180
ttgtatctac aaagacattt attggggtgt tatttatgat agggaaaaac tggagacacc    240
ctccccagcc aacatagagg gatggtccta taaattatga tacatccatc caatgaaatg    300
ttaccctgcc agtaaaaatg gtaaattgaa aattgtgtag caacaagaaa gagtgttcag    360
aaaataaaag caagtgaaaa aaggagcaca ggattgtcta tatgctgtga tcaatggcaa    420
tgctgacaaa tccatgtatg tgtagatagt tgtagtgtta cctgtaaggc acgataaggc    480
ggatgtaact gtgcttcaaa tgttcttttc catagctgtg gagtccttct agtatgaaat    540
```

```
catttttgta aaatcgcaat tgtcaccag gggttttgac tttccttatt gcctcgtggg        600
aggtggcaga ggcagcacat ctcagaccga gcctcggttc ctcccctac ctcccaccgc        660 tgcgcttgaa gaaagatgct gcagcctccc cagtccccat gccagcgctc ccactttcct      720
ctgagctttc ggtggcagac agcgccttgg gcacttttc atgctcataa ttcgaattac       780
ctgtttaagt cggtcaaatg aaaaaatacc agctccgccc ccacgcgggc tggccggggc      840
gcctggagcg ccagggcggc tgcagcgcgc tctccgcggc cgtcggccct gagctcattt      900
cctggggcgc gcgcgccggg ctatttcagc ctggcgctgt gcaaacagga caatttactg     960
cggccaaaag ggacccaaat tacaatcgta tcacagacaa atatccg                   1007

<210> SEQ ID NO 22
<211> LENGTH: 198
<212> TYPE: DNA
<213> ORGANISM: Homo sapiens

<400> SEQUENCE: 22
ggctggagca gggacttgaa aaagggagag ggctcaggag actcagagga ggaggaaagt       60
gtgtgagcag taggcagggt gtgtgtgtgt gtgtgtgtgt gtgtgcacgc                 120
gcgcgcatgc aggcctgtgt agggctggga agaacaaag caaaagggtg cacaaggcat      180
ccagaagcca gggcaatg                                                   198

<210> SEQ ID NO 23
<211> LENGTH: 369
<212> TYPE: DNA
<213> ORGANISM: Homo sapiens

<400> SEQUENCE: 23
gagcagaagg ccttgactga gccccaggag aggcaggaca ccagggtgc acacccataa        60 acacacacat acacatgtat gtctcctccc tggagcctga gagtcctcat atacagcagg    120
tgcatgtggg ccacacatca cacaaaattg aatacaggca ggctcagagc accagcacac    180
acgtatgtcc ttgacaccct tagagatact actaagcacg tgtgtgtacc tgctcaccca    240
tatggcagag cccctggatc tgggcagaaa tgccaaagca gggcaggcg cgtgtgcgcg    300 cacacacaca cacacacaca cacacacaca ctagcacagc cacaaaagct caatccacat    360
ccagcattc                                                             369

<210> SEQ ID NO 24
<211> LENGTH: 436
<212> TYPE: DNA
<213> ORGANISM: Homo sapiens
<220> FEATURE:
<221> NAME/KEY: misc_feature
<222> LOCATION: 121,153
<223> OTHER INFORMATION: n = A,T,C or G

<400> SEQUENCE: 24
tcaggacgtt gcactttgac agaaggctct ggaaggaaac tttaaaggga gccttccaga       60
gggaaatgcg gtgttggggt aggtctgcct ttggctatgg gctttctggc tgccggaggg    120
ncccagggtc ccccaggaaa gccttctgtg ganggtcttt tgagagagac aaagcagagg    180
ggtggaggaa gggcggctca ggtggaagga gtgaggacaa aggtgagtgc ccctgggcag    240
gaagtgctga aagagagaag gagggaggcc accaggcctg ggcctggagc cagcctggga    300
gactcccagc cgcccacttc tcggggcctc ccttttccag cccttgctt tcgaggcagc    360 agtgccatta tttggggaaa ccagctaacc agataggaca gcaaaccggg gatttatgtg    420
```
gtgtgggaac agctca 436

<210> SEQ ID NO 25
<211> LENGTH: 670
<212> TYPE: DNA
<213> ORGANISM: Homo sapiens

<400> SEQUENCE: 25

```
ctgggattac aggtgtctgg caccatacct agctaatttt tgtattttta gtagagatgg    60
ggtcttgcca tgttggccag actggttttcc aactccccac ctcaggtgat ctgcccgccc  120
tggcctccca aagtgctggg attacgggca tgagccactg tgcctgacct cagctctgtt  180
attaataagc taaatggctt tgagcgactt gccttatcac ttgagcctca gtttcctcat  240
ctgtaaaatg gggataaact tcttccgtcc gcatgaggat gctgagagac gtgagtgagg  300
tggtctatga agctcttgt catagcctgg catgcagggg taacatctgg atgatgaaga  360
tgatgatacc tgagattttt gccttacaga caactccaga gagccctgtg aaatatttat  420
atgccactga acagggcaca agatgaagcc attagcctgc gcttacatag tagaatgtgt  480
gaatcagatg agatgcttgg tctctagtaa gaccttaagg gatggacaga agacaggcag  540
attttggata tggtatacgt ggctgtgggc tagcgtgttt actactgggc tgggatgta   600
tttggaatgt acacatgtgt cctttgcttc tcagaacact tgaggcagc agagttacta   660
ctgcctgcca                                                         670
```

<210> SEQ ID NO 26
<211> LENGTH: 460
<212> TYPE: DNA
<213> ORGANISM: Homo sapiens

<400> SEQUENCE: 26

```
gaggttagac gggtctgagt tcaagcccca ggtctgccac ttcctggctg tgtgccctgg    60
aacaagtcac cttatctctc tgaacttctt ttttttttt ttcttttga gatggagtct   120
cgttctgtcg cccaggctgg agtgcagtgg catgatctca gctcactgca agctccgcct  180
cccgggctca cgccattctc ttgcctcagc ctcccgagta gctgggacta caagcacccg  240
ccaccacgcc cggctaattt tttgtatttt ttagtagaga cggggtttca ccgtgttagc  300
caggatggtc tcaatctcct gacctcgtga tccgcccgcc tcggcctccc aaagtgctgg  360
gattacaggc atgagccacc atgcctggcc atctctctga acttctgttt cctcatctga  420
gatgacagtc agagtgggat ctgtgtaagg cactttgcac                        460
```

<210> SEQ ID NO 27
<211> LENGTH: 482
<212> TYPE: DNA
<213> ORGANISM: Homo sapiens

<400> SEQUENCE: 27

```
tgccaattag ccacactctt ctctagagag gtttcaagtc attttctttc acagcaatgg    60
caaggctctt aaataaggtc cttgaagttt cttcgggtct cctcccacct gctccctgcc  120
cccttcacct ccacccacct gcttcccttt ctcatccccc agaggcggag gcttccgagg  180
aatttggggt agggaaatag gaatcagggg ctcctcattc cccaaaggag cctctttggc  240
aagcaggcac gtgggtctcc gggctggtgc acatcacagg gcagccagcc caagtgccat  300
cttgatgccc aatcagtctt cctcatggct gcgccctgct ggtctctcag agggttaatg  360
caatttcttg gaggacgaca ttcctaacac ccaggggcca gaactccttc cccactggtt  420
```

-continued

```
attcccatgg cccagagcag caggatgggg gcagaaacag gcatggacct taacagcagc    480
gt                                                                  482

<210> SEQ ID NO 28
<211> LENGTH: 16
<212> TYPE: DNA
<213> ORGANISM: Artificial Sequence
<220> FEATURE:
<223> OTHER INFORMATION: PCR primer

<400> SEQUENCE: 28
attggcctgg cttctg                                                   16

<210> SEQ ID NO 29
<211> LENGTH: 16
<212> TYPE: DNA
<213> ORGANISM: Artificial Sequence
<220> FEATURE:
<223> OTHER INFORMATION: PCR primer

<400> SEQUENCE: 29
ggctggagca gggact                                                   16

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
tcctgtgatc gcattgagac                                               20

<210> SEQ ID NO 31
<211> LENGTH: 21
<212> TYPE: DNA
<213> ORGANISM: Artificial Sequence
<220> FEATURE:
<223> OTHER INFORMATION: PCR primer

<400> SEQUENCE: 31
ccctgccatt ctggatagtt t                                             21

<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
cagtggcttt attttcctaa                                               20

<210> SEQ ID NO 33
<211> LENGTH: 20
<212> TYPE: DNA
<213> ORGANISM: Artificial Sequence
<220> FEATURE:
<223> OTHER INFORMATION: PCR primer

<400> SEQUENCE: 33
gaagcttctc catgttctta                                               20

<210> SEQ ID NO 34
<211> LENGTH: 20
<212> TYPE: DNA
```

-continued

<213> ORGANISM: Artificial Sequence
<220> FEATURE:
<223> OTHER INFORMATION: PCR primer

<400> SEQUENCE: 34
gtctaaaaat gaagaaggca                                          20

<210> SEQ ID NO 35
<211> LENGTH: 20
<212> TYPE: DNA
<213> ORGANISM: Artificial Sequence
<220> FEATURE:
<223> OTHER INFORMATION: PCR primer

<400> SEQUENCE: 35
ttaagtgact tgtccgagat                                          20

<210> SEQ ID NO 36
<211> LENGTH: 20
<212> TYPE: DNA
<213> ORGANISM: Artificial Sequence
<220> FEATURE:
<223> OTHER INFORMATION: PCR primer

<400> SEQUENCE: 36
caactcaatc ttttggtgtt                                          20

<210> SEQ ID NO 37
<211> LENGTH: 20
<212> TYPE: DNA
<213> ORGANISM: Artificial Sequence
<220> FEATURE:
<223> OTHER INFORMATION: PCR primer

<400> SEQUENCE: 37
aaatcagatt caagcagtgt                                          20

<210> SEQ ID NO 38
<211> LENGTH: 20
<212> TYPE: DNA
<213> ORGANISM: Artificial Sequence
<220> FEATURE:
<223> OTHER INFORMATION: PCR primer

<400> SEQUENCE: 38
tcttaactgg cttttcagac                                          20

<210> SEQ ID NO 39
<211> LENGTH: 20
<212> TYPE: DNA
<213> ORGANISM: Artificial Sequence
<220> FEATURE:
<223> OTHER INFORMATION: PCR primer

<400> SEQUENCE: 39
attgtttcat tttaccctca                                          20

<210> SEQ ID NO 40
<211> LENGTH: 20
<212> TYPE: DNA
<213> ORGANISM: Artificial Sequence
<220> FEATURE:
<223> OTHER INFORMATION: PCR primer

<400> SEQUENCE: 40
gccataaaat caggataatg                                          20

```
<210> SEQ ID NO 41
<211> LENGTH: 20
<212> TYPE: DNA
<213> ORGANISM: Artificial Sequence
<220> FEATURE:
<223> OTHER INFORMATION: PCR primer

<400> SEQUENCE: 41
tgcctagaac attctggtat                                                   20

<210> SEQ ID NO 42
<211> LENGTH: 20
<212> TYPE: DNA
<213> ORGANISM: Artificial Sequence
<220> FEATURE:
<223> OTHER INFORMATION: PCR primer

<400> SEQUENCE: 42
caaagtggct ctgattattt                                                   20

<210> SEQ ID NO 43
<211> LENGTH: 20
<212> TYPE: DNA
<213> ORGANISM: Artificial Sequence
<220> FEATURE:
<223> OTHER INFORMATION: PCR primer

<400> SEQUENCE: 43
ggatctccta cgtactgcta                                                   20

<210> SEQ ID NO 44
<211> LENGTH: 20
<212> TYPE: DNA
<213> ORGANISM: Artificial Sequence
<220> FEATURE:
<223> OTHER INFORMATION: PCR primer

<400> SEQUENCE: 44
tgagggtaaa atgaaacaat                                                   20

<210> SEQ ID NO 45
<211> LENGTH: 20
<212> TYPE: DNA
<213> ORGANISM: Artificial Sequence
<220> FEATURE:
<223> OTHER INFORMATION: PCR primer

<400> SEQUENCE: 45
aaagacactg cagagaaaag                                                   20

<210> SEQ ID NO 46
<211> LENGTH: 20
<212> TYPE: DNA
<213> ORGANISM: Artificial Sequence
<220> FEATURE:
<223> OTHER INFORMATION: PCR primer

<400> SEQUENCE: 46
cttttctctg cagtgtcttt                                                   20

<210> SEQ ID NO 47
<211> LENGTH: 20
<212> TYPE: DNA
<213> ORGANISM: Artificial Sequence
<220> FEATURE:
<223> OTHER INFORMATION: PCR primer
```

```
<400> SEQUENCE: 47
gagacctctc ctctttgaat                                              20

<210> SEQ ID NO 48
<211> LENGTH: 20
<212> TYPE: DNA
<213> ORGANISM: Artificial Sequence
<220> FEATURE:
<223> OTHER INFORMATION: PCR primer

<400> SEQUENCE: 48
ggtttcaact agttctggtg                                              20

<210> SEQ ID NO 49
<211> LENGTH: 20
<212> TYPE: DNA
<213> ORGANISM: Artificial Sequence
<220> FEATURE:
<223> OTHER INFORMATION: PCR primer

<400> SEQUENCE: 49
ctagggctta gaagtttcct                                              20

<210> SEQ ID NO 50
<211> LENGTH: 20
<212> TYPE: DNA
<213> ORGANISM: Artificial Sequence
<220> FEATURE:
<223> OTHER INFORMATION: PCR primer

<400> SEQUENCE: 50
actcctagaa ccctaaagga                                              20

<210> SEQ ID NO 51
<211> LENGTH: 20
<212> TYPE: DNA
<213> ORGANISM: Artificial Sequence
<220> FEATURE:
<223> OTHER INFORMATION: PCR primer

<400> SEQUENCE: 51
gtatcaccag tgaagttggt                                              20

<210> SEQ ID NO 52
<211> LENGTH: 20
<212> TYPE: DNA
<213> ORGANISM: Artificial Sequence
<220> FEATURE:
<223> OTHER INFORMATION: PCR primer

<400> SEQUENCE: 52
gataaatgga tatggcaaag                                              20

<210> SEQ ID NO 53
<211> LENGTH: 20
<212> TYPE: DNA
<213> ORGANISM: Artificial Sequence
<220> FEATURE:
<223> OTHER INFORMATION: PCR primer

<400> SEQUENCE: 53
ggtttataat ttgcaaccag                                              20

<210> SEQ ID NO 54
<211> LENGTH: 20
<212> TYPE: DNA
```

```
<213> ORGANISM: Artificial Sequence
<220> FEATURE:
<223> OTHER INFORMATION: PCR primer

<400> SEQUENCE: 54
attccctaag agatttgtcc                                                  20

<210> SEQ ID NO 55
<211> LENGTH: 20
<212> TYPE: DNA
<213> ORGANISM: Artificial Sequence
<220> FEATURE:
<223> OTHER INFORMATION: PCR primer

<400> SEQUENCE: 55
gagaggacaa acattcaaac                                                  20

<210> SEQ ID NO 56
<211> LENGTH: 20
<212> TYPE: DNA
<213> ORGANISM: Artificial Sequence
<220> FEATURE:
<223> OTHER INFORMATION: PCR primer

<400> SEQUENCE: 56
tttagaccta tcactcccaa                                                  20

<210> SEQ ID NO 57
<211> LENGTH: 20
<212> TYPE: DNA
<213> ORGANISM: Artificial Sequence
<220> FEATURE:
<223> OTHER INFORMATION: PCR primer

<400> SEQUENCE: 57
ctactgggac aaaccattac                                                  20

<210> SEQ ID NO 58
<211> LENGTH: 20
<212> TYPE: DNA
<213> ORGANISM: Artificial Sequence
<220> FEATURE:
<223> OTHER INFORMATION: PCR primer

<400> SEQUENCE: 58
agagagggtg agtaacttcc                                                  20

<210> SEQ ID NO 59
<211> LENGTH: 20
<212> TYPE: DNA
<213> ORGANISM: Artificial Sequence
<220> FEATURE:
<223> OTHER INFORMATION: PCR primer

<400> SEQUENCE: 59
aataaaagaa agtttggggt                                                  20

<210> SEQ ID NO 60
<211> LENGTH: 20
<212> TYPE: DNA
<213> ORGANISM: Artificial Sequence
<220> FEATURE:
<223> OTHER INFORMATION: PCR primer

<400> SEQUENCE: 60
gcagagtgct tttagaacat                                                  20
```

```
<210> SEQ ID NO 61
<211> LENGTH: 20
<212> TYPE: DNA
<213> ORGANISM: Artificial Sequence
<220> FEATURE:
<223> OTHER INFORMATION: PCR primer

<400> SEQUENCE: 61
aggtggaggt tacagtaaga                                          20

<210> SEQ ID NO 62
<211> LENGTH: 20
<212> TYPE: DNA
<213> ORGANISM: Artificial Sequence
<220> FEATURE:
<223> OTHER INFORMATION: PCR primer

<400> SEQUENCE: 62
aagcagtatc tctgaagctg                                          20

<210> SEQ ID NO 63
<211> LENGTH: 20
<212> TYPE: DNA
<213> ORGANISM: Artificial Sequence
<220> FEATURE:
<223> OTHER INFORMATION: PCR primer

<400> SEQUENCE: 63 cctttcttg gttcagataa                                           20

<210> SEQ ID NO 64
<211> LENGTH: 21
<212> TYPE: DNA
<213> ORGANISM: Artificial Sequence
<220> FEATURE:
<223> OTHER INFORMATION: PCR primer

<400> SEQUENCE: 64
acggtgtaca catttggtta g                                        21

<210> SEQ ID NO 65
<211> LENGTH: 21
<212> TYPE: DNA
<213> ORGANISM: Artificial Sequence
<220> FEATURE:
<223> OTHER INFORMATION: PCR primer

<400> SEQUENCE: 65
cggatatttg tctgtgatac g                                        21

<210> SEQ ID NO 66
<211> LENGTH: 21
<212> TYPE: DNA
<213> ORGANISM: Artificial Sequence
<220> FEATURE:
<223> OTHER INFORMATION: PCR primer

<400> SEQUENCE: 66
accgtgcaga ggtagatggt a                                        21

<210> SEQ ID NO 67
<211> LENGTH: 20
<212> TYPE: DNA
<213> ORGANISM: Artificial Sequence
<220> FEATURE:
<223> OTHER INFORMATION: PCR primer
```

```
<400> SEQUENCE: 67
ccagtggaag agacaggtga                                               20

<210> SEQ ID NO 68
<211> LENGTH: 20
<212> TYPE: DNA
<213> ORGANISM: Artificial Sequence
<220> FEATURE:
<223> OTHER INFORMATION: PCR primer

<400> SEQUENCE: 68
gagctgagat cgcaccactt                                               20

<210> SEQ ID NO 69
<211> LENGTH: 21
<212> TYPE: DNA
<213> ORGANISM: Artificial Sequence
<220> FEATURE:
<223> OTHER INFORMATION: PCR primer

<400> SEQUENCE: 69
caacacgaca tggaatggac t                                             21

<210> SEQ ID NO 70
<211> LENGTH: 21
<212> TYPE: DNA
<213> ORGANISM: Artificial Sequence
<220> FEATURE:
<223> OTHER INFORMATION: PCR primer

<400> SEQUENCE: 70
cacagctgga gacatgttac a                                             21

<210> SEQ ID NO 71
<211> LENGTH: 21
<212> TYPE: DNA
<213> ORGANISM: Artificial Sequence
<220> FEATURE:
<223> OTHER INFORMATION: PCR primer

<400> SEQUENCE: 71
agggttcaca ccatatcaga a                                             21

<210> SEQ ID NO 72
<211> LENGTH: 19
<212> TYPE: DNA
<213> ORGANISM: Artificial Sequence
<220> FEATURE:
<223> OTHER INFORMATION: PCR primer

<400> SEQUENCE: 72
acgctgctgt taaggtcca                                                19

<210> SEQ ID NO 73
<211> LENGTH: 21
<212> TYPE: DNA
<213> ORGANISM: Artificial Sequence
<220> FEATURE:
<223> OTHER INFORMATION: PCR primer

<400> SEQUENCE: 73
tgccaattag ccacactctt c                                             21

<210> SEQ ID NO 74
<211> LENGTH: 20
<212> TYPE: DNA
```

<213> ORGANISM: Artificial Sequence
<220> FEATURE:
<223> OTHER INFORMATION: PCR primer

<400> SEQUENCE: 74
gtgcaaagtg ccttacacag                                          20

<210> SEQ ID NO 75
<211> LENGTH: 21
<212> TYPE: DNA
<213> ORGANISM: Artificial Sequence
<220> FEATURE:
<223> OTHER INFORMATION: PCR primer

<400> SEQUENCE: 75
gaggttagac gggtctgagt t                                        21

<210> SEQ ID NO 76
<211> LENGTH: 21
<212> TYPE: DNA
<213> ORGANISM: Artificial Sequence
<220> FEATURE:
<223> OTHER INFORMATION: PCR primer

<400> SEQUENCE: 76
tggcaggcag tagtaactct g                                        21

<210> SEQ ID NO 77
<211> LENGTH: 20
<212> TYPE: DNA
<213> ORGANISM: Artificial Sequence
<220> FEATURE:
<223> OTHER INFORMATION: PCR primer

<400> SEQUENCE: 77
ctgggattac aggtgtctgg                                          20

<210> SEQ ID NO 78
<211> LENGTH: 21
<212> TYPE: DNA
<213> ORGANISM: Artificial Sequence
<220> FEATURE:
<223> OTHER INFORMATION: PCR primer

<400> SEQUENCE: 78
tgagctgttc ccacaccaca t                                        21

<210> SEQ ID NO 79
<211> LENGTH: 21
<212> TYPE: DNA
<213> ORGANISM: Artificial Sequence
<220> FEATURE:
<223> OTHER INFORMATION: PCR primer

<400> SEQUENCE: 79
tcaggacgtt gcactttgac a                                        21

<210> SEQ ID NO 80
<211> LENGTH: 21
<212> TYPE: DNA
<213> ORGANISM: Artificial Sequence
<220> FEATURE:
<223> OTHER INFORMATION: PCR primer

<400> SEQUENCE: 80
gaatgctgga tgtggattga g                                        21

```
<210> SEQ ID NO 81
<211> LENGTH: 20
<212> TYPE: DNA
<213> ORGANISM: Artificial Sequence
<220> FEATURE:
<223> OTHER INFORMATION: PCR primer

<400> SEQUENCE: 81
gagcagaagg ccttgactga                                               20

<210> SEQ ID NO 82
<211> LENGTH: 21
<212> TYPE: DNA
<213> ORGANISM: Artificial Sequence
<220> FEATURE:
<223> OTHER INFORMATION: PCR primer

<400> SEQUENCE: 82
gccttcagtt tgtcccgttc t                                             21

<210> SEQ ID NO 83
<211> LENGTH: 20
<212> TYPE: DNA
<213> ORGANISM: Artificial Sequence
<220> FEATURE:
<223> OTHER INFORMATION: PCR primer

<400> SEQUENCE: 83
cgcgaggtca ggagttcgat                                               20

<210> SEQ ID NO 84
<211> LENGTH: 21
<212> TYPE: DNA
<213> ORGANISM: Artificial Sequence
<220> FEATURE:
<223> OTHER INFORMATION: PCR primer

<400> SEQUENCE: 84
ccactgaaca gggcacaaga t                                             21

<210> SEQ ID NO 85
<211> LENGTH: 21
<212> TYPE: DNA
<213> ORGANISM: Artificial Sequence
<220> FEATURE:
<223> OTHER INFORMATION: PCR primer

<400> SEQUENCE: 85
gaattactgg ctgaggcaac c                                             21

<210> SEQ ID NO 86
<211> LENGTH: 17
<212> TYPE: DNA
<213> ORGANISM: Artificial Sequence
<220> FEATURE:
<223> OTHER INFORMATION: PCR primer

<400> SEQUENCE: 86
gcctgcgctt acatagt                                                  17

<210> SEQ ID NO 87
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 87
aggcgggcgg atcacaaggt c                                         21

<210> SEQ ID NO 88
<211> LENGTH: 22
<212> TYPE: DNA
<213> ORGANISM: Artificial Sequence
<220> FEATURE:
<223> OTHER INFORMATION: PCR primer

<400> SEQUENCE: 88
ggctcactgc aacctccacc ta                                        22

<210> SEQ ID NO 89
<211> LENGTH: 24
<212> TYPE: DNA
<213> ORGANISM: Artificial Sequence
<220> FEATURE:
<223> OTHER INFORMATION: PCR primer

<400> SEQUENCE: 89
aaccaaacaa gccagcaatc actc                                      24

<210> SEQ ID NO 90
<211> LENGTH: 22
<212> TYPE: DNA
<213> ORGANISM: Artificial Sequence
<220> FEATURE:
<223> OTHER INFORMATION: PCR primer

<400> SEQUENCE: 90
tgggaggctg aggcaagaga at                                        22

<210> SEQ ID NO 91
<211> LENGTH: 18
<212> TYPE: DNA
<213> ORGANISM: Artificial Sequence
<220> FEATURE:
<223> OTHER INFORMATION: PCR primer

<400> SEQUENCE: 91
actgggcctg ggatgtat                                             18

<210> SEQ ID NO 92
<211> LENGTH: 19
<212> TYPE: DNA
<213> ORGANISM: Artificial Sequence
<220> FEATURE:
<223> OTHER INFORMATION: PCR primer

<400> SEQUENCE: 92
aaaaattggc tgggtgtgg                                            19

<210> SEQ ID NO 93
<211> LENGTH: 22
<212> TYPE: DNA
<213> ORGANISM: Artificial Sequence
<220> FEATURE:
<223> OTHER INFORMATION: PCR primer

<400> SEQUENCE: 93
caggctggag tgcaatggtg tg                                        22

<210> SEQ ID NO 94
<211> LENGTH: 22
<212> TYPE: DNA
```

```
<213> ORGANISM: Artificial Sequence
<220> FEATURE:
<223> OTHER INFORMATION: PCR primer

<400> SEQUENCE: 94
tgggaggctg aggcaagaga at                                          22

<210> SEQ ID NO 95
<211> LENGTH: 20
<212> TYPE: DNA
<213> ORGANISM: Artificial Sequence
<220> FEATURE:
<223> OTHER INFORMATION: PCR primer

<400> SEQUENCE: 95
ctcactgcag cctcaactcg                                             20

<210> SEQ ID NO 96
<211> LENGTH: 24
<212> TYPE: DNA
<213> ORGANISM: Artificial Sequence
<220> FEATURE:
<223> OTHER INFORMATION: PCR primer

<400> SEQUENCE: 96
tagcagaagg gggaaggggg aacg                                        24

<210> SEQ ID NO 97
<211> LENGTH: 24
<212> TYPE: DNA
<213> ORGANISM: Artificial Sequence
<220> FEATURE:
<223> OTHER INFORMATION: PCR primer

<400> SEQUENCE: 97
gacggtgtac acatttggtt agtt                                        24

<210> SEQ ID NO 98
<211> LENGTH: 24
<212> TYPE: DNA
<213> ORGANISM: Artificial Sequence
<220> FEATURE:
<223> OTHER INFORMATION: PCR primer

<400> SEQUENCE: 98
gcacagttac atccgcctta tcgt                                        24

<210> SEQ ID NO 99
<211> LENGTH: 24
<212> TYPE: DNA
<213> ORGANISM: Artificial Sequence
<220> FEATURE:
<223> OTHER INFORMATION: PCR primer

<400> SEQUENCE: 99
tgcagacacc cagagaagac gact                                        24

<210> SEQ ID NO 100
<211> LENGTH: 22
<212> TYPE: DNA
<213> ORGANISM: Artificial Sequence
<220> FEATURE:
<223> OTHER INFORMATION: PCR primer

<400> SEQUENCE: 100
tggaccctgc cctcacgatg ga                                          22
```

<210> SEQ ID NO 101
<211> LENGTH: 56
<212> TYPE: DNA
<213> ORGANISM: Homo sapiens

<400> SEQUENCE: 101
tgggattaca ggtgcatgct accatgcccg gctaattttt ttgtattttt ttagta      56

<210> SEQ ID NO 102
<211> LENGTH: 16
<212> TYPE: DNA
<213> ORGANISM: Homo sapiens

<400> SEQUENCE: 102
accatgcccg gctaat      16

<210> SEQ ID NO 103
<211> LENGTH: 21
<212> TYPE: DNA
<213> ORGANISM: Homo sapiens

<400> SEQUENCE: 103
ctaccatgcc cggctaattt t      21

<210> SEQ ID NO 104
<211> LENGTH: 21
<212> TYPE: DNA
<213> ORGANISM: Artificial Sequence
<220> FEATURE:
<223> OTHER INFORMATION: PCR primer

<400> SEQUENCE: 104
tactactggg cctgggatgt a      21

<210> SEQ ID NO 105
<211> LENGTH: 22
<212> TYPE: DNA
<213> ORGANISM: Artificial Sequence
<220> FEATURE:
<223> OTHER INFORMATION: PCR primer

<400> SEQUENCE: 105
tagagaaaga cctcgttatt gg      22

<210> SEQ ID NO 106
<211> LENGTH: 45
<212> TYPE: DNA
<213> ORGANISM: Artificial Sequence
<220> FEATURE:
<223> OTHER INFORMATION: PCR primer

<400> SEQUENCE: 106
tactaaaaaa tacaaaaaaa ttagccgggc atggtggtgg gcgcc      45

<210> SEQ ID NO 107
<211> LENGTH: 46
<212> TYPE: DNA
<213> ORGANISM: Artificial Sequence
<220> FEATURE:
<223> OTHER INFORMATION: PCR primer

<400> SEQUENCE: 107
aataaaaaat attagccggg ctaggtagca tgcacctgta atccca      46

<210> SEQ ID NO 108

```
<211> LENGTH: 52
<212> TYPE: DNA
<213> ORGANISM: Artificial Sequence
<220> FEATURE:
<223> OTHER INFORMATION: PCR primer

<400> SEQUENCE: 108
tactaaaaaa atacaaaaaa attagccggg ctaggtagca cctgtaatcc ca          52
```